United States Patent [19]
Kakefuda et al.

[11] Patent Number: 5,853,973
[45] Date of Patent: Dec. 29, 1998

[54] STRUCTURE BASED DESIGNED HERBICIDE RESISTANT PRODUCTS

[75] Inventors: Genichi Kakefuda, Yardley, Pa.; Karl-Heinz Ott, Lawrenceville, N.J.; Jae-Gyu Kwagh, Fairless Hills; Gerald W. Stockton, Yardley, both of Pa.

[73] Assignee: American Cyanamid Company, Wayne, N.J.

[21] Appl. No.: 426,125

[22] Filed: Apr. 20, 1995

[51] Int. Cl.$^6$ .................................................. C12Q 1/00
[52] U.S. Cl. .................................. 435/4; 435/6; 435/29; 435/232; 435/252; 435/252.33; 435/320.1; 536/23.2
[58] Field of Search .............................. 435/172.1, 172.3, 435/183, 320.1, 6, 4, 29, 232, 252.3, 252.33; 536/23.2

[56] References Cited

U.S. PATENT DOCUMENTS

| | | | |
|---|---|---|---|
| 4,883,914 | 11/1989 | Alvarado et al. | 564/91 |
| 5,013,659 | 5/1991 | Bedbrook et al. | 435/172.3 |
| 5,141,870 | 8/1992 | Bedbrook et al. | 435/320.1 |
| 5,378,824 | 1/1995 | Bedbrook et al. | 536/23.6 |

OTHER PUBLICATIONS

Ibdah et al. *Protein Science*, 3:479–S, 1994.
Gerwick, et al., *Pestic. Sci.* 29:357–364, 1990.
Rodaway et al., *Mechanisms of Selectively of Ac 322,140 in Paddy Rice, Wheat and Barley*, Proceedings of the Brighton Crop Protection Conference–Weeds, 1993.
The Pesticide Manual 10th Ed. pp. 888–889, Clive Tomlin, Ed., British Crop Protection Council, 49 Downing Street, Farmham, Surrey G49 7PH, United Kingdom.
Chaleff et al., *Science* 224:1443, 1984.
LaRossa et al., *J.Biol.Chem.* 259:8753, 1984.
Ray, *Plant Physiol.* 75:827, 11984.
Shaner et al., *Plant Physiol.* 76:545, 1984.
Whittle, et al., *Annu. Rev. Biophys. Biomol. Struct.*, 23:349, 1994.
Chang et al., *J. Bacteriol.* 170:3937, 1988.
Schloss, J.V. et al. In *Biosynthesis of branched chain amino acids*, Barak, Z.J.M., Chipman, D.M., Schloss, J.V. (eds) VCH Publishers, Weinheim, Germany, 1990.
Risse, B. et al, *Protein Sci.* 1: 1699, 1992.
Risse, B. et al., *Protein Sci.*, 1:1710, 1992.
Singh, B.K., & Schmitt, G.K. (1989), *FEBS Letters*, 258: 113.
Singh, B.K. et al. (1989) In: *Prospects for Amino Acid Biosynthesis Inhibitors in Crop Protection and Pharmaceutical Chemistry*, (Lopping, L.G., et al., eds., BCPC Monograph p. 87.
Muller et al., *Science* 259:965, 1993.
Holley et al., *Proc.Natl.Acad.Sci.USA* 86:152, 1989.
Needleman et al, *J. Mol. Biol.* 48:443, 1970.
M.O. Dayhoff, RM Schwartz & BC Orcutt "Atlas of Protein Sequence and Structure" vol. 5 suppl. 3 pp. 345–362, 1978.
Lam, et al., *Science* 263:380, 1994.
Thompson, et al., *J. Med. Chem.*, 37:3100, 1994.
B. Jenes et al., and S.W. Ritchie et al. In *Transgenic Plants, vol. 1, Engineering and Utilization*, ed. S.–D. Kung, R. Wu, Academic Press, Inc., Harcourt Brace Jovanovich 1993.
L. Mannonen et al., *Critical Reviews in Biotechnology*, 14:287–310, 1994.
Smith et al., *Gene* 67:31–40, 1988.
Singh et al. *Anal. Biochem.* 171:173–179, 1988.
Higuchi, R., Recombinant PCR, In M.A. Innis, et al., eds, *PCR Protocols: A Guide to Methods and Applications*, Academic Press, pp. 177–183, 1990.
Swanson et al., *Theor. Appl.Genet.*, 78:525–530, 1989.
Frame et al., *The Plant Journal*, 6:941–948, 1994.
Haughn et al., *Mol Gen Genet*, vol. 204:430–434, 1986.
Stidham, *Weed Science*, vol. 39:428–434, 1991.
Mosimann et al. "A critical assessment of comparative molecular modeling of tertiary structure of protein" Proteins: Structure, Function and Genetics, 23 (3), 301–317, Nov. 1996.
Blundell et al. "Knowledge–based prediction of protein structures and design of novel molecule" Nature 326, 347–352, Mar. 26, 1987.
Hattori et al. "Multiple resistance to sulfonylureas and imidazolinones conferred by acetohydroxyacid synthase gene with separate mutations for selective resistance" *Mol. Gen. Genet.* 232, 167–173, 1992.
Yadav et al. "Single amino acid substitutions in the enzyme acetolactate synthase confer resistance to the herbicide sulfometuron methyl" Proc. Natl. Acad. Sci. USA 83, 4418–4422, 1986.
Bernasconi et al. "A naturally occurring point mutation confers broad range tolerance to herbicides that target acetolactate synthase" J. Biol. Chem. 270, 17381–17385, Jul. 21, 1995.
Sathasivan et al. "Nucleotide sequence of a mutant acetolactate synthase gene from an imidazolinone–resistant Arabidopsis thaliana var. Columbia" Nucl. Acids Res. 18, 2188, 1990.
Ott et al. "Rational molecular design and genetic engineering of herbicide resistant crops by structural modeling and site–directed mutagenesis of . . . " J. Mol. Biol. 263, 359–368, 1996.

*Primary Examiner*—Robert A. Wax
*Assistant Examiner*—Nashaat T. Nashed
*Attorney, Agent, or Firm*—Darby & Darby

[57] ABSTRACT

Disclosed herein are structure-based modelling methods for the preparation of acetohydroxy acid synthase (AHAS) variants, including those that exhibit selectively increased resistance to herbicides such as imidazoline herbicides and AHAS inhibiting herbicides. The invention encompasses isolated DNAs encoding such variants, vectors that include the DNAs, and methods for producing the variant polypeptides and herbicide resistant plants containing specific AHAS gene mutations. Methods for weed control in crops are also provided.

10 Claims, 21 Drawing Sheets

A ←————————————————————————→ A

*1    * GSAASPAMP*10 *MAPPATPLRP*20 *WGPTDPRKGA*
*60   *TRSPVIANHL*70 *FRHEQGEAFA*80 *ASGYARSSGR*
                   Arg128    Phe135
*120  *AITGQVPRRM*130*IGTDAFQETP*140*IVEVTRSITK*
*180  *LVDIPKDIQQ*190*QMAVPVWDKP*200*MSLPGYIARL*
*240  *ARSGEELRRF*250*VELTGIPVTT*260*TLMGLGNFPS*
*300  *GVRFDDRVTG*310*KIEAFASRAK*320*IVHVDIDPAE*
*360  *SKKSFDFGSW*370*NDELDQQKRE*380*FPLGYKTSNE*
*420  *WAAQYYTYKR*430*PRQWLSSAGL*440*GAMGFGLPAA*
*480  *IRIENLPVKV*490*FVLNNQHLGM*500*VVQWEDRFYK*
*540  *PAVRVTKKNE*550*VRAAIKKMLE*560*TPGPYLLDII*

```
        Met53
 30  *DILVESLERC*40  *GVRDVFAYPG*50  *GASMEIHQAL
 90  *VGVCIATSGP*100 *GATNLVSALA*110 *DALLDSVPMV
150  *HNYLVLDVDD*160 *IPRVVQEAFF*170 *LASSGRPGPV
210  *PKPPATELLE*220 *QVLRLVGESR*230 *RPVLYVGGGC
270  *DDPLSLRMLG*280 *MHGTVYANYA*290 *VDKADLLLAL
330  *IGKNKQPHVS*340 *ICADVKLALQ*350 *GMNALLEGST
390  *EIQPQYAIQV*400 *LDELTKGEAI*410 *IGTGVGQHQM
450  *AGASVANPGV*460 *TVVDIDGDGS*470 *FLMNVQELAM
510  *ANRAHTYLGN*520 *PENESEIYPD*530 *FVTIAKGFNI
570  *VPHQEHVLPM*580 *IPSGGAFKDM*590 *ILDGDGRTVY
```

FIG. 2a

```
POX         *                *                 *24  *   TNILAGA*31   *AVIKVLEAWG*41   *VDHLYGIPGG*51  *SINSIMDALS
                                                    |||||||         ||||||||||       ||  |||||||      || |||||||
AHAS_pred *1   *GSAASPAMPM*11  *APPATPLRPW*21   *GPTDPRKGAD*31   *ILVESLERCG*41   *VRDVFAYPGG*51  *ASMEIHQALT POX       *61  *AERDRIHYIQ*71  *VRHEEVGAMA*81   *AAADAKLTGK*91   *IGVCFGSAGP*101 *GGTHLMNGLY*111 *DAREDHVPVL
               |  |||||||      |||||||||        |||  |||||       |||  |||||      |||   ||||     |||  |||
AHAS_pred *61  *RS PVIANHL*70  *FRHEQGEAFA*80   *ASGYARSSGR*90   *VGVCIATSGP*100 *GATNLVSALA*110 *DALLDSVPMV POX       *121 *ALIGQFGTTG*131 *MNMDTFQEMN*141 *ENPIYADVAD*151 *YNVTAVNAAT*161 *LPHVIDEAIR*171 *RAYAHQ GVA
               |||||||||       |||||||         | ||| ||||      ||| |||||      ||||||||||      ||||||
AHAS_pred *120 *AITGQVPRRM*130 *IGTDAFQETP*140 *IVEVTRSITK*150 *HNYLVLDVDD*160 *IPRVVQEAFF*170 *LASSGRPGPV POX       *180 *VVQIPVDLP  *189 *WQQISAEDWY*199 *ASANN  YQT*207 *PLLPEPDVQA*217 *VTRLTQTLLA*227 *AERPLIYYGI
               ||||||||         ||||                        ||||||||         |    |  ||       |||||
AHAS_pred *180 *LVDIPKDIQ  *189 *QQMAVPVWD *198 *KPMSLPGYIA*208 *RLPKPPATEL*218 *LEQVLRLVGE*228 *SRRPVLYVGG POX       *237 *GARKAGKELE*247 *QLSKTLKIPL*257 *MSTYPAKGIV*267 *ADRYPAYLGS*277 *ANRVAQKPAN*287 *EALAQADVVL
               ||  ||||||      ||||  |||       |   |||          ||| |||          |||||         |||||||
AHAS_pred *238 *GCARSGEELR*248 *RFVELTGIPV*258 *TTTLMGLGNF*268 *PSDDPLSLRM*278 *LGMHGTVYAN*288 *YAVDKADLLL
```

```
POX        *297*FVGNNY    PF*305*AEVSKAFKNT*315*RYFLQIDIDP*325*AKLGKRHKTD*335*IAVLAD    A*342*QKTLAAILAQ
                          ||| ||         ||||||||||        ||||||||||         || ||     ||||||||||||
AHAS_pred  *298*ALGVRFDDRV*308*TGKIEAFASR*318*AKIVHVDIDP*328*AEIGKNKQPH*338*VSICADVKLA*348*LQGMNALLEG POX        *352*VSEREST    *359*PWWQANLANV*369*KNWRAYLASL*379*EDKQEGPLQA*389*YQVLRAVNKI*399*AEPDAIYSID
                ||||||          |||| ||         |||         ||  |          ||||||||        ||||||||||
AHAS_pred  *358*STSKKSFDFG*368*SWNDELDQQK*378*REFPLGYKTS*388*NEE       IQP*394*QYAIQVLDEL*404*TKGEAIIGTG POX        *409*VGDINLNANR*419*HLKLTPSNRH*429*ITSNLFATMG*439*VGIPGAIAAK*449*LNYPERQVFN*459*LAGDGASMT
                ||||||  |        |||| ||         |||  |        ||| ||||||        ||||||||||       |||| ||
AHAS_pred  *414*VGQHQMWAAQ*424*YYTYKRPRQW*434*LSSAGLGAMG*444*FGLPAAAGAS*454*VANPGVTVVD*464*IDGDGSFLMN POX        *469*MQDLVTQVQY*479*HLPVINVVFT*489*NCQYGFIKDE*499*QEDTNQNDFI*509*GVEFNDID   F*518*SKIADGVHMQ
                |||        ||        |          ||  |           |||  |           |||  |||         |||  ||||||
AHAS_pred  *474*VQELAMIRIE*484*NLPVKVFVLN*494*NQHLGMVVQW*504*EDRFYKANRA*514*HTYLGNPENE*524*SEIYPDFVTI POX        *528*AFRVNKIEQL*538*PDVFEQAKAI*548*AQHEPVLIDA*558*VITGDRPLPA*568*EKLRLDSAMS*578*SAADIEAFKQ
                |     ||||      |   ||||       |||       ||||    |||||||         ||||||||         ||  ||||||
AHAS_pred  *534*AKGFNIPAVR*544*VTKKNEVRAA*554*IKKMLETPGP*564*YLLDIIVPHQ*574*EHVLPMIPSG*584*GAFKDMILDG POX        *588*RYEAQDLQPL*598*STYLKQFGLD*608*D
                |||||                                 *     *
AHAS_pred  *594*DGRTVY         *        *
```

```
            1                                                          50
Pac751      ..........  ..........  ..........  ..........  ..........
Maizeals2   ..........  ..........  ..........  ..........  MATAAAAS
Maizeals1   ..........  ..........  ..........  ..........  MATAATAA  TALTGATTAA
Tobac1      MAAA...APS  PSSSAFSKTL  SPSSSTSSTL  ..........  LPRSTFPFPH  AALTGATTAT
Tobac2      MAAA...AAA  PSPS.FSKTL  SSSSSKSSTL  ..........  LPRSTFPFPH  HPHKTTPPPL
Athcsr12    MAAATTTTTT  SSSISFSTKP  SPSSSKSPLP  ..........  ISRFSLPFSL  HPHKTTPPPL
Bnaal3      MAAA...TS   SSPISLTAKP  ...SSKSPLP  ..........  ISRFSLPFSL  NPNKSSSSSR
Bnaal2      .......M    ASFSFFGTIP  S....SPTK   ..........  ASVFSLPVSV  TPQKPSSRLH
Consensus   MAAA---ATS  -S--SSFS--P  SPSSSKSPT-  ..........  -SRFTLPFS-  TTLPSFPRRR
                                                                        TPLK---P---

51                                                         100
Pac751      ..........  .GSAASPAMP  MAPPATPLRP  WGPTDPRKGA
Maizeals2   PKARRRAHLL  ATRRALAAPI  RCSAASPAMP  MAPPATPLRP  WGPTDPRKGA
Maizeals1   PKSRRRAHHL  ATRRALAAPI  RCSALSRATP  TAPPATPLRP  WGPNEPRKGS
Tobac1      HLTHTHIHIH  SQRRRFTISN  VISTNQKVSQ  TEKTETFVSR  FAPDEPRKGS
Tobac2      HLTPT..HIH  SQRRRFTISN  VISTTQKVSE  TQKAETFVSR  FAPDEPRKGS
Athcsr12    RRGIKSSSPS  SISAVLNTTT  NVTTTPSPTK  PTKPETFISR  FAPDQPRKGA
Bnaal3      R........PL AISAVLNSPV  NV...APEK   TDKIKTFISR  YAPDEPRKGA
Bnaal2      ........AT  RVSVSANSKK  DQDRTAS..R  RENPSTFSSK  YAPNVPRSGA
Consensus   --TR-RAH-L  -IRR-LN-PI  --S-TS-A-P  T-KP-TF-SR  -APDEPRKGA
```

```
           101
Pac751     DILVESLERC GVRDVFAYPG GASMEIHQAL TRSPVIANHL FRHEQGEAFA
Maizeals2  DILVESLERC GVRDVFAYPG GASMEIHQAL TRSPVIANHL FRHEQGEAFA
Maizeals1  DILVEALERC GVRDVFAYPG GASMEIHQAL TRSPVIANHL FRHEQGEAFA
Tobac1     DVLVEALERE GVTDVFAYPG GASMEIHQAL TRSSIIRNVL PRHEQGGVFA
Tobac2     DVLVEALERE GVTDVFAYPG GASMEIHQAL TRSSIIRNVL PRHEQGGVFA
Athcsr12   DILVEALERQ GVETVFAYPG GASMEIHQAL TRSSSIRNVL PRHEQGGVFA
Bnaal3     DILVEALERQ GVETVFAYPG GASMEIHQAL TRSSTIRNVL PRHEQGGVFA
Bnaal2     DILVEALERQ GVDVVFAYPG GASMEIHQAL TRSNTIRNVL PRHEQGIFA
Consensus  DILVEALER- GV-DVFAYPG GASMEIHQAL TRSSVIRNVL PRHEQGGVFA
                                           ↑
                              EQUIVALENT TO MAIZE MET 53

151                                                 200
Pac751     ASGYARSSGR VGVCIATSGP GATNLVSALA DALLDSVPMV AITGQVPRRM
Maizeals2  ASGYARSSGR VGVCIATSGP GATNLVSALA DALLDSVPMV AITGQVPRRM
Maizeals1  ASAYARSSGR VGVCIATSGP GATNLVSALA DALLDSVPMV AITGQVPRRM
Tobac1     AEGYARATGF PGVCIATSGP GATNLVSGLA DALLDSVPIV AITGQVPRRM
Tobac2     AEGYARATGF PGVCIATSGP GATNLVSGLA DALLDSVPIV AITGQVPRRM
Athcsr12   AEGYARSSGK PGICIATSGP GATNLVSGLA DALLDSVPLV AITGQVPRRM
Bnaal3     AEGYARSSGK PGICIATSGP GATNLVSGLA DAMLDSVPLV AITGQVPRRM
Bnaal2     AEGYARSSGK PGICIATSGP GAMNLVSGLA DALFDSVPLI AITGQVPRRM
Consensus  AEGYARSSG- PGVCIATSGP GATNLVSGLA DALLDSVP-V AITGQVPRRM
                                                              ↑
                              EQUIVALENT TO MAIZE ARG 128
```

FIG. 5c

```
            EQUIVALENT TO MAIZE PHE 135
             201              ↓
Pac751       IGTDAFQETP  IVEVTRSITK  HNYLVLDVDD  IPRVVQEAFF  LASSGRPGPV
Maizeals2    IGTDAFQETP  IVEVTRSITK  HNYLVLDVDD  IPRVVQEAFF  LASSGRPGPV
Maizeals1    IGTDAFQETP  IVEVTRSITK  HNYLVLDVDD  IPRVVQEAFF  LASSGRPGPV
Tobac1       IGTDAFQETP  IVEVTRSITK  HNYLVMDVED  IPRVVREAFF  LARSGRPGPV
Tobac2       IGTDAFQETP  IVEVTRSITK  HNYLVMDVED  IPRVVREAFF  LARSGRPGPI
Athcsr12     IGTDAFQETP  IVEVTRSITK  HNYLVMDVED  IPRVVREAFF  LARSGRPGPV
Bnaal3       IGTDAFQETP  IVEVTRSITK  HNYLVMDVDD  IPRIIEEAFF  LATSGRPGPV
Bnaal2       IGTMAFQETP  VVEVTRTITK  HNYLVMEVDD  IPRIVREAFF  LATSVRPGPV
Consensus    IGTDAFQETP  IVEVTRSITK  HNYLVMDVDD  IPRVVQEAFF  LA-SGRPGPV 251                                              300
Pac751       LVDIPKDIQQ  QMAVPVWDKP  MSLPGYIARL  PKPPATELLE  QVLRLVGESR
Maizeals2    LVDIPKDIQQ  QMAVPVWDKP  MSLPGYIARL  PKPPATELLE  QVLRLVGESR
Maizeals1    LVDIPKDIQQ  QMAVPAWDTP  MSLPGYIARL  PKPPATEFLE  QVLRLVGESR
Tobac1       LIDVPKDIQQ  QLVIPDWDQP  MRLPGYMSRL  PKLPNEMLLE  QIVRLISESK
Tobac2       LIDVPKDIQQ  QLVIPDWDQP  MRLPGYMSRL  PKLPNEMLLE  QIVRLISESK
Athcsr12     LVDVPKDIQQ  QLAIPNWEQA  MRLPGYMSRM  PKPPEDSHLE  QIVRLISESK
Bnaal3       LVDVPKDIQQ  QLAIPNWDQP  MRLPGYMSRL  PQPPEVSQLG  QIVRLISESK
Bnaal2       LIDVPKDVQQ  QFAIPNWEQP  MRLPLYMSTM  PKPKVSHLE   QILRLVSESK
Consensus    LVDVPKDIQQ  QLAIPNWDQP  MRLPGYMSRL  PKPPA--LLE  QI-RL-SESK
```

FIG. 5d

```
              301
Pac751        RPVLYVGGGC ARSGEELRRF VELTGIPVTT TLMGLGNFPS DD.PLSLRML
Maizeals2     RPVLYVGGGC AASGEELRRF VELTGIPVTT TLMGLGNFPS DD.PLSLRML
Maizeals1     RPVLYVGGGC AASGEELCRF VELTGIPVTT TLMGLGNFPS DD.PLSLRML
Tobac1        KPVLYVGGGC SQSSEDLRRF VELTGIPVAS TLMGLGAFPT GD.ELSLSML
Tobac2        KPVLYVGGGC SQSSEELRRF VELTGIPVAS TLMGLGAFPT GD.ELSLSML
Athcsr12      KPVLYVGGGC LNSSDELGRF VELTGIPVAS TLMGLGSYPC DD.ELSLHML
Bnaal3        RPVLYVGGGS LNSSEELGRF VELTGIPVAS TLMGLGSYPC ND.ELSLQML
Bnaal2        RPVLYVGGGC LNSSEELRRF VELTGIPVAS TFMGLGSYPC DDEEFSLQML
Consensus     RPVLYVGGGC -NSSEELRRF VELTGIPVAS TLMGLG-FP- DD-ELSLRML
                                                                     350

351
Pac751        GMHGTVYANY AVDKADLLLA LGVRFDDRVT GKIEAFASRA KIVHVDIDPA
Maizeals2     GMHGTVYANY AVDKADLLLA LGVRFDDRVT GKIEAFASRA KIVHVDIDPA
Maizeals1     GMHGTVYANY AVDKADLLLA FGVRFDDRVT GKIEAFAGRA KIVHIDIDPA
Tobac1        GMHGTVYANY AVDSSDLLLA FGVRFDDRVT GKLEAFASRA KIVHIDIDSA
Tobac2        GMHGTVYANY AVDSSDLLLA FGVRFDDRVT GKLEAFASRA KIVHIDIDSA
Athcsr12      GMHGTVYANY AVEHSDLLLA FGVRFDDRVT GKLEAFASRA KIVHIDIDSA
Bnaal3        GMHGTVYANY AVEHSDLLLA FGVRFDDRVT GKLEAFASRA KIVHIDIDSA
Bnaal2        GMHGTVYANY AVEYSDLLLA FGVRFDDRVT GKLEAFASRA KIVHIDIDST
Consensus     GMHGTVYANY AVDKSDLLLA FGVRFDDRVT GKLEAFASRA KIVHIDIDSA
                                                                     400
```

FIG. 5e

```
              401
Pac751        EIGKNKQPHV  SICADVKLAL  QGMNALLEGS  TSKKSFDFGS  WNDELDQQKR
Maizeals2     EIGKNKQPHV  SICADVKLAL  QGMNALLEGS  TSKKSFDFGS  WNDELDQQKR
Maizeals1     EIGKNKQPHV  SICADVKLAL  QGMNTLLEGS  TSKKSFDFGS  WHDELDQQKR
Tobac1        EIGKNKQPHV  SICADIKLAL  QGLNSILESK  EGKLKLDFSA  WRQELTEQKV
Tobac2        EIGKNKQPHV  SICADIKLAL  QGLNSILESK  EGKLKLDFSA  WRQELTVQKV
Athcsr12      EIGKNKTPHV  SVCGDVKLAL  QGMNKVLENR  AEELKLDFGV  WRNELNVQKQ
Bnaal3        EIGKNKTPHV  SVCGDVKLAL  QGMNKVLENR  AEELKLDFGV  WRSELSEQKQ
Bnaal2        EIGKNKTPHV  SVCCDVQLAL  QGMNEVLENR  RD..VLDFGE  WRCELNEQRL
Consensus     EIGKNKQPHV  SICADVKLAL  QGMN-VLE--  T-KLKLDFGS  WRDELD-QKR 451                                              500
Pac751        EFPLGYKTSN  EEIQPQYAIQ  VLDELTKGEA  IIGTGVGQHQ  MWAAQYYTYK
Maizeals2     EFPLGYKTSN  EEIQPQYAIQ  VLDELTKGEA  IIGTGVGQHQ  MWAAQYYTYK
Maizeals1     EFPLGYKIFN  EEIQPQYAIQ  VLDELTKGEA  IIATGVGQHQ  MWAAQYYTYK
Tobac1        KHPLNFKTFG  DAIPPQYAIQ  VLDELTNGNA  IISTGVGQHQ  MWAAQYYKYR
Tobac2        KYPLNFKTFG  DAIPPQYAIQ  VLDELTNGSA  IISTGVGQHQ  MWAAQYYKYR
Athcsr12      KFPLSFKTFG  EAIPPQYAIK  VLDELTDGKA  IISTGVGQHQ  MWAAQFYNYK
Bnaal3        KFPLSFKTFG  EAIPPQYAIQ  VLDELTQGKA  IISTGVGQKA  MWAAQFYKYR
Bnaal2        KFPLRYKTFG  EEIPPQYAIQ  LLDELTDGKA  IITTGVGQHQ  MWAAQFYRFK
Consensus     KFPLG-KTFG  E-IPPQYAIQ  VLDELTKG-A  IISTGVGQHQ  MWAAQYY-YK
```

FIG. 5f

```
            501                                                          550
Pac751      RPRQWLSSAG  LGAMGFGLPA  AAGASVANPG  VTVVDIDGDG  SFLMNVQELA
Maizeals2   RPRQWLSSAG  LGAMGFGLPA  AAGASVANPG  VTVVDIDGDG  SFLMNVQELA
Maizeals1   RPRQWLSSAG  LGAMGFGLPA  AAGAAVANPG  VTVVDIDGDG  SFLMNIQELA
Tobac1      KPRQWLTSGG  LGAMGFGLPA  AIGAAVGRPD  EVVVDIDGDG  SFIMNVQELA
Tobac2      KPRQWLTSGG  LGAMGFGLPA  AIGAAVGRPD  EVVVDIDGDG  SFIMNVQELA
Athcsr12    KPRQWLSSGG  LGAMGFGLPA  AIGASVANPD  AIVVDIDGDG  SFIMNVQELA
Bnaal3      KPRQWLSSSG  LGAMGFGLPA  AIGASVANPD  AIVVDIDGDG  SFIMNIQELA
Bnaal2      KPRQWLSSGG  LGAMGFGLPA  AMGAAIANPG  AVVVDIDGDG  SFIMNIQELA
Consensus   KPRQWLSSGG  LGAMGFGLPA  AIGA-VANP-  -VVVDIDGDG  SFIMNVQELA 551                                                          600
Pac751      MIRIENLPVK  VFVLNNQHLG  MVVQWEDRFY  KANRAHTYLG  NPENESEIYP
Maizeals2   MIRIENLPVK  VFVLNNQHLG  MVVQWEDRFY  KANRAHTYLG  NPENESEIYP
Maizeals1   MIRIENLPVK  VFVLNNQHLG  MVVQWEDRFY  KANRAHTFLG  NPENESEIYP
Tobac1      TIKVENLPVK  IMLLNNQHLG  MVVQWEDRFY  KANRAHTYLG  NPSNEAEIFP
Tobac2      TIKVENLPVK  IMLLNNQHLG  MVVQWEDRFY  KANRAHTYLG  NPSNEAEIFP
Athcsr12    TIRVENLPVK  VLLLNNQHLG  MVMQWEDRFY  KANRAHTFLG  DPAQEDEIFP
Bnaal3      TIRVENLPVK  ILLLNNQHLG  MVMQWEDRFY  KANRAHTFLG  DPARENEIFP
Bnaal2      TIRVENLPVK  VLLINNQHLG  MVLQWEDHFY  AANRADSFLG  DPANPEAVFP
Consensus   TIRVENLPVK  V-LLNNQHLG  MVVQWEDRFY  KANRAHTYLG  NP-NESEIFP
```

FIG. 5g

```
            601
Pac751      DFVTIAKGFN IPAVRVTKKN EVRAAIKKML ETPGPYLLDI IVPHQEHVLP
Maizeals2   DFVTIAKGFN IPAVRVTKKN EVRAAIKKML ETPGPYLLDI IVPHQEHVLP
Maizeals1   DFVAIAKGFN IPAVRVTKKS EVHAAIKKML EAPGPYLLDI IVPHQEHVLP
Tobac1      NMLKFAEACG VPAARVTHRD DLRAAIQKML DTPGPYLLDV IVPHQEHVLP
Tobac2      NMLKFAEACG VPAARVTHRD DLRAAIQKML DTPGPYLLDV IVPHQEHVLP
Athcsr12    NMLLFAAACG IPAARVTKKA DLREAIQTML DTPGPYLLDV ICPHQEHVLP
Bnaal3      NMLQFAGACG IPAARVTKKE ELREAIQTML DTPGPYLLDV ICPHQEHVLP
Bnaal2      DMLLFAASCG IPAARVTRRE DLREAIQKML DTPGPFLLDV VCPHQDHVLP
Consensus   -ML-FAKACG IPAARVTKK- -LRAAIQKML DTPGPYLLDV IVPHQEHVLP 651                                            673
Pac751      MIPSGGAFKD MILDGDGRTV Y...
Maizeals2   MIPSGGAFKD MILDGDGRTV Y*..
Maizeals1   MIPSGGAFKD MILDGDGRTV Y*..
Tobac1      MIPSGGAFKD VITEGDGRSS Y*..
Tobac2      MIPSGGAFKD VITEGDGRSS Y*..
Athcsr12    MIPNGGTFND VITEGDGRIK Y*E
Bnaal3      MIPSGGTFKD VITEGDGRTK Y*..
Bnaal2      LIPSGGTFKD IIV*...... ....
Consensus   MIPSGGAFKD VITEGDGRTV Y--
```

FIG. 5h

Pac751 - maize als2 AHAS isozyme as expressed from the pAC751 E. coli expression vector (same as figure 1)
Maizeals2 - maize als2 AHAS isozyme (plant)
Maizeals1 - maize als1 AHAS isozyme (plant)
Tobac1 - tobacco AHAS SuRA isozyme (plant)
Tobac2 - tobacco AHAS SuRB isozyme (plant)
Athcsr12 - Arabidopsis thaliana Csr 1.2 AHAS gene (plant)
Bnaal3 - Brassica napus AHAS III isozyme (plant)
Bnaal2 - Brassica napus AHAS II isozyme (plant)

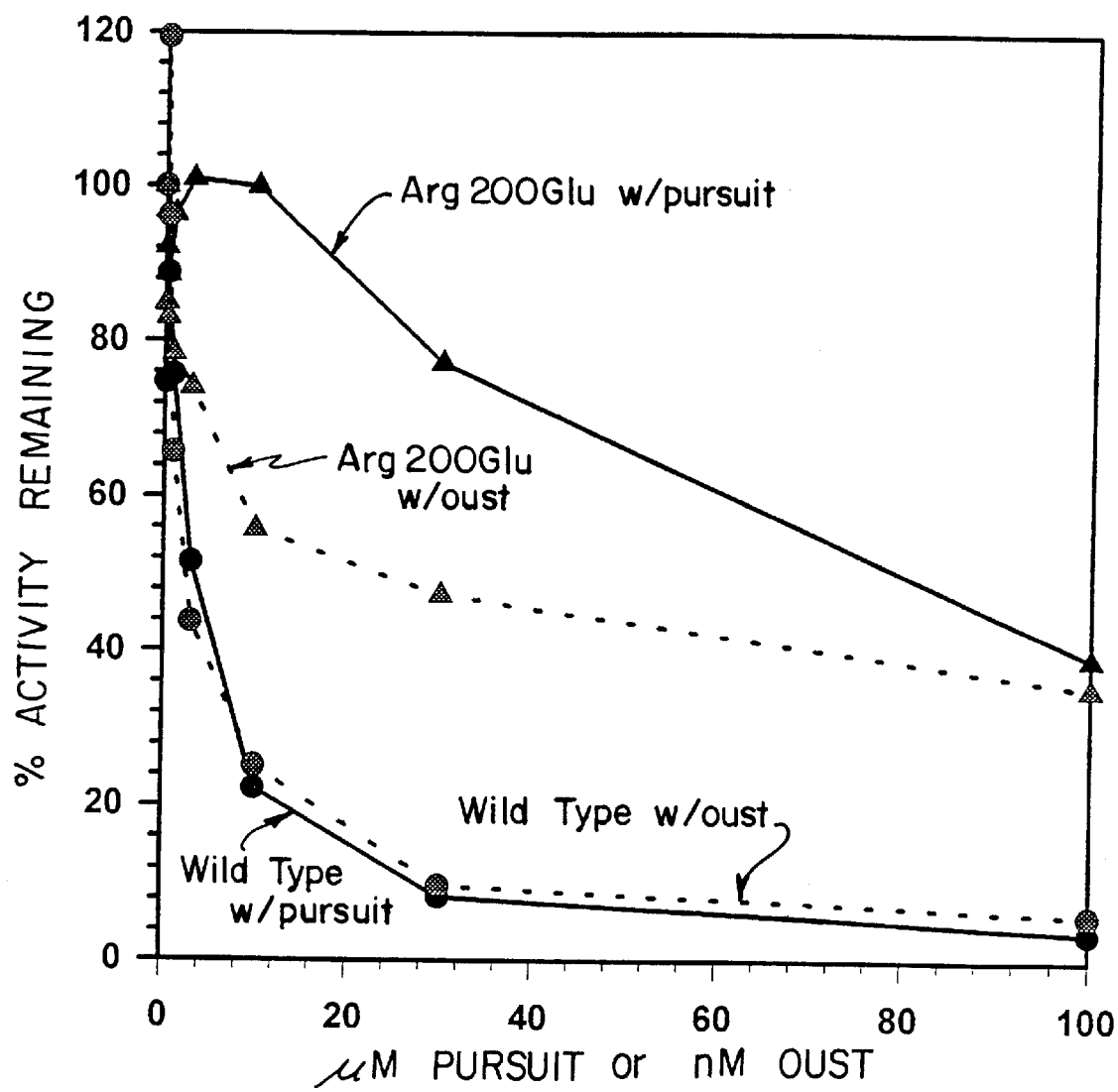

STRUCTURE BASED DESIGNED HERBICIDE RESISTANT PRODUCTS

FIELD OF THE INVENTION

This invention pertains to structure-based modelling and design of variants of acetohydroxy acid synthase (AHAS) that are resistant to imidazolinones and other herbicides, the AHAS inhibiting herbicides, AHAS variants themselves, DNA encoding these variants, plants expressing these variants, and methods of weed management.

BACKGROUND OF THE INVENTION

Acetohydroxy acid synthase (AHAS) is an enzyme that catalyzes the initial step in the biosynthesis of isoleucine, leucine, and valine in bacteria, yeast, and plants. For example, the mature AHAS from Zea Mays is approximately a 599-amino acid protein that is localized in the chloroplast (see FIG. 1). The enzyme utilizes thiamine pyrophosphate (TPP) and flavin adenine dinucleotide (FAD) as cofactors and pyruvate as a substrate to form acetolactate. The enzyme also catalyzes the condensation of pyruvate and 2-ketobutyrate to form acetohydroxybutyrate. AHAS is also known as acetolactate synthase or acetolactate pyruvate lyase (carboxylating), and is designated EC 4.1.3.18. The active enzyme is probably at least a homodimer. Ibdah et al. (*Protein Science*, 3:479-S, 1994), in an abstract, disclose one model for the active site of AHAS.

A variety of herbicides including imidazolinone compounds such as imazethapyr (PURSUIT®—American Cyanamid Company—Wayne, N.J.), sulfonylurea-based compounds such as sulfometuron methyl (OUST®—E. I. du Pont de Nemours and Company-Wilmington, Del.), triazolopyrimidine sulfonamides (Broadstrike™—Dow Elanco; see Gerwick, et al., *Pestic. Sci.* 29:357–364, 1990), sulfamoylureas (Rodaway et al., *Mechanisms of Selectively of Ac* 322,140*in Paddy Rice, Wheat and Barley*, Proceedings of the Brighton Crop Protection Conference-Weeds, 1993), pyrimidyl-oxy-benzoic acids (STABLE®—Kumiai Chemical Industry Company, E. I. du Pont de Nemours and Company; see, The Pesticide Manual 10th Ed. pp. 888–889, Clive Tomlin, Ed., British Crop Protection Council, 49 Downing Street, Farmham, Surrey G49 7PH, UNITED KINGDOM), and sulfonylcarboximides (Alvarado et al., U.S. Pat. No. 4,883,914) act by inhibiting AHAS enzymatic activity. (See, Chaleff et al., *Science* 224:1443, 1984; LaRossa et al., *J.Biol. Chem.* 259:8753, 1984; Ray, *Plant Physiol.* 75:827, 11984; Shaner et al., *Plant Physiol.* 76:545, 1984). These herbicides are highly effective and environmentally benign. Their use in agriculture, however, is limited by their lack of selectivity, since crops as well as undesirable weeds are sensitive to the phytotoxic effects of these herbicides.

Bedbrook et al., U.S. Pat. Nos. 5,013,659, 5,141,870, and 5,378,824, disclose several sulfonylurea resistant AHAS variants. However, these variants were either obtained by mutagenizing plants, seeds, or cells and selecting for herbicide-resistant mutants, or were derived from such mutants. This approach is unpredictable in that it relies (at least initially) on the random chance introduction of a relevant mutation, rather than a rational design approach based on a structural model of the target protein.

Thus, there is still a need in the art for methods and compositions that provide selective wide spectrum and/or specific herbicide resistance in cultivated crops. The present inventors have discovered that selective herbicide resistant variant forms of AHAS and plants containing the same can be prepared by structure-based modelling of AHAS against pyruvate oxidase (POX), identifying an herbicide binding pocket or pockets on the AHAS model, and designing specific mutations that alter the affinity of the herbicide for the binding pocket. These variants and plants are not inhibited or killed by one or more classes of herbicides and retain sufficient AHAS enzymatic activity to support crop growth.

BRIEF DESCRIPTION OF THE DRAWINGS

FIG. 1 is an illustration of a 600 amino acid sequence SEQ ID NO:1 corresponding to the approximately 599 amino acid sequence of acetohydroxy acid synthase (AHAS) from *Zea Mays* which is given as an example of a plant AHAS enzyme. The sequence does not include a transit sequence, and the extra glycine is vestigial from a thrombin cleavage site. Residues Met53, Arg128, and Phe135 are shown in bold.

FIG. 2 is an illustration of the alignment of the sequence of maize AHAS and pyruvate oxidase (POX) SEQ ID NO:2 from *Lactobacillus planarum.*

FIG. 3 is a schematic representation of the secondary structure of an AHAS subunit. Regular secondary structure elements, α-helices and β-sheets, are depicted as circles and ellipses, respectively, and are numbered separately for each of the three domains within a subunit. Loops and coiled regions are represented by black lines, with numbers representing the approximate beginnings and ends of the elements. The locations of cofactor binding sites and known mutation sites are indicated by octahedrons and stars, respectively.

FIG. 4 is an illustration of a computer-generated model of the active site of maize AHAS with imazethapyr (PURSUIT® herbicide) modeled into the binding pocket.

FIGS. 5*a*–5*d* are an illustration of the homology among AHAS amino acid sequences derived from different plant species. pAC 751 SEQ ID NO:3 is maize als 2 AHAS isozyme as expressed from the pAC 751 *E. Coli* expression vector as in FIG. 1; Maize als 2 SEQ ID NO:4 is the maize als 2 AHAS isozyme; Maize als 1 SEQ ID NO:5 is the maize als 1 AHAS isozyme; Tobac 1 SEQ ID NO:6 is the tobacco AHAS SuRA isozyme; Tobac 2 SEQ ID NO:7 is the tobacco AHAS SuRB isozyme; Athcsr 12 SEQ ID NO:8 is the *Arabidopsis thaliana* Csr 1.2 AHAS gene; Bnaal 3 SEQ ID NO:9 is the *Brassica napus* AHAS III isozyme; and Bnaal 2 SEQ ID NO:10 is the *Brassica napus* AHAS II isozyme.

pAC 751 and Maize als 2 are identical genes except that Maize als 2 starts at the beginning of the transit sequence and pAC 751 starts at the putative mature N-terminal site with an additional glycine at the N-terminal due to the thrombin recognition sequence in the pGEX-2T expression vector. The N-terminal glycine is not a natural amino acid at that position.

Amino acid sequence alignments of the AHAS proteins were generated by PILEUP (GCG Package—Genetics Computer Group, Inc., —University Research Park-Madison, Wis.). The consensus sequence was generated by PRETTY GCG Package.

FIG. 6 is a photographic illustration of an SDS-polyacrylamide gel stained for protein showing purification of maize AHAS. The lanes contain (from left to right): A, Molecular weight markers; B, Crude *E. coli* cell extract; C, Glutathione-agarose affinity purified preparation; D, Thrombin digest of the affinity purified preparation; E, Second pass through glutathione-agarose column and Sephacryl S-100 gel filtration.

FIG. 7 is a graphic illustration of the results of in vitro assays of the enzymatic activity of wild-type and mutant AHAS proteins in the absence and in the presence of increasing concentrations of imazethapyr (PURSUIT® herbicide). The Y axis represents the % of activity of the mutant enzyme, wherein the 100% value is measured in the absence of inhibitor.

FIG. 8 is a graphic illustration of the results of in vitro assays of the enzymatic activity of wild-type and mutant AHAS proteins in the absence and presence of increasing concentrations of sulfometuron methyl (OUST® herbicide). The Y axis represents the % of activity of the mutant enzyme, wherein the 100% value is measured in the absence of inhibitor.

FIG. 9 is a graphic illustration of in vitro assays of the enzymatic activity of wild-type Arabidopsis AHAS protein and the Met125Ile mutant Arabidopsis AHAS protein in the absence and presence of increasing concentrations of imazethapyr (PURSUIT® herbicide) and sulfometuron methyl (OUST® herbicide). The Y axis represents the % activity of the mutant enzyme, wherein the 100% value is measured in the absence of inhibitor.

FIG. 10 is a graphic illustration of in vitro assays of the enzymatic activity of wild-type Arabidopsis AHAS protein and Arg200Glu mutant Arabidopsis AHAS protein in the absence and presence of increasing concentrations of imazethapyr (PURSUIT® herbicide) and sulfometuron methyl (OUST® herbicide). The Y axis represents the % activity of the mutant enzyme, wherein the 100% value is measured in the absence of inhibitor.

SUMMARY OF THE INVENTION

The present invention provides a structure-based modelling method for the production of herbicide resistant AHAS variant protein. The method includes:
- (a) aligning a target AHAS protein on pyruvate oxidase template or an AHAS modelling equivalent thereof to derive the three-dimensional structure of the target AHAS protein;
- (b) modelling one or more herbicides into the three-dimensional structure to localize an herbicide binding pocket in the target AHAS protein;
- (c) selecting as a target for a mutation, at least one amino acid position in the target AHAS protein, wherein the mutation alters the affinity of at least one herbicide for the binding pocket;
- (d) mutating DNA encoding the target AHAS protein to produce a mutated DNA encoding a variant AHAS containing the mutation, such as, for example, at least one different amino acid, at the position; and
- (e) expressing the mutated DNA in a first cell, under conditions in which the variant AHAS containing the mutation, such as, for example, the different amino acid(s), at the position is produced.

The method further may include:
- (f) expressing DNA encoding wild-type AHAS protein parallel in a second cell;
- (g) purifying the wild-type and the variant AHAS proteins from the cells;
- (h) assaying the wild-type and the variant AHAS proteins for catalytic activity in conversion of pyruvate to acetolactate or in the condensation of pyruvate and 2-ketobutyrate to form acetohydroxybutyrate, in the absence and in the presence of the herbicide; and
- (i) repeating steps (c)–(h), wherein the DNA encoding the AHAS variant of step (e) is used as the AHAS-encoding DNA in step (c) until a first herbicide resistant AHAS variant protein is identified having:
  - (i) in the absence of the at least one herbicide,
    - (a) catalytic activity alone sufficient to maintain the viability of a cell in which it is expressed; or
    - (b) catalytic activity in combination with any herbicide resistant AHAS variant protein also expressed in the cell, which may be the same as or different than the first AHAS variant protein, sufficient to maintain the viability of a cell in which it is expressed;

wherein the cell requires AHAS activity for viability; and
  - (ii) catalytic activity that is more resistant to the at least one herbicide than is wild-type AHAS.

An alternate structure-based modelling method for the production of herbicide resistant AHAS variant protein is also provided. This method includes:
- (a) aligning a target AHAS protein on a first AHAS template derived from a polypeptide having the sequence of FIG. 1 or a functional equivalent thereof to derive the three-dimensional structure of the target AHAS protein;
- (b) modelling one or more herbicides into the three-dimensional structure to localize an herbicide binding pocket in the target AHAS protein;
- (c) selecting as a target for a mutation, at least one amino acid position in the target AHAS protein, wherein the mutation alters the affinity of at least one herbicide for the binding pocket;
- (d) mutating DNA encoding the target AHAS protein to produce a mutated DNA encoding a variant AHAS containing the mutation at the position; and
- (e) expressing the mutated DNA in a first cell, under conditions in which the variant AHAS containing the mutation at the position is produced.

This method can further include:
- (f) expressing DNA encoding wild-type AHAS protein in parallel in a second cell;
- (g) purifying the wild-type and the variant AHAS protein from the cells;
- (h) assaying the wild-type and the variant AHAS protein for catalytic activity in conversion of pyruvate to acetolactate or in the condensation of pyruvate and 2-ketobutyrate to form acetohydroxybutyrate, in the absence and in the presence of the herbicide; and
- (i) repeating steps (c)–(h), wherein the DNA encoding the AHAS variant of step (e) is used as the AHAS-encoding DNA in step (c) until a first herbicide resistant AHAS variant protein is identified having:
  - (i) in the absence of the at least one herbicide,
    - (a) catalytic activity alone sufficient to maintain the viability of a cell in which it is expressed; or
    - (b) catalytic activity in combination with any herbicide resistant AHAS variant protein also expressed in the cell, which may be the same as or different than the first AHAS variant protein, sufficient to maintain the viability of a cell in which it is expressed;

wherein the cell requires AHAS activity for viability; and
  - (ii) catalytic activity that is more resistant to the at least one herbicide than is wild-type AHAS.

In another alternate embodiment, the method includes:
- (a) aligning a target AHAS protein on a first AHAS template having an identified herbicide binding pocket and having the sequence of FIG. 1 or a functional equivalent thereof to derive the three-dimensional structure of the target AHAS protein;

(b) selecting as a target for a mutation, at least one amino acid position in the target AHAS protein, wherein the mutation alters the affinity of at least one herbicide for the binding pocket;

(c) mutating DNA encoding the target AHAS protein to produce a mutated DNA encoding a variant AHAS containing the mutation at the position; and (d) expressing the mutated DNA in a first cell, under conditions in which the variant AHAS containing the mutation at the position is produced.

This method can further include:

(e) expressing DNA encoding wild-type target AHAS protein in parallel in a second cell;

(f) purifying the wild-type and the variant AHAS protein from the cells;

(g) assaying the wild-type and the variant AHAS protein for catalytic activity in conversion of pyruvate to acetolactate or in the condensation of pyruvate and 2-ketobutyrate to form acetohydroxybutyrate, in the absence and in the presence of the herbicide; and (h) repeating steps (b)–(g), wherein the DNA encoding the AHAS variant of step (d) is used as the AHAS-encoding DNA in step (b) until a first herbicide resistant AHAS variant protein is identified having:

(i) in the absence of the at least one herbicide, (a) catalytic activity alone sufficient to maintain the viability of a cell in which it is expressed; or (b) catalytic activity in combination with any herbicide resistant AHAS variant protein also expressed in the cell, which may be the same as or different than the first AHAS variant protein, sufficient to maintain the viability of a cell in which it is expressed;

wherein the cell requires AHAS activity for viability; and (ii) catalytic activity that is more resistant to the at least one herbicide than is wild-type AHAS.

In preferred embodiments of the above methods, the catalytic activity in the absence of the herbicide is at least about 5% and most preferably is more than about 20% of the catalytic activity of the wild-type AHAS. Where the herbicide is an imidazolinone herbicide, the herbicide resistant AHAS variant protein preferably has:

(i) catalytic activity in the absence of the herbicide of more than about 20% of the catalytic activity of the wild-type AHAS;

(ii) catalytic activity that is relatively more resistant to the presence of imidazolinone herbicides compared to wild-type AHAS; and (iii) catalytic activity that is relatively more sensitive to the presence of sulfonylurea herbicides compared to imidazolinone herbicides.

The present invention further provides isolated DNA encoding acetohydroxy acid synthase (AHAS) variant proteins, the variant proteins comprising an AHAS protein modified by:

(i) substitution of at least one different amino acid residue at an amino acid residue of the sequence of FIG. 1 SEQ ID NO:1 selected from the group consisting of P48, G49, S52, M53, E54, A84, A95, T96, S97, G98, P99, G100, A101, V125, R127, R128, M129, I130, G131, T132, D133, F135, Q136, D186, I187, T259, T260, L261, M262, G263, R276, M277, L278, G279, H281, G282, T283, V284, G300, V301, R302, F303; D304, R306, V307, T308, G309, K310, I311, E312, A313, F314, A315, S316, R317, A318, K319, I320, E329, I330, K332, N333, K334, Q335, T404, G413, V414, G415, Q416, H417, Q418, M419, W420, A421, A422, L434, S435, S436, A437, G438, L439, G440, A441, M442, G443, D467, G468, S469, L471, N473, L477, M479, Q495, H496, L497, G498, M499, V501, Q502, Q504, D505, R506, Y508, K509, A510, N511, R512, A513, H514, T515, S524, H572, Q573, E574, H575, V576, L577, P578, M579, I580, P581, G583, G584, functional equivalents of any of the foregoing, and any combination of any of the foregoing;

(ii) deletion of up to 5 amino acid residues preceding, or up to 5 amino acid residues following at least one amino acid residue of the sequence of FIG. 1 selected from the group consisting of P48, G49, S52, M53, E54, A84, A95, T96, S97, G98, P99, G100, A101, V125, R127, R128, M129, I130, G131, T132, D133, F135, Q136, D186, I187, T259, T260, L261, M262, G263, R276, M277, L278, G279, H281, G282, T283, V284, G300, V301, R302, F303, D304, R306, V307, T308, G309, K310, I311, E312, A313, F314, A315, S316, R317, A318, K319, I320, E329, I330, K332, N333, K334, Q335, T404, G413, V414, G415, Q416, H417, Q418, M419, W420, A421, A422, L434, S435, S436, A437, G438, L439, G440, A441, M442, G443, D467, G468, S469, L471, N473, L477, M479, Q495, H496, L497, G498, M499, V501, Q502, Q504, D505, R506, Y508, K509, A510, N511, R512, A513, H514, T515, S524, H572, Q573, E574, H575, V576, L577, P578, M579, I580, P581, G583, G584, functional equivalents of any of the foregoing, and any combination of any of the foregoing;

(iii) deletion of at least one amino acid residue or a functional equivalent thereof between Q124 and H150 of the sequence of FIG. 1;

(iv) addition of at least one amino acid residue or a functional equivalent thereof between Q124 and H150 of the sequence of FIG. 1;

(v) deletion of at least one amino acid residue or a functional equivalent thereof between G300 and D324 of the sequence of FIG. 1;

(vi) addition of at least one amino acid residue or a functional equivalent thereof between G300 and D324 of the sequence of FIG. 1; or (vii) any combination of any of the foregoing.

In this numbering system, residue #2 corresponds to the putative amino terminus of the mature protein, i.e., after removal of a chloroplast targeting peptide.

The above modifications are directed to altering the ability of an herbicide, and preferably an imidazolinone-based herbicide, to inhibit the enzymatic activity of the protein. In a preferred embodiment, the isolated DNA encodes an herbicide-resistant variant of AHAS. Also provided are DNA vectors comprising DNA encoding these AHAS variants, variant AHAS proteins themselves, and cells, grown either in vivo or in vitro, that express the AHAS variants or comprise these vectors.

In another aspect, the present invention provides a method for conferring herbicide resistance on a cell or cells and particularly a plant cell or cells such as, for example, a seed. An AHAS gene, preferably the *Arabidopsis thaliana* AHAS gene, is mutated to alter the ability of an herbicide to inhibit the enzymatic activity of the AHAS. The mutant gene is cloned into a compatible expression vector, and the gene is transformed into an herbicide-sensitive cell under conditions in which it is expressed at sufficient levels to confer herbicide resistance on the cell.

Also contemplated are methods for weed control, wherein a crop containing an herbicide resistant AHAS gene according to the present invention is cultivated and treated with a weed-controlling effective amount of the herbicide.

Also disclosed is a structure-based modelling method for the preparation of a first herbicide which inhibits AHAS activity. The method comprises:

(a) aligning a target AHAS protein on pyruvate oxidase template or an AHAS modelling functional equivalent thereof to derive the three-dimensional structure of the target AHAS protein;

(b) modelling a second herbicide having AHAS inhibiting activity into the three-dimensional structure to derive the location, structure, or a combination thereof of an herbicide binding pocket in the target AHAS protein; and (c) designing a non-peptidic first herbicide which will interact with, and preferably will bind to, an AHAS activity inhibiting effective portion of the binding pocket, wherein the first herbicide inhibits the AHAS activity sufficiently to destroy the viability of a cell which requires AHAS activity for viability.

An alternative structure-based modelling method for the production of a first herbicide which inhibits AHAS activity, is also enclosed. The method comprises:

(a) aligning a target AHAS protein on a first AHAS template derived from a polypeptide having the sequence of FIG. 1 or a functional equivalent thereof, to derive the three-dimensional structure of the target AHAS protein;

(b) modelling a second herbicide having AHAS inhibiting activity into the three-dimensional structure to derive the location, structure, or a combination thereof of an herbicide binding pocket in the target AHAS protein; and (c) designing a non-peptidic first herbicide which will interact with, and preferably will bind to, an AHAS activity inhibiting effective portion of the binding pocket, wherein the first herbicide inhibits the AHAS activity sufficiently to destroy the viability of a cell which requires AHAS activity for viability.

Preferably in each method, the first herbicide contains at least one functional group that interacts with a functional group of the binding pocket.

DETAILED DESCRIPTION OF THE INVENTION

Figure 3A:
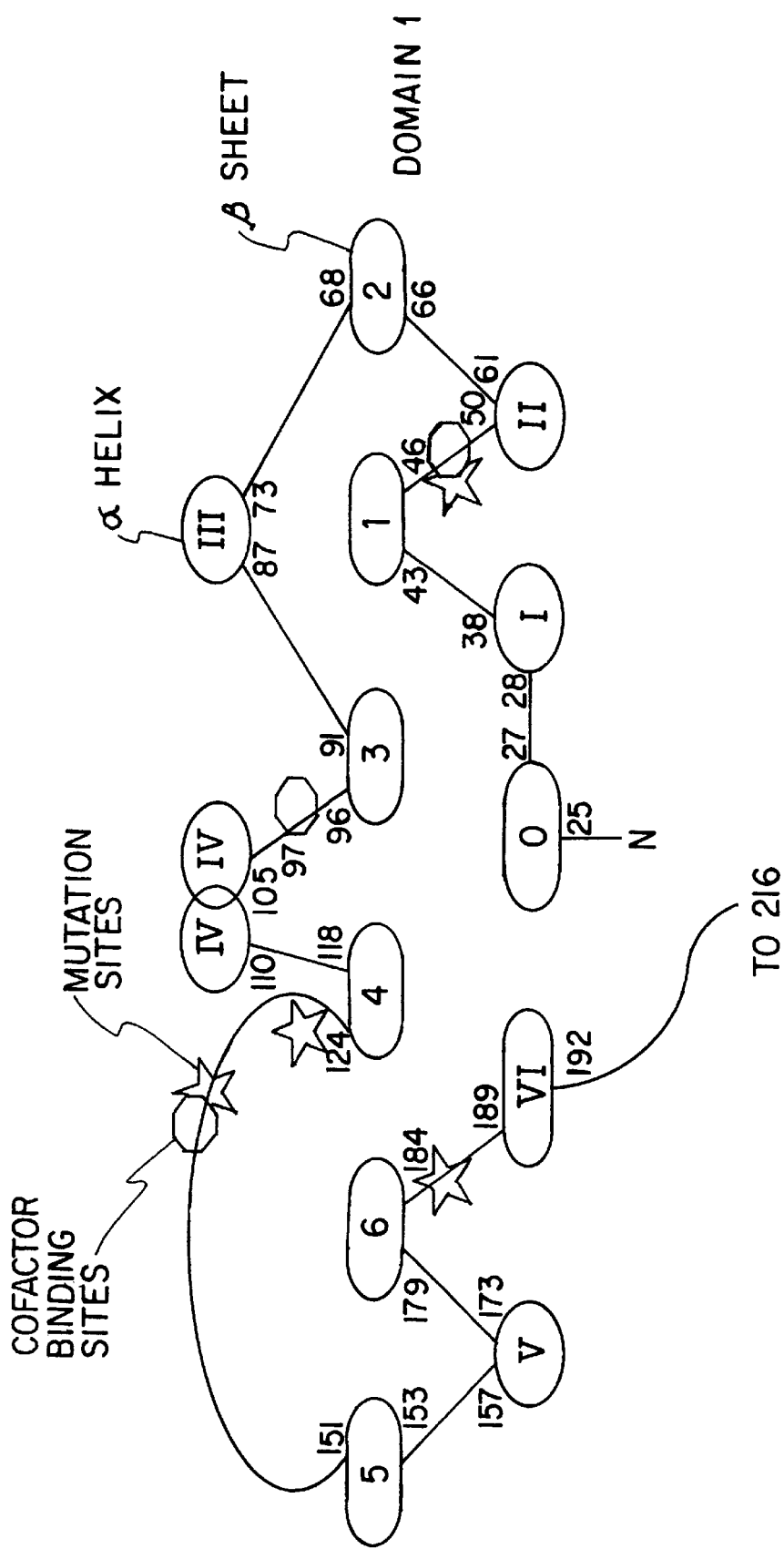

The present invention encompasses the rational design or structure-based molecular modelling of modified versions of the enzyme AHAS and AHAS inhibiting herbicides. These modified enzymes (AHAS variant proteins) are resistant to the action of herbicides. The present invention also encompasses DNAs that encode these variants, vectors that include these DNAs, the AHAS variant proteins, and cells that express these variants. Additionally provided are methods for producing herbicide resistance in plants by expressing these variants and methods of weed control. The DNA and the AHAS variants of the present invention were discovered in studies that were based on molecular modelling of the structure of AHAS.

Rational Structure-Based Design of AHAS Variants and AHAS Inhibiting Herbicides

Herbicide-resistant variants of AHAS according to the present invention are useful in conferring herbicide resistance in plants and can be designed with the POX model or AHAS modelling functional equivalents thereof, such as, for example, transketolases, carboligases, and pyruvate decarboxylase which have structural features similar to POX and/or AHAS, with an AHAS model such as a model having the sequence of FIG. 1 SEQ ID NO:1; or with a functional equivalent of the sequence of FIG. 1 including a variant modeled from a previous model. AHAS directed herbicides can be similarly modelled from these templates. A functional equivalent of an AHAS amino acid sequence is a sequence having substantial, i.e., 60–70%, homology, particularly in conserved regions such as, for example, a putative binding pocket. The degree of homology can be determined by simple alignment based on programs known in the art, such as, for example, GAP and PILEUP by GCG. Homology means identical amino acids or conservative substitutions. A functional equivalent of a particular amino acid residue in the AHAS protein of FIG. 1 is an amino acid residue of another AHAS protein which when aligned with the sequence of FIG. 1 by programs known in the art, such as, for example, GAP and PILEUP by GCG, is in the same position as the amino acid residue of FIG. 1.

Rational design steps typically include: (1) alignment of a target AHAS protein with a POX backbone or structure or an AHAS backbone or structure; (2) optionally, and if the AHAS backbone has an identified herbicide binding pocket, modelling one or more herbicides into the three-dimensional structure to localize an herbicide binding pocket in the target protein; (3) selection of a mutation based upon the model; (4) site-directed mutagenesis; and (5) expression and purification of the variants. Additional steps can include (6) assaying of enzymatic properties and (7) evaluation of suitable variants by comparison to the properties of the wild-type AHAS. Each step is discussed separately below.

1. Molecular Modelling

Molecular modelling (and particularly protein homology modelling) techniques can provide an understanding of the structure and activity of a given protein. The structural model of a protein can be determined directly from experimental data such as x-ray crystallography, indirectly by homology modelling or the like, or combinations thereof (See White, et al., *Annu. Rev. Biophys. Biomol. Struct.*, 23:349, 1994). Elucidation of the three-dimensional structure of AHAS provides a basis for the development of a rational scheme for mutation of particular amino acid residues within AHAS that confer herbicide resistance on the polypeptide.

Molecular modelling of the structure of *Zea mays* AHAS, using as a template the known X-ray crystal structure of related pyruvate oxidase (POX) from *Lactobacillus plantarum*, provides a three-dimensional model of AHAS structure that is useful for the design of herbicide-resistant AHAS variants or AHAS inhibiting herbicides. This modelling procedure takes advantage of the fact that AHAS and POX share a number of biochemical characteristics and may be derived from a common ancestral gene (Chang et al., *J. Bacteriol.* 170:3937, 1988).

Because of the high degree of cross-species homology in AHAS the modelled AHAS described herein or functional equivalents thereof can also be used as templates for AHAS variant protein design.

Derivation of one model using interactive molecular graphics and alignments is described in detail below. The three-dimensional AHAS structure that results from this procedure predicts the approximate spatial organization of the active site of the enzyme and of the binding site or pocket of inhibitors such as herbicides including, but not limited to, imidazolinone herbicides. The model is then refined and re-interpreted based on biochemical studies which are also described below.

Protein homology modelling requires the alignment of the primary sequence of the protein under study with a second protein whose crystal structure is known. Pyruvate oxidase (POX) was chosen for AHAS homology modelling because POX and AHAS share a number of biochemical characteristics. For example, both AHAS and POX share aspects of enzymatic reaction mechanisms, as well as cofactor and metal requirements. In both enzymes thiamine pyrophosphate (TPP), flavin adenine dinucleotide (FAD), and a divalent cation are required for enzymatic activity. FAD mediates a redox reaction during catalysis in POX but presumably has only a structural function in AHAS, which is possibly a vestigial remnant from the evolution of AHAS from POX. Both enzymes utilize pyruvate as a substrate and form hydroxyethyl thiamine pyrophosphate as a stable reaction intermediate (Schloss, J. V. et al. In *Biosynthesis of branched chain amino acids*, Barak, Z. J. M., Chipman, D. M., Schloss, J. V. (eds) VCH Publishers, Weinheim, Germany, 1990).

Additionally, AHAS activity is present in chimeric POX-AHAS proteins consisting of the N-terminal half of POX and the C-terminal half of AHAS, and there is a small degree of AHAS activity exhibited by POX itself. AHAS and POX also exhibit similar properties in solution (Risse, B. et al, *Protein Sci.* 1: 1699 and 1710, 1992; Singh, B. K., & Schmitt, G. K. (1989), *FEBS Letters*, 258: 113; Singh, B. K. et al. (1989) In: *Prospects for Amino Acid Biosynthesis Inhibitors in Crop Protection and Pharmaceutical Chemistry*, (Lopping, L. G., et al., eds., BCPC Monograph p. 87). With increasing protein concentration, both POX and AHAS undergo stepwise transitions from monomers to dimers and tetramers. Increases in FAD concentration also induce higher orders of subunit assembly. The tetrameric form of both proteins is most stable to heat and chemical denaturation.

Furthermore, the crystal structure of POX from *Lactobacillus planarum* had been solved by Muller et al., *Science* 259:965, 1993. The present inventors found that based in part upon the degree of physical, biochemical, and genetic homology between AHAS and POX, the X-ray crystal structure of POX could be used as a structural starting point for homology modelling of the AHAS structure.

AHAS and *L. plantarum* POX sequences were not similar enough for a completely computerized alignment, however. Overall, only about 20% of the amino acids are identical, while about 50% of the residues are of similar class (i.e. acidic, basic, aromatic, and the like). However, if the sequences are compared with respect to hydrophilic and hydrophobic residue classifications, over 500 of the 600 amino acids match. Secondary structure predictions for AHAS (Holley et al., *Proc.Natl.Acad.Sci. USA* 86:152, 1989) revealed a strong similarity to the actual secondary structure of POX. For nearly 70% of the residues, the predicted AHAS secondary structure matches that of POX.

POX monomers consist of three domains, all having a central, parallel β-sheet with crossovers consisting of α-helices and long loops. (Needleman et al, *J. Mol. Biol.* 48:443, 1970). The topology of the sheets differs between the domains, i.e. in the first and third domains, the strands are assembled to the β-sheet in the sequence 2-1-3-4-6-5, while in the β-sheet of the second domain, the sequence reads 3-2-1-4-5-6.

Computer generated alignments were based on secondary structure prediction and sequence homology. The conventional pair-wise sequence alignment method described by Needleman and Wunch, *J. Mol. Biol*, 48: 443, 1970, was used. Two sequences were aligned to maximize the alignment score. The alignment score (homology score) is the sum of the scores for all pairs of aligned residues, plus an optional penalty for the introduction of gaps into the alignment. The score for the alignment of a pair of residues is a tabulated integer value. The homology scoring system is based on observing the frequency of divergence between a given pair of residues. (M. O. Dayhoff, R. M. Schwartz & B. C. Orcutt "Atlas of Protein Sequence and Structure" vol. 5 suppl. 3 pp. 345–362, 1978).

The alignments were further refined by repositioning gaps so as to conserve continuous regular secondary structures. Amino acid substitutions generated by evaluation of likely alignment schemes were compared by means of interactive molecular graphics. Alignments with the most conservative substitutions with respect to the particular functionality of the amino acids within a given site were chosen. The final alignment of both POX and AHAS is displayed in FIG. 2. Conserved clusters of residues were identified, in particular for the TPP binding site and for parts of the FAD binding site. The alignment revealed a high similarity between AHAS and POX for the first domain, for most parts of the second domain, and for about half of the third domain. Most of the regions that aligned poorly and may fold differently in POX and in AHAS were expected to be at the surface of the protein and were not involved in cofactor or inhibitor binding. The prediction of mutation sites is not substantially affected by small shifts in the alignment.

Most TPP binding residues are highly conserved between POX and AHAS (e.g. P48-G49-G50). In some cases, residues that were close to TPP differ between POX and AHAS but remain within a region that is highly conserved (for example, residues 90–110). On the other hand, the FAD binding site appeared to be less conserved. Although some FAD binding resides were strongly conserved (for example, D325-I326-D327-P328), others clearly differed between AHAS and POX (for example, residues in the loop from positions 278 to 285 are not homologous. A detailed analysis revealed that, at least for some of the less-conserved contact sites, the interactions were mediated by the polypeptide backbone rather than by the side chains. Hence, conservation was only required for the polypeptide fold and was not required for the amino acid sequence (for example, the backbone of residues 258–263 binds the ribitol chain of FAD). One half of the adenine and the isoalloxazine binding sites clearly differ.

Figure 3B:
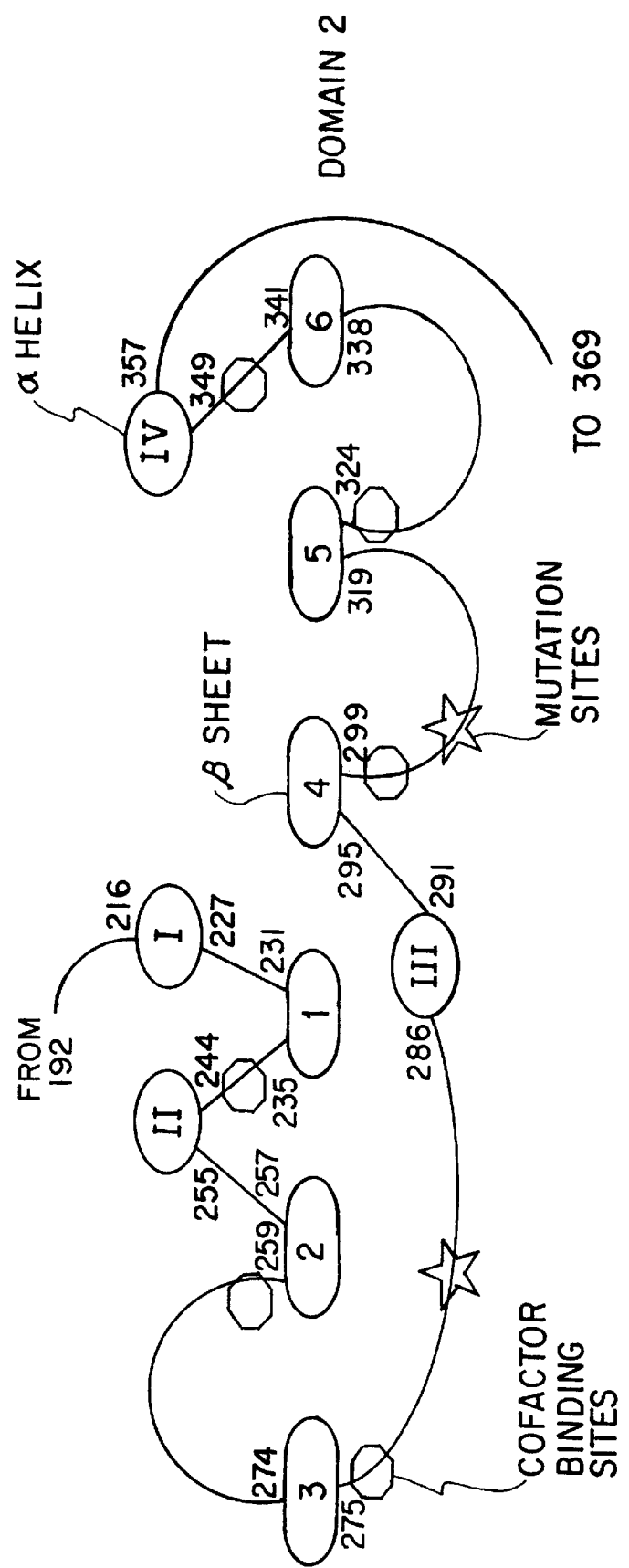
Figure 3C:
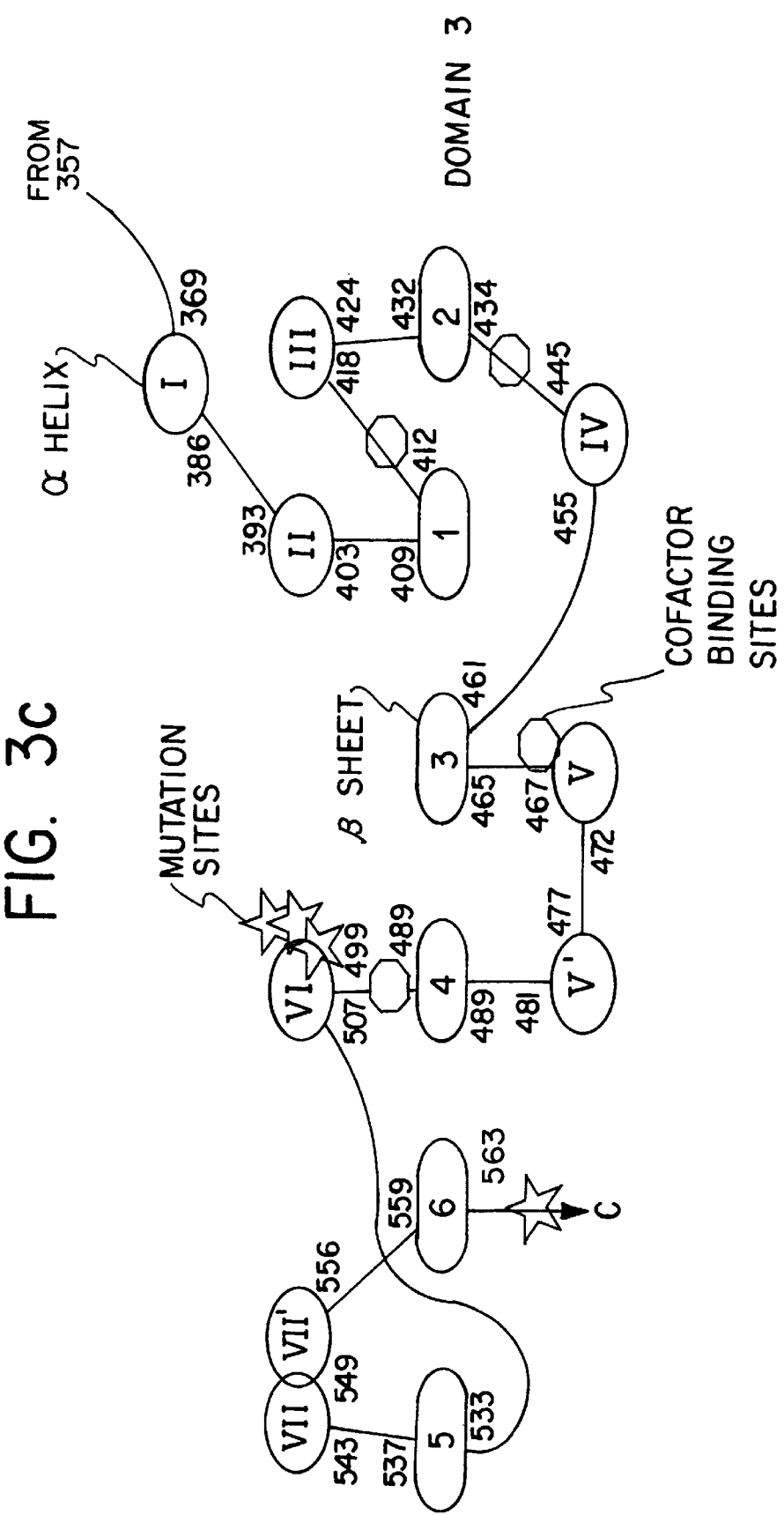

After aligning the primary structure, a homology model was built by transposition of AHAS amino acid sequences to the POX template structure. Missing coordinates were built stepwise using templates of amino acid residues to complete undefined side chains. Data bank searches and energy minimization of small parts of the molecule were used to complete the conformations of undefined loop regions. The cofactors TPP and FAD were modeled into their binding pockets. This model was then subjected to a complete, 5000 cycle energy minimization. All computer modelling was performed in an IRIS Indigo Elan R4000 Workstation from Silicon Graphics Co. Interactive molecular modelling and energy-minimization were performed using Quanta/CHARMm 4.0 from Molecular Simulations Inc. During this step, the conformation was stable, indicating that no strongly disfavored interactions, such as, for example, close van der Waals contacts, had occurred. The results are shown schematically in FIG. 3.

Characteristics of Predicted AHAS Structure

Inspection of the modelled AHAS structure described above revealed that most of the protein folds with a backbone that is energetically reasonable, with most hydrophilic side chains accessible to the solvent. The surface of the β-sheets are smooth and accommodate the cross-over regions that are attached to them.

A model for dimeric AHAS was generated by duplicating the coordinates of the energy minimized monomeric AHAS and superimposing the two copies on two POX subunits using pairs of Cα coordinates as defined in the alignment scheme. The polypeptide chain of AHAS folds into three similarly folded domains composed of a six-stranded parallel β-sheet core surrounded by long "loops" and α-helices. Two subunits are assembled such that the first domain of one subunit is in close proximity to the cofactorbinding domains 2 and 3 of the other subunit. A solvent-filled space remains between the subunits at this site. This pocket, which is defined by the confluence of the three domains, is the proposed entry site for the substrate. It is also proposed to be the binding site for herbicides.

The inner surface of the binding pocket is outlined by the cofactors. The thiazol of TPP is positioned at the bottom of the pocket. Domain 3 contributes to the inner surface of the pocket with a short α-helix that points its axis towards the pyrophosphate of TPP, compensating the phosphate charges with its dipolar moment. This critical helix, which starts with G498, a "turn" residue in close contact with TPP, and which ends at F507, contains three known mutation sites for sulfonylurea resistance: V500, W503, and F507 (See, U.S. Pat. Nos. 5,013,659; 5,141,870; and 5,378,824). In domain 1, the loop defined as P48-S52 (between β-strand 2 and α-helix 2) faces W503, a mutation in which confers resistance to imidazolinones. Residues Y47 to G50 are also in contact with TPP. This loop is adjacent to P184-Q189, another turn, which connects the last strand of the β-sheet of domain 1 with a β-strand that connects with domain 2. Within the pocket, near its entrance, is a long region of domain 1 that interacts with a complementary stretch of domain 2. Residues 125–129 and 133–137 of domain 1 and residues 304–313 of domain 2 are at the surface of the pocket. A turn consisting of T96-G100 is between loop 125–129 and TPP. A further stretch of domain 3 and two regions of domain 2 that line the binding pocket are at the opposite corner of the pocket. Residues 572, 575, 582, and 583 of domain 3 define the pocket surface on one side. The remaining part of the interior of the pocket's surface is defined by FAD and by a loop, L278-G282, that contacts the isoalloxazine ring of FAD.

The structural models of the AHAS protein can also be used for the rational design of herbicides or AHAS inhibitors.

2. Modelling of Herbicides Into Binding Sites

Figure 4:
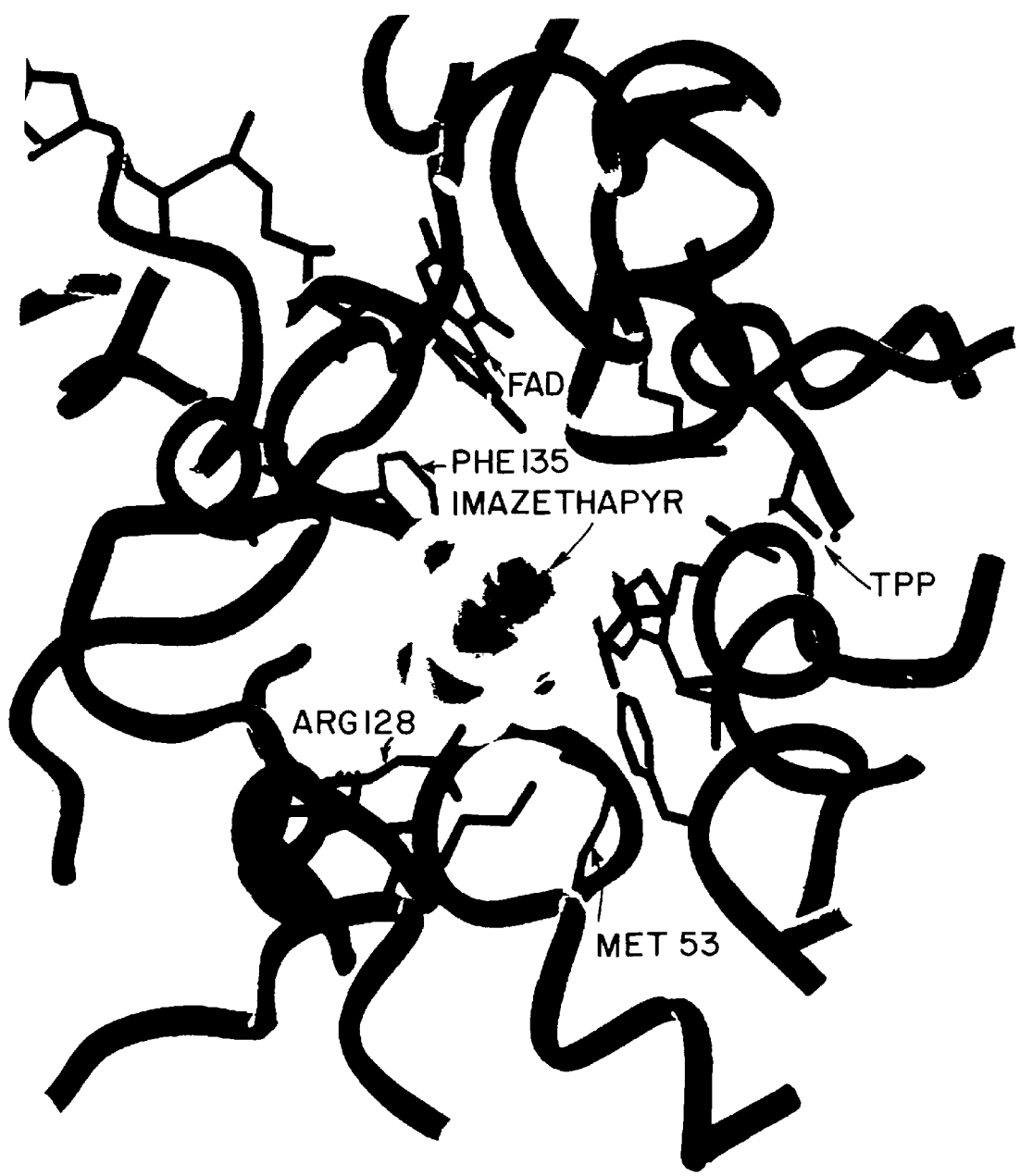

Imazethapyr, the active imidazolinone in PURSUIT®, was positioned into its proposed binding site using interactive molecular graphics (FIG. 4) and the software described above (FIG. 4). K185 was chosen as an "anchor" to interact with the charge of the carboxyl group. The imidazolinone's NH—CO unit was placed to form hydrogen bonds to G50 and A51. This positioned the methyl substitute of imazethapyr close to V500 on the backbone of the small α-helix. The isopropyl group is possibly bound by hydrophobic residues of the amino acids in the region of residues 125–135 that contribute to the inner surface of the pocket. The pyridine ring is most probably "sandwiched" between A134 or F135, F507 and W503. W503 also interacts with the imidazolinone ring system.

In a similar fashion, the sulfonylurea herbicides were modelled into a site that partially overlapped the described imidazolinone binding site. Overlap of sulfonylurea and imidazolinone binding sites was consistent with competition binding experiments and with established mutant data, which show that the same mutation in maize, W503L, can confer resistance to both herbicides. In these models, most of the known mutation sites that confer sulfonylurea herbicide resistance, i.e. G50, A51, K185, V500, W503, F507, are in close contact to the bound herbicides. P126 and A51 are required for keeping the K185 side chain in place by generating a hydrophobic pore. S582, a site for specific imidazolinone resistance, is distant from the binding region and is located in the region where the homology is so poor that a change in the fold is expected. The FAD binding site apparently has low homology between AHAS and POX in this region; S582 is a residue that confers resistance in maize, and that S582 and its adjacent residues are in close contact to the active site pocket. It is proposed that FAD and the loop region encompassing residues 278 to 285 move slightly away from the third domain, (downward in FIG. 4) and that a loop that contains S582 folds into the space between the helix at positions 499 to 507 and the loop at positions 278 to 285. D305, another known resistance site, is close to FAD and modulates the interaction between domains 1 and 2. M280 may either be involved in positioning of the helix at positions 498 to 507 or directly in inhibitor binding. M280 and D305 could also be directly involved in inhibitor binding if domains 1 and 2 move slightly closer to each other.

3. Selection of Mutations

Specific amino acid residues are pinpointed as sites for the introduction of mutations into the primary sequence of AHAS. These amino acids are selected based upon their position in that if that amino acid residue position is modified, there will be a resultant alteration (i.e. decline) in the affinity of an herbicide for the binding pocket. It is not necessary that the mutation position reside in the binding pocket as amino acid residues outside the pocket itself can alter the pocket charge or configuration. The selection of target sites for mutation is achieved using molecular models as described above. For example according to the model above, arginine at position 128 (designated R128 in FIG. 1 using the single-letter code for amino acids) is located near the entrance to the substrate- and herbicide-binding pocket and has a large degree of conformational freedom that may allow it to participate in transport of charged herbicides into the binding pocket. Therefore, this residue is substituted by alanine to remove both its charge and its long hydrophobic side chain. (The resulting mutation is designated R128A).

The mutations may comprise simple substitutions, which replace the wild-type sequence with any other amino acid. Alternatively, the mutations may comprise deletions or additions of one or more amino acids, preferably up to 5, at a given site. The added sequence may comprise an amino acid sequence known to exist in another protein, or may comprise a completely synthetic sequence. Furthermore, more than one mutation and/or more than one type of mutation may be introduced into a single polypeptide.

4. Site-Directed Mutagenesis

The DNA encoding AHAS can be manipulated so as to introduce the desired mutations. Mutagenesis is carried out using methods that are standard in the art, as described in, for example, Higuchi, R., Recombinant PCR, In M.A. Innis, et at., eds; PCR Protocols: A Guide to Methods and Applications, Academic Press, pp. 177–183, 1990.

5. Expression and Purification of Variants

The mutated or variant AHAS sequence is cloned into a DNA expression vector (see, e.g., Example 3) and is expressed in a suitable cell such as, for example, *E. coli*. Preferably, the DNA encoding AHAS is linked to a transcription regulatory element, and the variant AHAS is expressed as part of a fusion protein, for example, glutathione-S-transferase, to facilitate purification (see Example 3 below). The variant AHAS is then purified using affinity chromatography or any other suitable method known in the art. "Purification" of an AHAS polypeptide refers to the isolation of the AHAS polypeptide in a form that allows its enzymatic activity to be measured without interference by other components of the cell in which the polypeptide is expressed.

6. Assaying of Enzymatic Properties

The purified variant AHAS may be assayed for one or more of the following three properties:

(a) specific or catalytic activity for conversion of pyruvate to acetolactate (expressed as units/mg pure AHAS, wherein a unit of activity is defined as 1 μmole acetolactate produced/hour), or for condensation of pyruvate and 2-ketobutyrate to form acetohydroxybutyrate (expressed as units/mg pure AHAS, wherein a unit of activity is defined as 1 μmole acetohydroxybutyrate produced/hr.;

(b) level of inhibition by herbicide, such as, for example, imidazolinone (expressed as $IC_{50}$, the concentration at which 50% of the activity of the enzyme is inhibited); and (c) selectivity of resistance to the selected herbicide vs. other herbicides. The selectivity index is defined as the fold resistance of the mutant to imidazolinones relative to the wild-type enzyme, divided by the fold resistance of the same mutant to other herbicides also relative to the wild-type). Fold resistance to an herbicide relative to the wild-type enzyme is expressed as the $IC_{50}$ of variant, divided by the $IC_{50}$ of the wild type. The selectivity index (S.I.) is thus represented by the following equation:

$$S.I. = \frac{IC_{50} \text{ of variant for herb} \cdot A/IC_{50} \text{ of wild type for herb} \cdot A}{IC_{50} \text{ of variant for herb} \cdot B/IC_{50} \text{ of wild type for herb} \cdot B.}$$

Suitable assay systems for making these determinations include, but are not limited to, those described in detail in Example 4 below.

7.a. Evaluation of Suitable Variants

The enzymatic properties of variant AHAS polypeptides are compared to the wild-type AHAS. Preferably, a given mutation results in an AHAS variant polypeptide that retains in vitro enzymatic activity towards pyruvate or pyruvate and 2-ketobutyrate, i.e., the conversion of pyruvate to acetolactate or in the condensation of pyruvate and 2-ketobutyrate to form acetohydroxybutyrate (and thus is expected to be biologically active in vivo), while exhibiting catalytic activity that is relatively more resistant to the selected herbicide (s) than is wild-type AHAS. Preferably, the variant AHAS exhibits:

(i) in the absence of the at least one herbicide,
(a) catalytic activity alone sufficient to maintain the viability of a cell in which it is expressed; or
(b) catalytic activity in combination with any herbicide resistant AHAS variant protein also expressed in the cell, which may be the same as or different than the first AHAS variant protein, sufficient to maintain the viability of a cell in which it is expressed;
wherein the cell requires AHAS activity for viability; and (ii) catalytic activity that is more resistant to the at least one herbicide than is wild type AHAS;
and that is relatively more resistant to the herbicide(s) than is wild-type AHAS.

Therefore, any one specific AHAS variant protein need not have the total catalytic activity necessary to maintain the viability of the cell, but must have some catalytic activity in an amount, alone or in combination with the catalytic activity of additional copies of the same AHAS variant and/or the catalytic activity of other AHAS variant protein (s), sufficient to maintain the viability of a cell that requires AHAS activity for viability. For example, catalytic activity may be increased to minimum acceptable levels by introducing multiple copies of a variant encoding gene into the cell or by introducing the gene which further includes a relatively strong promoter to enhance the production of the variant.

More resistant means that the catalytic activity of the variant is diminished by the herbicide(s), if at all, to a lesser degree than wild-type AHAS catalytic activity is diminished by the herbicide(s). Preferred more resistant variant AHAS retains sufficient catalytic to maintain the viability of a cell, plant, or organism wherein at the same concentration of the same herbicide(s), wild-type AHAS would not retain sufficient catalytic activity to maintain the viability of the cell, plant, or organism.

Preferably the catalytic activity in the absence of herbicide(s) is at least about 5% and, most preferably, is more than about 20% of the catalytic activity of the wild-type AHAS in the absence of herbicide(s). Most preferred AHAS variants are more resistant to imidazolinone herbicides than to other herbicides such as sulfonylurea-based herbicides, though in some applications selectivity is neither needed nor preferred.

In the case of imidazolinone-resistant variant AHAS, it is preferred that the AHAS variant protein has (i) catalytic activity in the absence of said herbicide of more than about 20% of the catalytic activity of said wild-type AHAS;

(ii) catalytic activity that is relatively more resistant to presence of imidazolinone herbicides compared to wild type AHAS; and (iii) catalytic activity that is relatively more sensitive to the presence of sulfonylurea herbicides compared to imidazolinone herbicides. Most preferred herbicide resistant AHAS variants exhibit a minimum specific activity of about 20 units/mg, minimal or no inhibition by imidazolinone, and a selectivity index ranging from about 1.3 to about 3000 relative to other herbicides.

Without wishing to be bound by theory, it is believed that systematic and iterative application of this method to wild type or other target AHAS protein will result in the production of AHAS variants having the desired properties of high enzymatic activity as explained above and resistance to one or more classes of herbicides. For example, mutation of a wild-type AHAS sequence at a particular position to a given amino acid may result in a mutant that exhibits a high degree of herbicide resistance but a significant loss of enzymatic activity towards pyruvate or pyruvate and 2-ketobutyrate. In a second application of the above method, the starting or target AHAS polypeptide would then be this variant (in place of the wild-type AHAS). Rational design then involves substituting other amino acids at the originally mutated position and/or adding or deleting amino acids at selected points or ranges in the expectation of retaining herbicide resistance but also maintaining a higher level of enzymatic activity.

The structure-based rational design of herbicide resistant AHAS proteins offers many advantages over conventional approaches that rely on random mutagenesis and selection. For example, when substitution of a particular amino acid with another requires substitution of more than one nucleotide within the codon, the likelihood of this occurring randomly is so low as to be impractical. By contrast, even double or triple changes in nucleotide sequence within a codon can be easily implemented when suggested by a rational design approach. For example, one rationally designed mutation to confer selective imidazolinone resistance requires a change from arginine to glutamate. Arginine is encoded by CGT, CGC, CGA, CGG, AGA, AGG, while glutamate is encoded by GAA and GAG. Since none of the arginine codons begins with GA, this mutation would require a double substitution of adjacent nucleotides which would occur so rarely using random mutagenesis as to be unpredictable and unrepeatable with any certainty of success. Although mutation frequency can be increased during random mutagenesis, alterations in nucleotide sequence would have an equal probability of occurring throughout the AHAS gene, in the absence of prior site-direction of the mutations. This increases the chance of obtaining an irrelevant mutation that interferes with enzymatic activity. Similarly, it would be rare, using random mutagenesis, to find a multiple amino acid substitution, deletion, or substitution/deletion mutation that confers herbicide resistance while maintaining catalytic activity. Deletion mutations that confer herbicide resistance would also be unlikely using a random mutagenesis approach. Deletions would need to be limited to small regions and would have to occur in triplets so as to retain the AHAS reading frame in order to retain enzymatic activity.

However, with a rational structure-based approach, double amino acid substitution and/or deletion mutations are relatively easily achieved and precisely targeted. Furthermore, different mutagens used in random mutagenesis create specific types of mutations. For example, sodium azide creates point substitution mutations in plants, while radiation tends to create deletions. Accordingly, two mutagenesis protocols would have to be employed to obtain a multiple combination substitution/deletion.

Finally, the present structure-based method for rational design of herbicide resistant AHAS variants allows for iterative improvement of herbicide resistance mutations, a step that is not facilitated by random mutagenesis. Identification of a mutation site for herbicide resistance by random mutagenesis may offer little, if any, predictive value for guiding further improvements in the characteristics of the mutant. The present structure-based approach, on the other hand, allows improvements to be implemented based on the position, environment, and function of the amino acid position in the structural model.

The iterative improvement method also allows the independent manipulation of three important properties of AHAS: level of resistance, selectivity of resistance, and catalytic efficiency. For example, compensatory mutations can be designed in a predictive manner. If a particular mutation has a deleterious effect on the activity of an enzyme, a second compensatory mutation may be used to restore activity. For example, a change in the net charge within a domain when a charged residue is introduced or lost due to a mutation can be compensated by introducing a second mutation. Prediction of the position and type of residue(s) to introduce, delete, or substitute at the second site in order to restore enzymatic activity requires a knowledge of structure-function relationships derived from a model such as that described herein.

7.b. Design of Non-Peptide Herbicides or AHAS Inhibitors

A chemical entity that alters and may fit into the activity site of the target protein may be designed by methods known in the art, such as, for example, computer design programs that assist in the design of compounds that specifically interact with a receptor site.

An example of such a program is LUDI (Biosym Technologies-San Diego, Calif.) (see also, Lam, et al., *Science* 263:380, 1994; Thompson, et al., *J. Med. Chem.*, 37:3100, 1994).

The binding pocket and particularly the amino acid residues that have been identified as being involved as inhibitor binding can be used as anchor points for inhibitor design.

The design of site-specific herbicides is advantageous in the control of weed species that may spontaneously develop herbicide resistance in the field, particularly due to mutations in the AHAS gene.

Herbicide-Resistant AHAS Variants: DNA, Vectors, and Polypeptides

The present invention also encompasses isolated DNA molecules encoding variant herbicide-resistant AHAS polypeptides. Genes encoding AHAS polypeptides according to the present invention may be derived from any species and preferably a plant species, and mutations conferring herbicide resistance may be introduced at equivalent positions within any of these AHAS genes. The equivalence of a given codon position in different AHAS genes is a function of both the conservation of primary amino acid sequence and its protein and the retention of similar three-dimensional structure. For example, FIG. 5 illustrates the high degree of sequence homology between AHAS polypeptides derived from different plant species. These AHAS polypeptides exhibit at least about 60 to about 70% overall homology. Without wishing to be bound by theory, it is believed that in regions of the polypeptide having a highly conserved sequence, the polypeptide chain conformation will also be preserved. Thus, it is possible to use an AHAS-encoding sequence from one species for molecular modelling, to introduce mutations predictively into an AHAS gene from a second species for initial testing and iterative improvement, and finally, to introduce the optimized mutations into AHAS derived from yet a third plant species for expression in a transgenic plant.

In one series of embodiment, these AHAS DNAs encode variants of an AHAS polypeptide and preferably of the maize AHAS polypeptide of FIG. 1 in which the polypeptide is modified by substitution at or deletion preceding or following one or more of FIG. 1 amino acid residues P48, G49, S52, M53, E54, A84, A95, T96, S97, G98, P99, G100, A101, V125, R127, R128, M129, I130, G131, T132, D133, F135, Q136, D186, I187, T259, T260, L261, M262, G263, R276, M277, L278, G279, H281, G282, T283, V284, G300, V301, R302, F303, D304, R306, V307, T308, G309, K310, I311, E312, A313, F314, A315, S316, R317, A318, K319, I320, E329, I330, K332, N333, K334, Q335, T404, G413, V414, G415, Q416, H417, Q418, M419, W420, A421, A422, L434, S435, S436, A437, G438, L439, G440, A441, M442, G443, D467, G468, S469, L471, N473, L477, M479, Q495, H496, L497, G498, M499, V501, Q502, Q504, D505, R506, Y508, K509, A510, N511, R512, A513, H514, T515, S524, H572, Q573, E574, H575, V576, L577, P578, M579, I580, P581, G583, G584, functional equivalents of any of the foregoing; insertions or deletions between FIG. 1 Q124 and H150 or functional equivalents thereof; insertions or deletions between FIG. 1 G300 and D324 or functional equivalents thereof; and any combination of any of the foregoing thereof.

The mutations, whether introduced into the polypeptide of FIG. 1 or at equivalent positions in another plant AHAS gene, may comprise alterations in DNA sequence that result in a simple substitution of any one or more other amino acids or deletions of up to 5 amino acid residues proceeding or up to 5 amino acids residues following any of the residence listed above. Suitable amino acid substituents include, but are not limited to, naturally occurring amino acids.

Alternatively, the mutations may comprise alterations in DNA sequence such that one or more amino acids are added or deleted in frame at the above positions. Preferably, additions comprise about 3 to about 30 nucleotides, and deletions comprise about 3 to about 30 nucleotides. Furthermore, a single mutant polypeptide may contain more than one similar or different mutation.

The present invention encompasses DNA and corresponding RNA sequences, as well as sense and antisense sequences. Nucleic acid sequences encoding AHAS polypeptides may be flanked by natural AHAS regulatory sequences, or may be associated with heterologous sequences, including promoters, enhancers, response elements, signal sequences, polyadenylation sequences, introns, 5'- and 3'-noncoding regions, and the like. Furthermore, the nucleic acids can be modified to alter stability, solubility, binding affinity and specificity. For example, variant AHAS-encoding sequences can be selectively methylated. The nucleic acid sequences of the present invention may also be modified with a label capable of providing a detectable signal, either directly or indirectly. Exemplary labels include radioisotopes, fluorescent molecules, biotin, and the like.

The invention also provides vectors comprising nucleic acids encoding AHAS variants. A large number of vectors, including plasmid and fungal vectors, have been described for expression in a variety of eukaryotic and prokaryotic hosts. Advantageously, vectors may also include a promotor operably linked to the AHAS encoding portion. The encoded AHAS may be expressed by using any suitable vectors and host cells, using methods disclosed or cited herein or otherwise known to those skilled in the relevant art. Examples of suitable vectors include without limitation pBIN-based vectors, pBluescript vectors, and pGEM vectors.

The present invention also encompasses both variant herbicide-resistant AHAS polypeptides or peptide fragments thereof. As explained above, the variant AHAS polypeptides may be derived from the maize polypeptide shown in FIG. 1 or from any plant or microbial AHAS polypeptide, preferably plant AHAS polypeptide. The polypeptides may be further modified by, for example, phosphorylation, sulfation, acylation, glycosylation, or other protein modifications. The polypeptides may be isolated from plants, or from heterologous organisms or cells (including, but not limited to, bacteria, yeast, insect, plant, and mammalian cells) into which the gene encoding a variant AHAS polypeptide has been introduced and expressed. Furthermore, AHAS polypeptides may be modified with a label capable of providing a detectable signal, either directly or indirectly, including radioisotopes, fluorescent compounds, and the like.

Chemical-resistant Plants and Plants Containing Variant AHAS Genes

The present invention encompasses transgenic cells, including, but not limited to seeds, organisms, and plants into which genes encoding herbicide-resistant AHAS variants have been introduced. Non-limiting examples of suitable recipient plants are listed in Table 1 below:

TABLE 1

RECIPIENT PLANTS

| COMMON NAME | FAMILY | LATIN NAME |
| --- | --- | --- |
| Maize | Gramineae | Zea mays |
| Maize, Dent | Gramineae | Zea mays dentiformis |
| Maize, Flint | Gramineae | Zea mays vulgaris |
| Maize, Pop | Gramineae | Zea mays microsperma. |
| Maize, Soft | Gramineae | Zea mays amylacea |
| Maize, Sweet | Gramineae | Zea mays amyleasaccharata |
| Maize, Sweet | Gramineae | Zea mays saccharate |
| Maize, Waxy | Gramineae | Zea mays ceratina |
| Wheat, Dinkel | Pooideae | Triticum spelta |
| Wheat, Durum | Pooideae | Triticum durum |
| Wheat, English | Pooideae | Triticum turgidum |
| Wheat, Large Spelt | Pooideae | Triticum spelta |
| Wheat, Polish | Pooideae | Triticum polonium |
| Wheat, Poulard | Pooideae | Triticum turgidum |
| Wheat, Singlegrained | Pooideae | Triticum monococcum |
| Wheat, Small Spelt | Pooideae | Triticum monococcum |
| Wheat, Soft | Pooideae | Triticum aestivum |
| Rice | Gramineae | Oryza sativa |
| Rice, American Wild | Gramineae | Zizania aquatica |
| Rice, Australian | Gramineae | Oryza australiensis |
| Rice, Indian | Gramineae | Zizania aquatica |
| Rice, Red | Gramineae | Oryza glaberrima |
| Rice, Tuscarora | Gramineae | Zizania aquatica |
| Rice, West African | Gramineae | Oryza glaberrima |
| Barley | Pooideae | ordeum vulgare |
| Barley, Abyssinian Intermediate, also Irregular | Pooideae | Hordeum irregulare |
| Barley, Ancestral Tworow | Pooideae | Hordeum spontaneum |
| Barley, Beardless | Pooideae | Hordeum trifurcatum |
| Bariey, Egyptian | Pooideae | Hordeum trircatum |
| Bariey, fourrowed | Pooideae | Hordeum vulgare polystichon |
| Barley, sixrowed | Pooideae | Hordeum vulgare hexastichon |
| Bariey, Tworowed | Pooideae | Hordeum distichon |
| Cotton, Abroma | Dicotyledoneae | Abroma augusta |
| Cotton, American Upland | Malvaceae | Gossypium hirsutum |
| Cotton, Asiatic Tree, also Indian Tree | Malvaceae | Gossypium arboreum |
| Cotton, Brazilian, also, Kidney, and, Pemambuco | Malvaceae | Gossypium barbadense brasiliense |
| Cotton, Levant | Malvaceae | Gossypium herbaceum |
| Cotton, Long Silk, also Long Staple, Sea Island | Malvaceae | Gossypium barbadense |
| Cotton, Mexican, also Short Staple | Malvaceae | Gossypium hirsutum |
| Soybean, Soya | Leguminosae | Glycine max |
| Sugar beet | Chenopodiaceae | Beta vulgaris altissima |
| Sugar cane | Woody-plant | Arenga pinnata |
| Tomato | Solanaceae | Lycopersicon esculentum |
| Tomato, Cherry | Solanaceae | Lycopersicon esculentum cerasiforme |
| Tomato, Common | Solanaceae | Lycopersicon esculentum commune |
| Tomato, Currant | Solanaceae | Lycopersicon pimpinellifolium |
| Tomato, Husk | Solanaceae | Physalis ixocarpa |
| Tomato, Hyenas | Solanaceae | Solanum incanum |
| Tomato, Pear | Solanaceae | Lycopersicon esculentum pyriforme |
| Tomato, Tree | Solanaceae | Cyphomandra betacea |
| Potato | Solanaceae | Solanum tuberosum |
| Potato, Spanish, Sweet potato | Convolvulaceae | Ipomoea batatas |
| Rye, Common | Pooideae | Secale cereale |
| Rye, Mountain | Pooideae | Secale montanum |
| Pepper, Bell | Solanaceae | Capsicum annuum grossum |
| Pepper, Bird, also Cayenne, Guinea | Solanaceae | Capsicum annuum minimum |
| Pepper, Bonnet | Solanaceae | Capsicum sinense |

TABLE 1-continued

RECIPIENT PLANTS

| COMMON NAME | FAMILY | LATIN NAME |
|---|---|---|
| Pepper, Bullnose, also Sweet | Solanaceae | *Capsicum annuum grossum* |
| Peppet, Cherry | Solanaceae | *Capsicum annuum cerasiforme* |
| Pepper, Cluster, also Red Cluster | Solanaceae | *Capsicum annuum fasciculatum* |
| Pepper, Cone | Solanaceae | *Capsicum annuum conoides* |
| Pepper, Goat, also Spur | Solanaceae | *Capsicum frutescens* |
| Pepper, Long | Solanaceae | *Capsicum frutescens longum* |
| Pepper, Oranamental Red, also Wrinkled | Solanaceae | *Capsicum annuum abbreviatum* |
| Pepper, Tabasco Red | Solanaceae | *Capsicum annuum conoides* |
| Lettuce, Garden | Compositae | *Lactuca sativa* |
| Lettuce, Asparagus, also Celery | Compositae | *Lactuca sativa asparagina* |
| Lettuce, Blue | Compositae | *Lactuca perennis* |
| Lettuce, Blue, also Chicory | Compositae | *Lactuca pulchella* |
| Lettuce, Cabbage, also Head | Compositae | *Lactuca sativa capitata* |
| Lettuce, Cos, also Longleaf, Romaine | Compositae | *Lactuca sativa longifolia* |
| Lettuce, Crinkle, also Curled, Cutting, Leaf | Compositae | *Lactuca sativa crispa* |
| Celery | Umbelliferae | *Apium graveolens dulce* |
| Celery, Blanching, also Garden | Umbelliferae | *Apium graveolens dulce* |
| Celery, Root, also Turniprooted | Umbelliferae | *Apium graveolens rapaceum* |
| Eggplant, Garden | Solanaceae | *Solanum melongena* |
| Sorghum | Sorghum | All crop species |
| Alfalfa | Leguminosae | *Medicago sativum* |
| Carrot | Umbelliferae | *Daucus carota sativa* |
| Bean, Climbing | Leguminosae | *Phaseolus vulgaris vulgaris* |
| Bean, Sprouts | Leguminosae | *Phaseolus aureus* |
| Bean, Brazilian Broad | Leguminosae | *Canavalia ensiformis* |
| Bean, Broad | Leguminosae | *Vicia faba* |
| Bean, Common, also French, White, Kidney | Leguminosae | *Phaseolus vulgaris* |
| Bean, Egyptian | Leguminosae | *Dolichos lablab* |
| Bean, Long, also Yardlong | Leguminosae | *Vigna sesquipedalis* |
| Bean, Winged | Leguminosae | *Psophocarpus tetragonoiobus* |
| Oat, also Common, Side, Tree | Avena | Sativa |
| Oat, Black, also Bristie, Lopsided | Avena | Strigosa |
| Oat, Bristle | Avena | |
| Pea, also Garden, Green, Shelling | Leguminosae | *Pisum, sativum sativum* |
| Pea, Blackeyed | Leguminosae | *Vigna sinensis* |
| Pea, Edible Podded | Leguminosae | *Pisum sativum axiphium* |
| Pea, Grey | Leguminosae | *Pisum sativum speciosum* |
| Pea, Winged | Leguminosae | *Tetragonolobus purpureus* |
| Pea, Wrinkled | Leguminosae | *Pisum sativum medullare* |
| Sunflower | Compositae | *Helianthus annuus* |
| Squash, Autumn, Winter | Dicotyledoneae | *Cucurbita maxima* |
| Squash, Bush, also Summer | Dicotyledoneae | *Cucurbita pepo melopepo* |
| Squash, Turban | Dicotyledoneae | *Cucurbita maxima turbaniformis* |
| Cucumber | Dicotyledoneae | *Cucumis sativus* |
| Cucumber, African, also Bitter | | *Momordica charantia* |
| Cucumber, Squirting, also Wild | | *Ecballium elaterium* |
| Cucumber, Wild | | *Cucumis anguria* |
| Poplar, California | Woody-Plant | *Populus trichocarpa* |
| Poplar, European Black | | *Populus nigra* |
| Poplar, Gray | | *Populus canescens* |
| Poplar, Lombardy | | *Populus italica* |
| Poplar, Silverleaf, also White | | *Populus alba* |
| Poplar, Western Balsam | | *Populus trichocarpa* |
| Tobacco | Solanaceae | *Nicotiana* |
| Arabidopsis Thaliana | Cruciferae | *Arabidopsis thaliana* |
| Turfgrass | Lolium | |
| Turfgrass | Agrostis Other families of turfgrass | |
| Clover | Leguminosae | |

Expression of the variant AHAS polypeptides in transgenic plants confers a high level of resistance to herbicides including, but not limited to, imidazolinone herbicides such as, for example, imazethapyr (PURSUIT®), allowing the use of these herbicides during cultivation of the transgenic plants.

Methods for the introduction of foreign genes into plants are known in the art. Non-limiting examples of such methods include Agrobacterium infection, particle bombardment, polyethylene glycol (PEG) treatment of protoplasts, electroporation of protoplasts, microinjection, macroinjection, tiller injection, pollen tube pathway, dry seed imbibition, laser perforation, and electrophoresis. These methods are described in, for example, B. Jenes et al., and S. W. Ritchie et al. In *Transgenic Plants*, Vol. 1, *Engineering and Utilization*, ed. S.-D. Kung, R. Wu, Academic Press, Inc., Harcourt Brace Jovanovich 1993; and L. Mannonen et al., *Critical Reviews in Biotechnology*, 14:287–310, 1994.

Other Applications

The methods and compositions of the present invention can be used in the structure-based rational design of herbicide-resistant AHAS variants, which can be incorporated into plants to confer selective herbicide resistance on the plants. Intermediate variants of AHAS (for example, variants that exhibit sub-optimal specific activity but high resistance and selectivity, or the converse) are useful as templates for the design of secondgeneration AHAS variants that retain adequate specific activity and high resistance and selectivity.

Herbicide resistant AHAS genes can be transformed into crop species in single or multiple copies to confer herbicide resistance. Genetic engineering of crop species with reduced sensitivity to herbicides can:

(1) Increase the spectrum and flexibility of application of specific effective and environmentally benign herbicides such as imidazolinone herbicides;

(2) Enhance the commercial value of these herbicides;

(3) Reduce weed pressure in crop fields by effective use of herbicides on herbicide resistant crop species and a corresponding increase in harvest yields;

(4) Increase sales of seed for herbicide-resistant plants;

(5) Increase resistance to crop damage from carry-over of herbicides applied in a previous planting;

(6) Decrease susceptibility to changes in herbicide characteristics due to adverse climate conditions; and (7) Increase tolerance to unevenly or mis-applied herbicides.

For example, transgenic AHAS variant protein containing plants can be cultivated. The crop can be treated with a weed controlling effective amount of the herbicide to which the AHAS variant transgenic plant is resistant, resulting in weed control in the crop without detrimentally affecting the cultivated crop.

The DNA vectors described above that encode herbicide-resistant AHAS variants can be further utilized so that expression of the AHAS variant provides a selectable marker for transformation of cells by the vector. The intended recipient cells may be in culture or in situ, and the AHAS variant genes may be used alone or in combination with other selectable markers. The only requirement is that the recipient cell is sensitive to the cytotoxic effects of the cognate herbicide. This embodiment takes advantage of the relative low cost and lack of toxicity of, for example, imidazolinonebased herbicides, and may be applied in any system that requires DNA-mediated transformation.

Description of the Preferred Embodiments

The following examples are intended to illustrate the present invention without limitation.

Example 1
Design of herbicide-resistant AHAS variants

Residues located close to the proposed herbicide binding site of the model described in detail above and are expected to be directly involved in enzymatic activity were selected for mutagenesis in order to design an active AHAS polypeptide with decreased herbicide binding capacity. Each site at the surface of the pocket was considered in terms of potential interactions with other residues in the pocket, as well as with cofactors and herbicides. For example, addition of positively charged residue(s) is expected to interfere with the charge distribution within the binding site, resulting in a loss in affinity of binding of a negatively-charged herbicide.

Three residues were identified as most useful targets for mutagenesis:

(1) F135 was believed to interact with both the isoalloxazine ring of FAD and with the aromatic group of the herbicides. In accordance with the strategy of introducing more charged residues into the binding pocket, this residue was changed to arginine.

(2) M53 contacts helix 498–507, which contains known herbicide resistance mutation sites and is also implicated in TPP binding. Furthermore, substitution of glutamic acid at position 53 was believed to favor an interaction with K185, reducing the affinity of K185 for the carboxylate group of imazethapyr.

(3) R128 is located near the entrance to the pocket, where it was believed to be involved in the initial transport of charged herbicides into the binding pocket. This residue was changed to alanine to remove both its charge and its long hydrophobic side chain.

Example 2
Site-directed mutagenesis of AHAS to produce herbicide-resistant variants The Arabidopsis AHAS gene was inserted in-frame to the 3' end of the coding region of the glutathione S-transferase gene in the pGEX-2T vector (Pharrnacia). Construction of the vector in this manner maintained the six amino acid thrombin recognition sequence at the junction of the expressed glutathione-S-transferase (GST)/AHAS fusion protein. Thrombin digestion of the expressed fusion protein results in an AHAS protein with an N-terminal starting at a position halfway into the transit peptide, with a residual N-terminal glycine derived from the thrombin recognition site. The final amino terminus of the cleaved AHAS protein consists of Gly-Ser-Ser-Ile-Ser. Site-directed mutations were introduced into the AHAS gene in this vector.

Site-directed mutations were constructed according to the PCR method of Higuchi (*Recombinant PCR*. In M A Innis, et al. *PCR Protocols: A Guide to Methods and Applications*, Academic Press, San Diego, pp. 177–183, 1990). Two PCR products, each of which overlap the mutation site, were amplified. The primers in the overlap region contained the mutation. The overlapping PCR amplified fragments were combined, denatured, and allowed to re-anneal together, producing two possible heteroduplex products with recessed 3'-ends. The recessed 3'-ends were extended by Taq DNA polymerase to produce a fragment that was the sum of the two overlapping PCR products containing the desired mutation. A subsequent re-amplification of this fragment with only the two "outside" primers resulted in the enrichment of the full-length product. The product containing the mutation was then re-introduced into the Arabidopsis AHAS gene in the pGEX-2T vector.

Example 3
Expression and Purification of AHAS Variants

A. Methods

*E. Coli* (DH5α) cells transformed with the pGEX-2T vector containing either the maize wild type AHAS gene (vector designation pAC751), the Arabidopsis Ser653Asn mutant, or the Arabidopsis Ile401Phe mutant were grown overnight in LB broth containing 50 μg/mL ampicillin. The overnight culture of *E. coli* was diluted 1:10 in 1 L LB, 50 μg/mL ampicillin, and 0.1% v/v antifoam A. The culture was incubated at 37° C. with shaking until the $OD_{600}$ reached approximately 0.8. Isopropylthiogalactose (IPTG) was added to a final concentration of 1 mM and the culture was incubated for 3 more hours.

Cells were harvested by centrifugation at 8,670 xg for 10 minutes in a JA-10 rotor and resuspended in 1/100th of the original culture volume in MTPBS (16 mM $Na_2HPO_4$, 4 mM $NaH_2PO_4$, 150 mM NaCl, pH 7.3). Triton X-100 and lysozyme were added to a final concentration of 1% v/v and 100 μg/mL, respectively. Cells were incubated at 30° C. for 15 minutes cooled to 4° C. on ice, and were lysed by sonication for 10 seconds at level 7 with a Branson Sonifier Cell Disrupter equipped with a microtip probe. The cell free extract was centrifuged at 35,000×g for 10 min. at 4° C. The supernatant was decanted and the centrifugation step was repeated.

Purification of expressed fusion proteins was performed as modified from Smith and Johnson (Gene 67:31–40, 1988). The supernatant was warmed to room temperature and was passed through a 2 mL column of glutathione-agarose beads (sulfur linkage, Sigma) equilibrated in MTPBS. The column was subsequently washed with MTPBS at room temperature until the $A_{280}$ of eluant matched that of MTPBS. The fusion protein was then eluted using a solution containing 5 mM reduced glutathione in 50 mM Tris HCL, pH 8.0. The eluted fusion protein was treated with approximately 30 NIH units of thrombin and dialyzed against 50 mM citrate pH 6.5 and 150 mM NaCl.

The fusion protein was digested overnight at room temperature. Digested samples were dialyzed against MTPBS and passed twice through a glutathione-agarose column equilibrated in MTPBS to remove the released glutathione transferase protein. The protein fraction that did not bind to the column was collected and was concentrated by ultrafiltration on a YM10 filter (Amicon). The concentrated sample was loaded onto a 1.5×95 cm Sepharcryl S-100 gel filtration column equilibrated in gel filtration buffer (50 mM HEPES, 150 mM NaCl, pH 7.0). Two mL fractions were collected at a flow rate of 0.14 mL/min. Enzyme stability was tested by storage of the enzyme at 4° C. in gel filtration buffer with the addition of 0.02% sodium azide and in the presence or absence of 2 mM thiamine pyrophosphate and 100 μM flavin adenine dinucleotide (FAD).

B. Results

Figure 6:
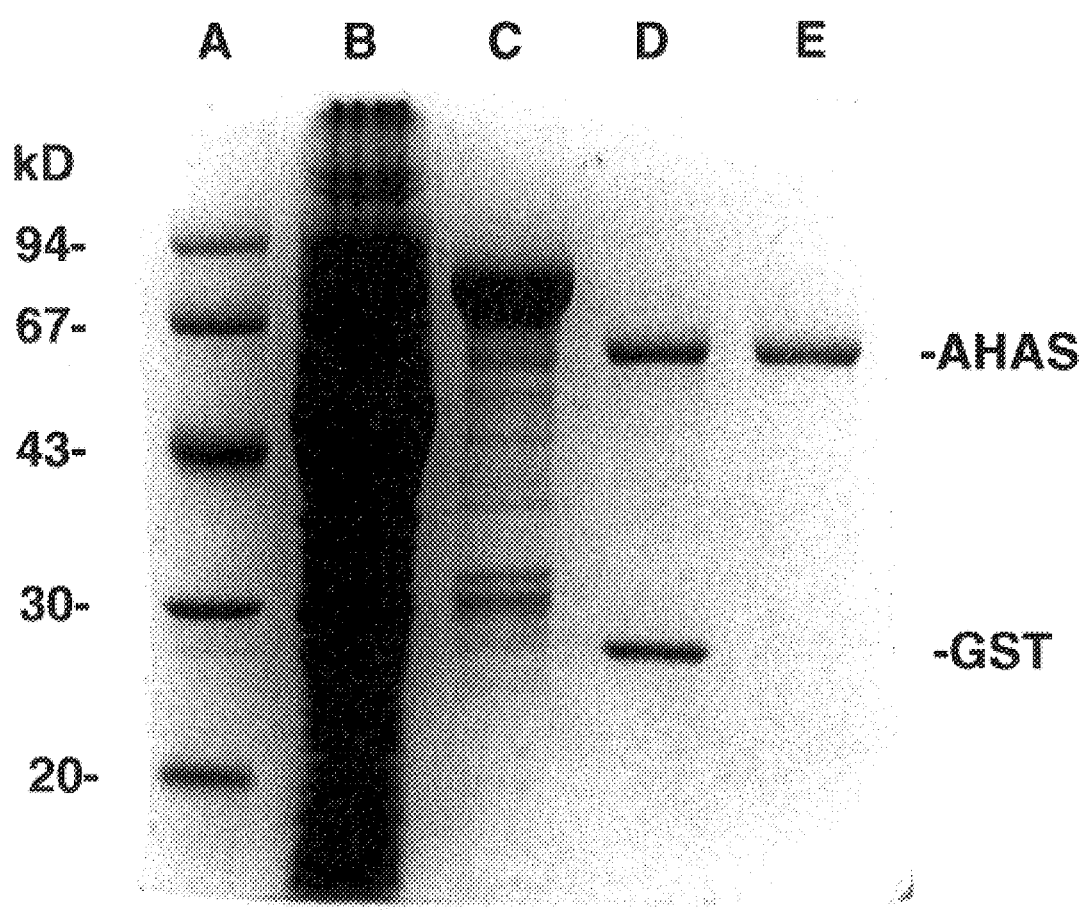

E. coli transformed with the pAC751 plasmid containing the wide-type AHAS gene fused downstream and in-frame with the GST gene expressed a 91 kD protein when induced with IPTG. The 91 kD protein exhibited the predicted molecular mass of a GST/AHAS fusion protein (the sum of (26 kD and 65 kD, respectively). When the cell free extract of DH5α/pAC751 was passed through a glutathione-agarose affinity gel, washed, and eluted with free glutathione it yielded a preparation enriched in the 91 kD protein (FIG. 6, lane C). The six amino acid thrombin recognition site engineered in the junction of GST and AHAS was successfully cleaved by thrombin (FIG. 6, lane D). The cleaved fusion protein preparation consisted of the expected 26 kD GST protein and the 65 kD maize AHAS protein. Maize AHAS was purified to homogeneity by a second pass through the glutathione-agarose column to affinity subtract GST and subjected to a final Sephacryl S-100 gel filtration step to eliminated thrombin (FIG. 6, lane E). The 65 kD protein is recognized on western blots by a monoclonal antibody raised against a maize AHAS peptide.

Purified wild type maize AHAS was analyzed by electrospray mass spectrometry and was determined to have a molecular mass of 64,996 daltons (data not shown). The predicted mass, as calculated from the deduced amino acid sequence of the gene inserted into the pGEX-2T vector, is 65,058. The 0.096% discrepancy between the empirically determined and predicted mass was within tuning variability of the mass spectrometer. The close proximity of the two mass determinations suggests that there were no misincorporated nucleotides during construction of the expression vector, nor any post-translational modifications to the protein that would cause gross changes in molecular mass. Moreover, the lack of spurious peaks in the preparation of purified enzyme indicated that the sample was free of contamination.

Example 4

Enzymatic properties of AHAS variants

The enzymatic properties of wild-type and variant AHAS produced in E. coli were measured by a modification of the method of Singh et al. (Anal. Biochem 171:173–179, 1988) as follows:

A reaction mixture containing 1X AHAS assay buffer (50 mM HEPES pH 7.0, 100 mM pyruvate, 10 mM MgCl$_2$, 1 mM thiamine pyrophosphate (TPP), and 50 μM flavin adenine dinucleotide (FAD)) was obtained either by dilution of enzyme in 2x assay buffer or by addition of concentrated enzyme to 1X AHAS assay buffer. All assays containing imazethapyr and associated controls contained a final concentration of 5% DMSO due to addition of imazethapyr to assay mixtures as a 50% DMSO solution. Assays were performed in a final volume of 250 μL at 37° C. in microtiter plates. After allowing the reaction to proceed for 60 minutes, acetolactate accumulation was measured colorimetrically as described by Singh et al., Anal. Biochem 171:173–179, 1988.

Maize AHAS expressed and purified from pAC751 as described in Example 3 above is active in the conversion of pyruvate to acetolactate. Full AHAS activity is dependent on the presence of the cofactors FAD and TPP in the assay medium. No activity was detected when only FAD was added to the assay medium. The activity of the purified enzyme with TPP only, or with no cofactors, was less than 1% of the activity detected in the presence of both TPP and FAD. Normally, AHAS present in crude plant extracts is very labile, particularly in the absence of substrate and cofactors. In contrast, the purified AHAS from the bacterial expression system showed no loss in catalytic activity when stored for one month at 4° C. in 50 mM HEPES pH 7.0, 150 mM NaCl, 0.02% NaN$_3$ in the presence or absence of FAD and TPP. Furthermore, no degradation products were visible from these stored preparations when resolved in SDS-PAGE gels.

The specific activities of wild-type AHAS and the M124E, R199A, and F206R variants are shown in Table 2 below. As determined from the alignment in FIG. 5, the M124E mutation in Arabidopsis AHAS is the equivalent of the maize M53E mutation, the R199A mutation in Arabidopsis is the equivalent of the maize R128A mutation, and the F206R mutation in Arabidopsis is the equivalent of the maize F135R mutation. The mutations designed in the maize AHAS structural model were used to identify the equivalent amino acid in the dicot Arabidopsis AHAS gene and were incorporated and tested in the Arabidopsis AHAS gene. This translation and incorporation of rationally designed herbicide mutations into the dicot Arabidopsis AHAS gene can facilitate evaluation of herbicide resistance in plants of a dicot species.

TABLE 2

| | SPECIFIC ACTIVITY | |
|---|---|---|
| | Specific Activity | % Catalytic Activity as Compared to Wild Type |
| Wild-Type | 147 | 100 |
| Met124Glu | 13.5 | 9.2 |
| Arg199Ala | 127 | 86 |
| Phe206Arg | 7.49 | 5.1 |

Figure 7:
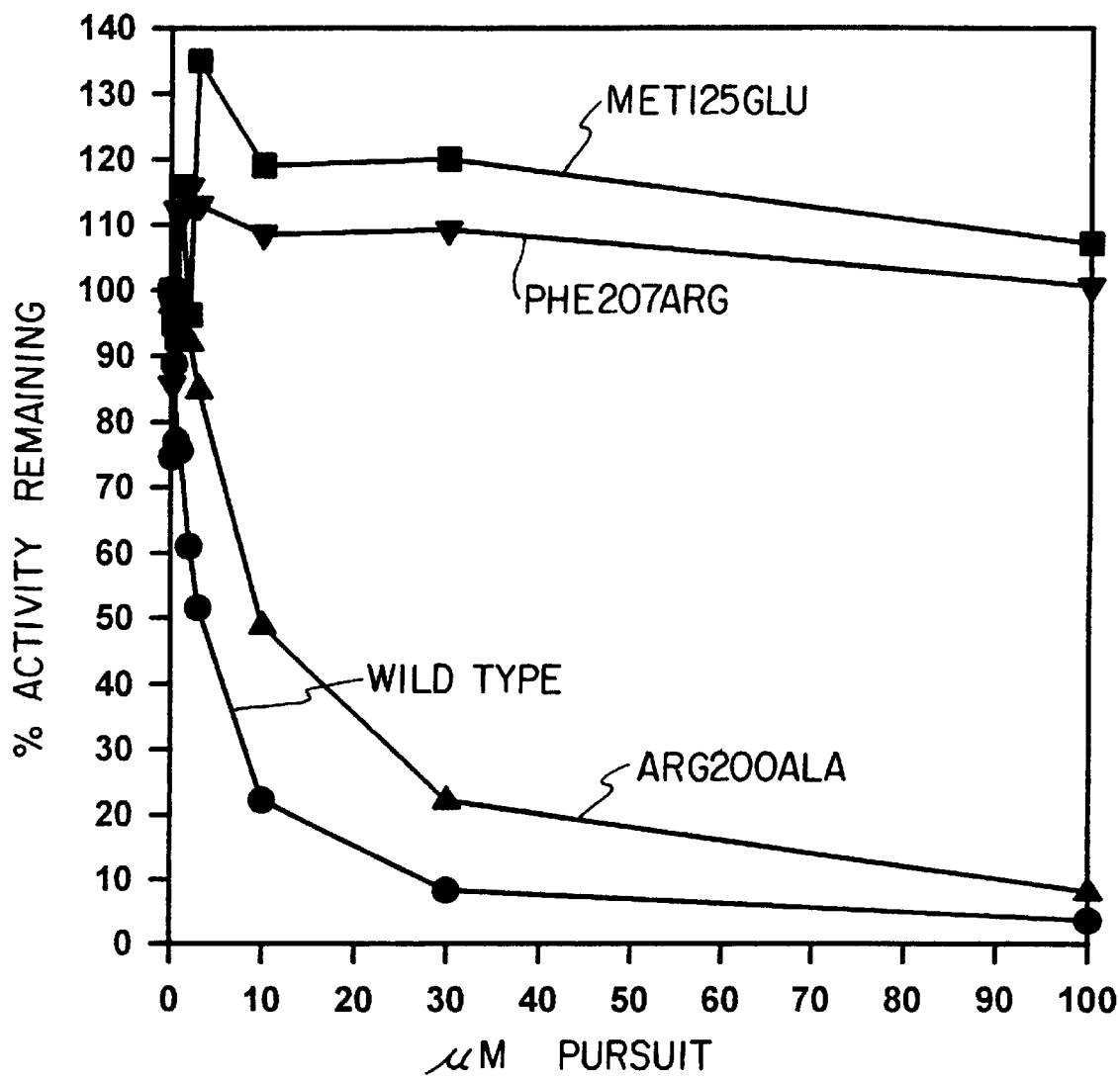
Figure 8:
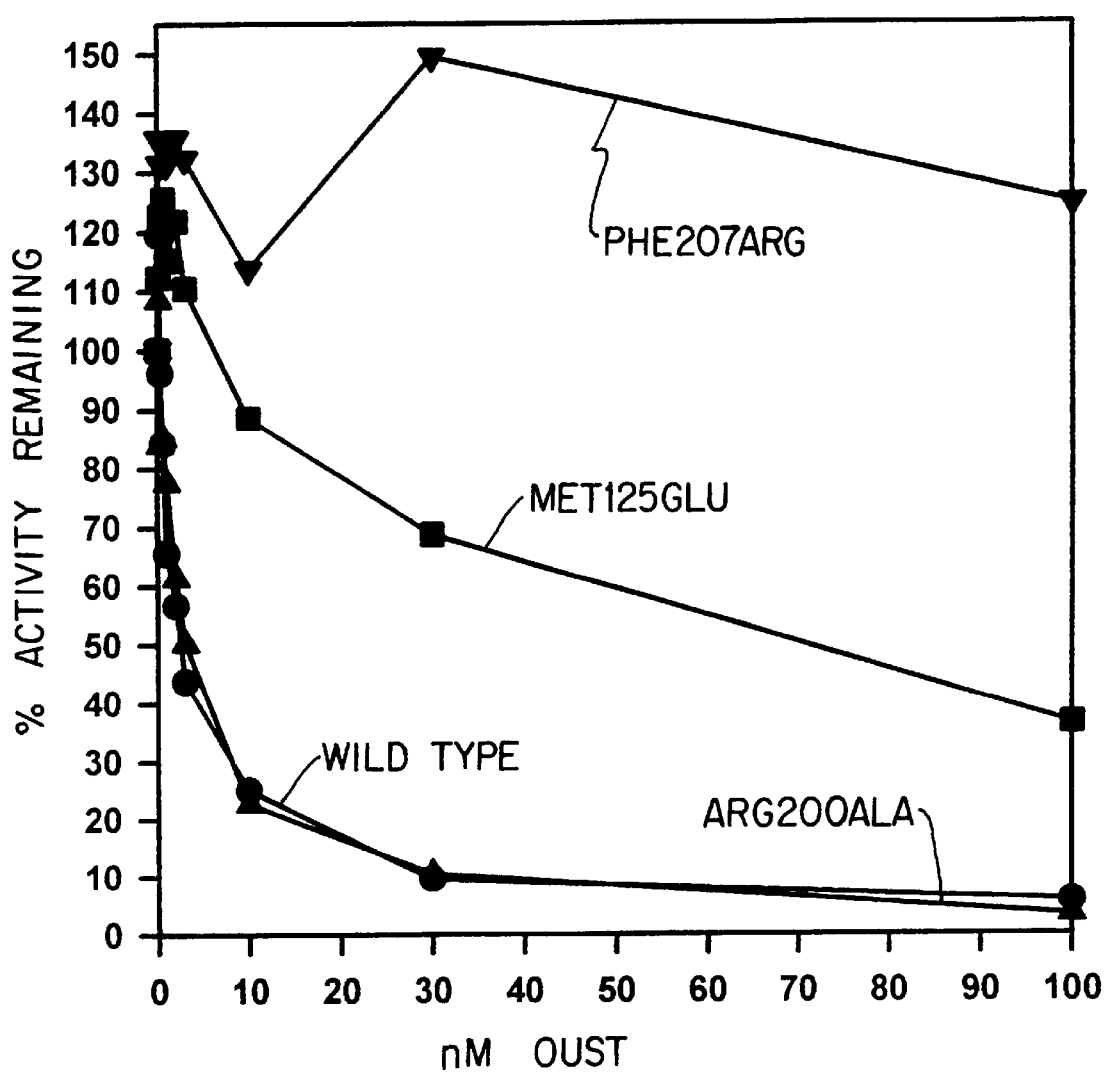

The R199A mutation maintains a high level of catalytic activity (Table 2) while exhibiting a significant level of resistance to imazethapyr (FIG. 7). Notably, this variant retains complete sensitivity to sulfonylureas (FIG. 8). Thus, this variant fulfills the criteria of high specific activity and selective herbicide resistance. By contrast, the M124E substitution resulted in almost complete resistance to imazethapyr (FIG. 7) but also exhibited severely reduced catalytic activity (Table 2). Relative to imidazolinone resistance, this variant exhibits greater sensitivity to sulfonylurea (FIG. 8), suggesting that this residue is a good candidate for creating a mutation that confers selective resistance. Substitution of an amino acid other than glutamic acid may help to maintain catalytic activity. The F206R substitution yielded similar results to those observed with M124E variant, but lacked selectivity in resistance.

Example 5

Iterative Improvement of AHAS Herbicide-Resistant Variant Using a Rational Design Approach Changing residue 124 in AHAS from Met to Glu as described in Example 4 above conferred imidazolinone resistance but also reduced enzymatic activity to 9.2% of the wild type value. The model of the maize AHAS structure described above suggested that Met53 (equivalent to the Arabidopsis Met124 residue) interacts with a series of hydrophobic residues on the face of an α-helix that is derived from a separate subunit but are in close proximity to Met53. Thus, the hydrophobic interaction between Met53 and the residues on the helix may stabilize both subunit/ subunit association and the conformation of the active site. It was believed that the substitution of the hydrophobic Met residue with a charged glutamate residue most probably destabilizes the inter-subunit hydrophobic interaction and results in a loss of catalytic activity.

Figure 9:
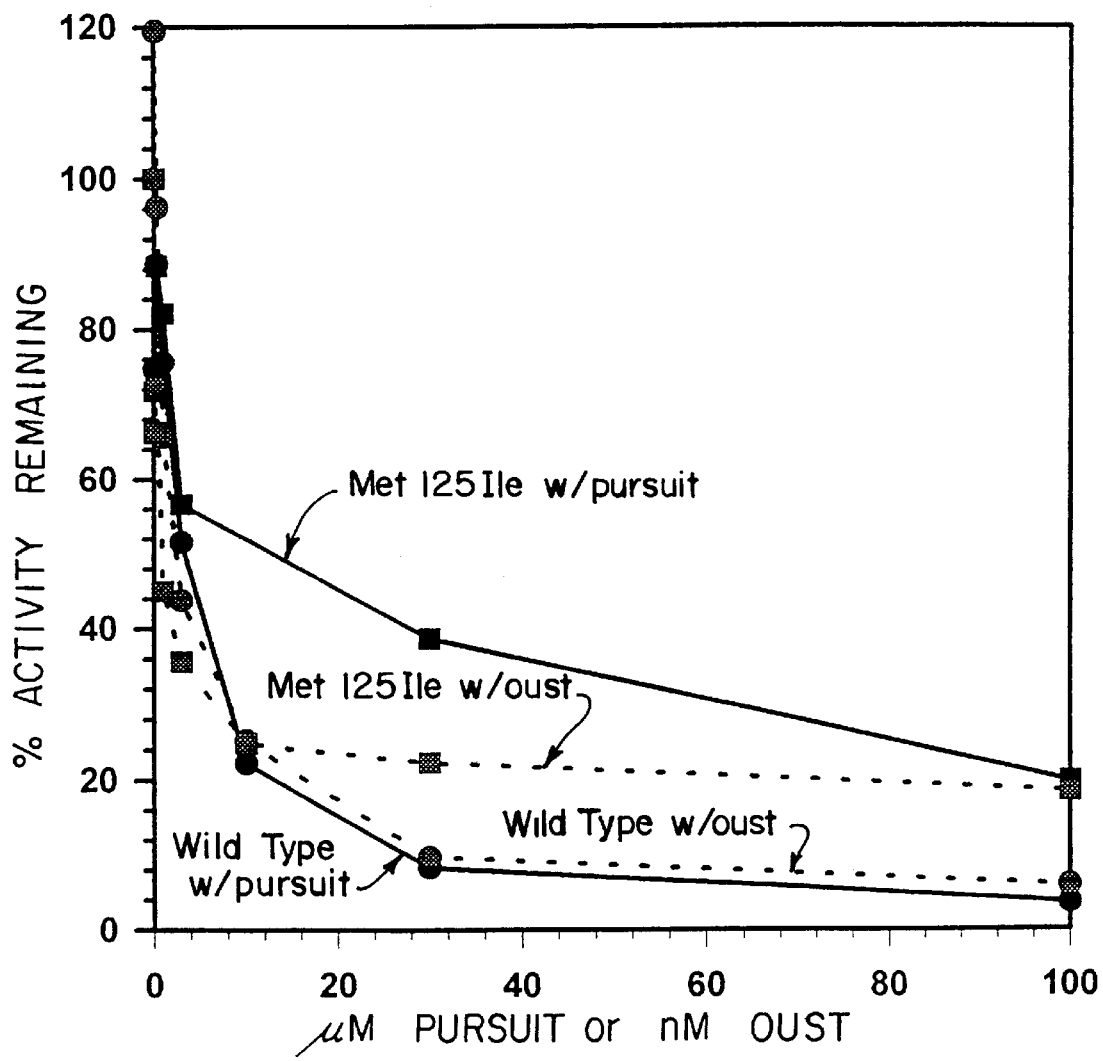

Based on this structure/function analysis, the activity of the original Arabidopsis Met124Glu (equivalent to maize Met53Glu) mutant enzyme was then iteratively improved by substituting a more hydrophobic amino acid (Ile) at this position. The hydrophobic nature of the Ile side chain resulted in restoration of activity to wild type levels (specific activity of 151, equivalent to 103% of the wild-type activity), but the greater bulk of the Ile side chain was still able to maintain a significant level of imidazolinone resistance (FIG. 9).

Example 6
Iterative Improvement of AHAS Herbicide-Resistant Variant Using a Rational Design Approach Another example of iterative refmement using the methods of the present invention involves the Arg128Ala variant. The structural model of maize AHAS suggested that the Arg128 residue, which resides at the lip of the herbicide binding pocket, contributes to channeling charged substrates and herbicides into the herbicide binding pocket and into the active site. The Arg 128 residue is distant from the TPP moiety, which binds the initial pyruvate molecule in the reaction mechanism of AHAS, explaining why the substitution of Arabidopsis AHAS Arg199, the equivalent to maize Arg128 to alanine, had little effect on the catalytic activity of the enzyme. The structural model further indicated that a more radical change could be made at this position to raise the level of resistance while maintaining high levels of catalytic activity. On this basis, an iterative improvement of the mutation was made to substitute the positively charge arginine residue with a negatively charged glutamate residue. The enzyme thus mutated had improved levels of resistance to PURSUIT® while maintaining high levels of activity (specific activity of 168, equivalent to 114% of the wild-type activity) (FIG. 10).

Example 7

Interchangeability of AHAS Derived From Different Species in Structure Based Rational Design of Herbicide-Resistant AHAS Variants A structural model of the three-dimensional structure of AHAS is built with a monocot AHAS sequence such as that derived from maize, as described above. To introduce mutations into AHAS derived from a dicot species such as Arabidopsis, the sequences of AHAS derived from the monocot and dicot species are aligned using the GAP and PILEUP programs (Genetics Computer Group, 575 Sequence Drive, Modeom, Wis. 53711). Equivalent positions are determined from the computer-generated alignment. The mutations are then introduced into the dicot AHAS gene as described above. Following expression of the mutant AHAS protein in *E.Coli* and assessment of its biochemical properties (i.e., specific activity and resistance to herbicides), the mutant gene is introduced into a dicot plant by plant transformation methods as described above.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A structure-based modelling method for identifying potential herbicide resistant acetohydroxy acid synthase (AHAS) variant proteins, said method comprising:

(a) modelling a target AHAS protein on a template selected from the group consisting of pyruvate oxidase, transketolase, carboligase, and pyruvate decarboxylase, wherein said modelling comprises (i) aligning the primary sequence of said target AHAS protein on the sequence of said template by pair-wise sequence alignment to achieve a maximal homology score followed by repositioning gaps to conserve continuous regular secondary structures; (ii) transposing said aligned sequence to the three-dimensional struture of said template to derive the three-dimensional struture of said target AHAS protein; (iii) subjecting the structure obtained in step (ii) to energy minization; and (iv) localizing an herbicide binding pocket in said three-dimensional structure;

(b) positioning and herbicide into the three-dimensional structure of said target AHAS protein using interactive molecular graphics wherein said herbicide is selected from the group consisting of imidazolinones, sulfonylureas, triazolopyrimidine sulfonamides, pyrimidyl-oxy-benzoic acids, sulfmoylureas, and sulfonylcarboximides;

(c) selecting as a target for a mutation, an amino acid position in said target AHAS protein, wherein the amino acid at said position is predicted, based on the structure obtained in (a), to participate directly or indirectly in herbicide binding;

(d) mutating DNA encoding said target AHAS protein to produce a mutated DNA encoding a variant AHAS containing said tergeted mutation at said position;

(e) expressing said mutated DNA in a first cell, under conditions in which said variant AHAS containing said mutation at said position is produced;

(f) expressing DNA encoding wild-type AHAS in parallel in a second cell;

(g) purifying said wild-type and said variant AHAS proteins from said cells;

(h) assaying said wild-type and said variant AHAS proteins for catalytic activity in the conversion of pyruvate to acetolactate or in the condensation of pyravate and 2-ketobutyrate to form acetohydroxybutyrate, in the absence and in the presence of at least one of said herbicides;

(i) obtaining a three-dimensional structure of said variant AHAS by (i) introducing the mutation produced in step (d) into the target AHAS structure obtained in step (a); (ii) subjecting the resulting structure to energy minimization; and (iii) localizing the herbicide-binding pocket in the resulting three-dimensional structure;

(j) repeating steps (c)–(i), wherein said variant is used as the target AHAS in step (c) and other mutations are made until an herbicide resistant AHAS variant protein is identified having;

(1) in the absence of an herbicide, (A) a catalytic activity alone sufficient to maintain the viability of a cell in which it is expressed; or (B) catalytic activity in combination with any herbicide resistant AHAS variant protein also expressed in said cell, which may be the same as or different than said first AHAS variant protein, sufficient to maintain the viability of a cell in which it is expressed;

wherein said cell requires AHAS activity for viability; and (2) catalytic activity that is morc resistant to at least one herbicide than is wild type AHAS.

2. A structure-based modelling method as defined in claim 1, wherein said catalytic activity in the absence of said more than one herbicide is more than about 20% of the catalytic activity of said wild-type AHAS in the absence of said at least one herbicide.

3. A structure-based modelling method as defmed in claim 2, wherein said herbicide is an imidazolinone herbicide and said herbicide-resistant AHAS variant protein has:

(i) catalytic activity in the absence of said herbicide of more than about 20% of the catalytic activity of said wild-type AHAS;

(ii) catalytic activity that is more resistant to the presence of imidazolinone herbicides compared to wild type AHAS; and (iii) catalytic activity that is relatively more sensitive to the presence of sulfonylurea herbicides compared to imidazolinone herbicides.

4. A structure-based modelling method for identifying potential herbicide resistant acetohydroxy acid synthase (AHAS) variant protein, said method comprising:

(a) modelling a target AHAS protein on template selected from the group consisting of pyruvate oxidase, transketolase, carboligase, and pyruvate decarboxylase, wherein said modelling comprises (i) aligning the primary sequence of said target AHAS protein on the sequence of said template by pair-wise sequence alignment to achieve a maximal homology score followed by repositioning gaps to conserve continuous regular sencondary structures; (ii) transposing said aligned sequence to the three-dimensional structure of said template to derive the three-dimensional structure of said target AHAS protein; (iii) subjecting the structure obtained in step (ii) to energy minimization; and (iv) localizing an herbicide binding pocket in said three-dimensional structure;

(b) positioning an herbicide into the three-dimensional structure of said target AHAS protein using interactive molecular graphics, wherein said herbicide is selected from the group consisting of imidazolinones, sulfonylureas, triazolopyrimidine sulfonamides, pyrimidyl-oxy-benzoic acids, sulfamoylureas, and sulfonylcarboximides;

(c) selecting as a target for a mutation an amino acid position in said target AHAS protein, wherein the amino acid at said position is predicted, based on the structure obtained in (a), to participate directly or indirectly in herbicide binding;

(d) mutating DNA encoding said target AHAS protein to produce a mutated DNA encoding a variant AHAS containing said targeted mutation at said position;

(e) expressing said mutated DNA in a cell, under conditions in which said variant AHAS containing said mutation at said position is produced, and (f) comparing catalytic activity and herbicide sensitivity of said expressed variant AHAS with that of wild-type AHAS.

5. A structure-based modelling method as defmed in claim 1, wherein said target AHAS protein is derived from *Arabidopsis thaliana.*

6. A structure-based modelling method as defined in claim 1, wherein said cell is *E. coli.*

7. A structure-based modelling method as defined in claim 1, wherein said target AHAS protein comprises a protein having the sequence of FIG. 1 SEQ ID NO:1.

8. A structure-based modelling method as defined in claim 1, wherein said mutation is selected from the group consisting of (i) substitution of at least one different amino acid residue at an amino acid position of the sequence of FIG. 1, SEQ ID NO:1, selected from the group consisting of P48, G49, S52, M53, E54, A95, T96, S97, G98, P99, G100, A101, V125, R127, R128, M129, I130, G131, T132, D133, F135, Q136, D186, I117, T259, T260, L261, M262, G263, R276, M277, L278, G279, H281, G282, T283, V284, G300, V301, R302, F303, D304, R306, V307, T308, G309, K310, I311, E312, A313, E329, I330, K332, N333, K334, Q335, T404, G413, V414, G415, M419, L434, S435, S436, A437, G438, L439, G440, A441, M442, G443, L497, G498, M499, V501, Q502, Q504, D505, R506, Y508, K509, H575, V576, L577, P578, M579, I580, P581, G583, and G584, and any combination of any of the foregoing;

(ii) deletion of at least one amino acid residue between positions Q124 and H150 of the sequence of FIG. 1, SEQ ID NO:1;

(iii) addition of at least one amino acid residue between positions Q124 and H150 of the sequence of FIG. 1, SEQ ID NO:1; or (iv) any combination of any of the foregoing.

9. A structure-based modelling method as defined in claim 11, wherein said substitution is selected from the group consisting of Met53Trp, Met53Glu, Met53Ile, Arg128Ala, Arg128Glu, Phe135Arg, Ile330Phe, or a combination of any of the foregoing.

10. A structure-based modelling method for identifying potential herbicide-resistant acetohydroxy acid synthase (AHAS) variant proteins, said method comprising:

(a) modelling a target AHAS protein on a template selected from the group consisting of pyruvate oxidase, transketolase, carboligase, and pyruvate decarboxylase, wherein said modelling comprises (i) aligning the primary sequence of said target AHAS protein on the sequence of said template by pair-wise sequence alignment to achieve a maximal homology score followed by repositioning gaps to conserve continuous regular secondary structures; (ii) transposing said aligned sequence to the three-dhnensional structure of said template to derive the three-dimensional structure of said target AHAS protein; (iii) subjecting the structure obtained in step (ii) to energy minimization; and (iv) localizing an herbicide binding pocket in said three-dimensional structure;

(b) positioning an herbicide into the three-dimensional structure of said target AHAS protein using interactive molecular graphics, wherein said herbicide is selected from the group consisting of imidazolinones, sulfonylureas, triazolopyrimidine sulfonamides, pyrimidyl-oxy-benzoic acids, sulfamoylureas, and sulfonylcarboximides;

(c) selecting as a target for a mutation, an amino acid position in said target AHAS protein, wherein the amino acid at said position is predicted, based on the structure obtained in (a), to participate directly or indirectly in herbicide binding;

(d) mutating DNA encoding said target AHAS protein to produce a mutated DNA encoding a variant AHAS containing said targeted mutation at said position;

(e) expressing said mutated DNA in a first cell, under conditions in which said variant AHAS containing said mutation at said position is produced, (f) expressing DNA encoding wild-type AHAS in parallel in a second cell;

(g) purifying said wild-type and said variant AHAS proteins from said cells;

(i) assaying said wild-type and said variant AHAS proteins for catalytic activity in the conversion of pyruvate to acetolactate or in the condensation of pyruvate and 2-ketobutyrate to form acetohydroxybutyrate, in the absence and in the presence of at least one of said herbicides; and (j) repeating steps (d)–(i), wherein said DNA encoding said variant of step (e) is used as the AHAS-encoding DNA in step (d) and other mutations are made at said position until a first herbicide resistant AHAS variant protein is identified having:

(1) in the absence of an herbicide, (A) a catalytic activity alone sufficient to maintain the viability of a cell in which it is expressed; or (B) catalytic activity in combination with any herbicide resistant AHAS variant protein also expressed in said cell, which may be the same as or different than said first AHAS variant protein sufficient to maintain the viability of a cell in which it is expressed;

wherein said cell requires AHAS activity for viability; and (2) catalytic activity that is more resistant to at least one herbicide than is wild type AHAS.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 599 amino acids
( B ) TYPE: amino acid
( C ) STRANDEDNESS:
( D ) TOPOLOGY: linear ( i i ) MOLECULE TYPE: protein ( i i i ) HYPOTHETICAL: NO ( v i ) ORIGINAL SOURCE:
( A ) ORGANISM: Zea mays ( x i ) SEQUENCE DESCRIPTION: SEQ ID NO:1:

```
Gly Ser Ala Ala Ser Pro Ala Met Pro Met Ala Pro Pro Ala Thr Pro
1               5                   10                  15

Leu Arg Pro Trp Gly Pro Thr Asp Pro Arg Lys Gly Ala Asp Ile Leu
            20                  25                  30

Val Glu Ser Leu Glu Arg Cys Gly Val Arg Asp Val Phe Ala Tyr Pro
        35                  40                  45

Gly Gly Ala Ser Met Glu Ile His Gln Ala Leu Thr Arg Ser Pro Val
    50                  55                  60
```

```
Ile  Ala  Asn  His  Leu  Phe  Arg  His  Glu  Gln  Gly  Glu  Ala  Phe  Ala  Ala
65                       70                  75                       80

Ser  Gly  Tyr  Ala  Arg  Ser  Ser  Gly  Arg  Val  Gly  Val  Cys  Ile  Ala  Thr
                    85                  90                            95

Ser  Gly  Pro  Gly  Ala  Thr  Asn  Leu  Val  Ser  Ala  Leu  Ala  Asp  Ala  Leu
               100                 105                       110

Leu  Asp  Ser  Val  Pro  Met  Val  Ala  Ile  Thr  Gly  Gln  Val  Pro  Arg  Arg
          115                      120                       125

Met  Ile  Gly  Thr  Asp  Ala  Phe  Gln  Glu  Thr  Pro  Ile  Val  Glu  Val  Thr
     130                      135                      140

Arg  Ser  Ile  Thr  Lys  His  Asn  Tyr  Leu  Val  Leu  Asp  Val  Asp  Asp  Ile
145                      150                 155                          160

Pro  Arg  Val  Val  Gln  Glu  Ala  Phe  Phe  Leu  Ala  Ser  Ser  Gly  Arg  Pro
                    165                      170                      175

Gly  Pro  Val  Leu  Val  Asp  Ile  Pro  Lys  Asp  Ile  Gln  Gln  Met  Ala
               180                      185                      190

Val  Pro  Val  Trp  Asp  Lys  Pro  Met  Ser  Leu  Pro  Gly  Tyr  Ile  Ala  Arg
               195                 200                 205

Leu  Pro  Lys  Pro  Pro  Ala  Thr  Glu  Leu  Leu  Glu  Gln  Val  Leu  Arg  Leu
     210                      215                 220

Val  Gly  Glu  Ser  Arg  Arg  Pro  Val  Leu  Tyr  Val  Gly  Gly  Gly  Cys  Ala
225                      230                 235                          240

Arg  Ser  Gly  Glu  Glu  Leu  Arg  Arg  Phe  Val  Glu  Leu  Thr  Gly  Ile  Pro
                    245                      250                      255

Val  Thr  Thr  Thr  Leu  Met  Gly  Leu  Gly  Asn  Phe  Pro  Ser  Asp  Asp  Pro
               260                 265                      270

Leu  Ser  Leu  Arg  Met  Leu  Gly  Met  His  Gly  Thr  Val  Tyr  Ala  Asn  Tyr
          275                 280                      285

Ala  Val  Asp  Lys  Ala  Asp  Leu  Leu  Ala  Leu  Gly  Val  Arg  Phe  Asp
     290                 295                      300

Asp  Arg  Val  Thr  Gly  Lys  Ile  Glu  Ala  Phe  Ala  Ser  Arg  Ala  Lys  Ile
305                      310                 315                          320

Val  His  Val  Asp  Ile  Asp  Pro  Ala  Glu  Ile  Gly  Lys  Asn  Lys  Gln  Pro
               325                      330                      335

His  Val  Ser  Ile  Cys  Ala  Asp  Val  Lys  Leu  Ala  Leu  Gln  Gly  Met  Asn
               340                      345                      350

Ala  Leu  Leu  Glu  Gly  Ser  Thr  Ser  Lys  Lys  Ser  Phe  Asp  Phe  Gly  Ser
          355                      360                 365

Trp  Asn  Asp  Glu  Leu  Asp  Gln  Gln  Lys  Arg  Glu  Phe  Pro  Leu  Gly  Tyr
     370                      375                 380

Lys  Tyr  Ser  Asn  Glu  Glu  Ile  Gln  Pro  Gln  Tyr  Ala  Ile  Gln  Val  Leu
385                      390                 395                          400

Asp  Glu  Leu  Thr  Lys  Gly  Glu  Ala  Ile  Ile  Gly  Thr  Gly  Val  Gly  Gln
                    405                      410                      415

His  Gln  Met  Trp  Ala  Ala  Gln  Tyr  Tyr  Thr  Tyr  Lys  Arg  Pro  Arg  Gln
               420                      425                 430

Trp  Leu  Ser  Ser  Ala  Gly  Leu  Gly  Ala  Met  Gly  Phe  Gly  Leu  Pro  Ala
          435                      440                 445

Ala  Ala  Gly  Ala  Ser  Val  Ala  Asn  Pro  Gly  Val  Thr  Val  Val  Asp  Ile
     450                      455                 460

Asp  Gly  Asp  Gly  Ser  Phe  Leu  Met  Asn  Val  Gln  Glu  Leu  Ala  Met  Ile
465                      470                      475                      480

Arg  Ile  Glu  Asn  Leu  Pro  Val  Lys  Val  Phe  Val  Leu  Asn  Asn  Gln  His
                    485                      490                      495
```

| | | | | | | | | | | | | | | | |
|---|---|---|---|---|---|---|---|---|---|---|---|---|---|---|---|
|Leu|Gly|Met|Val<br>500|Val|Gln|Trp|Glu|Asp<br>505|Arg|Phe|Tyr|Lys|Ala<br>510|Asn|Arg|
|Ala|His|Thr<br>515|Tyr|Leu|Gly|Asn|Pro<br>520|Glu|Asn|Glu|Ser|Glu<br>525|Ile|Tyr|Pro|
|Asp|Phe<br>530|Val|Thr|Ile|Ala|Lys<br>535|Gly|Phe|Asn|Ile|Pro<br>540|Ala|Val|Arg|Val|
|Thr<br>545|Lys|Lys|Asn|Glu|Val<br>550|Arg|Ala|Ala|Ile|Lys<br>555|Lys|Met|Leu|Glu|Thr<br>560|
|Pro|Gly|Pro|Tyr|Leu<br>565|Leu|Asp|Ile|Ile|Val<br>570|Pro|His|Gln|Glu|His<br>575|Val|
|Leu|Pro|Met|Ile<br>580|Pro|Ser|Gly|Gly|Ala<br>585|Phe|Lys|Asp|Met|Ile<br>590|Leu|Asp|
|Gly|Asp|Gly<br>595|Arg|Thr|Val|Tyr| | | | | | | | | |

( 2 ) INFORMATION FOR SEQ ID NO:2:

( i ) SEQUENCE CHARACTERISTICS:
        ( A ) LENGTH: 585 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Lactobacillus plantarum ( x i ) SEQUENCE DESCRIPTION: SEQ ID NO:2:

| | | | | | | | | | | | | | | | |
|---|---|---|---|---|---|---|---|---|---|---|---|---|---|---|---|
|Thr<br>1|Asn|Ile|Leu|Ala<br>5|Gly|Ala|Ala|Val|Ile<br>10|Lys|Val|Leu|Glu|Ala<br>15|Trp|
|Gly|Val|Asp|His<br>20|Leu|Tyr|Gly|Ile|Pro<br>25|Gly|Gly|Ser|Ile|Asn<br>30|Ser|Ile|
|Met|Asp|Ala<br>35|Leu|Ser|Ala|Glu|Arg<br>40|Asp|Arg|Ile|His|Tyr<br>45|Ile|Gln|Val|
|Arg|His<br>50|Glu|Glu|Val|Gly|Ala<br>55|Met|Ala|Ala|Ala|Ala<br>60|Asp|Ala|Lys|Leu|
|Thr<br>65|Gly|Lys|Ile|Gly|Val<br>70|Cys|Phe|Gly|Ser|Ala<br>75|Gly|Pro|Gly|Gly|Thr<br>80|
|His|Leu|Met|Asn|Gly<br>85|Leu|Tyr|Asp|Ala|Arg<br>90|Glu|Asp|His|Val|Pro<br>95|Val|
|Leu|Ala|Leu|Ile<br>100|Gly|Gln|Phe|Gly|Thr<br>105|Thr|Gly|Met|Asn|Met<br>110|Asp|Thr|
|Phe|Gln|Glu<br>115|Met|Asn|Glu|Asn|Pro<br>120|Ile|Tyr|Ala|Asp|Val<br>125|Ala|Asp|Tyr|
|Asn|Val<br>130|Thr|Ala|Val|Asn|Ala<br>135|Ala|Thr|Leu|Pro|His<br>140|Val|Ile|Asp|Glu|
|Ala<br>145|Ile|Arg|Arg|Ala|Tyr<br>150|Ala|His|Gln|Gly|Val<br>155|Ala|Val|Val|Gln|Ile<br>160|
|Pro|Val|Asp|Leu|Pro<br>165|Trp|Gln|Gln|Ile|Ser<br>170|Ala|Glu|Asp|Trp|Tyr<br>175|Ala|
|Ser|Ala|Asn|Asn<br>180|Tyr|Gln|Thr|Pro|Leu<br>185|Leu|Pro|Glu|Pro|Asp<br>190|Val|Gln|
|Ala|Val|Thr<br>195|Arg|Leu|Thr|Gln|Thr<br>200|Leu|Leu|Ala|Ala|Glu<br>205|Arg|Pro|Leu|
|Ile|Tyr|Tyr|Gly|Ile|Gly|Ala|Arg|Lys|Ala|Gly|Lys|Glu|Leu|Glu|Gln|

|     |     |     |     |     |     |     |     |     |     |     |     |     |     |     |
| --- | --- | --- | --- | --- | --- | --- | --- | --- | --- | --- | --- | --- | --- | --- |
|     |     | 210 |     |     |     | 215 |     |     |     | 220 |     |     |     |     |
| Leu 225 | Ser | Lys | Thr | Leu | Lys 230 | Ile | Pro | Leu | Met | Ser 235 | Thr | Tyr | Pro | Ala | Lys 240 |
| Gly | Ile | Val | Ala | Asp 245 | Arg | Tyr | Pro | Ala | Tyr 250 | Leu | Gly | Ser | Ala | Asn 255 | Arg |
| Val | Ala | Gln | Lys 260 | Pro | Ala | Asn | Glu | Ala 265 | Leu | Ala | Gln | Ala | Asp 270 | Val | Val |
| Leu | Phe | Val 275 | Gly | Asn | Asn | Tyr | Pro 280 | Phe | Ala | Glu | Val | Ser 285 | Lys | Ala | Phe |
| Lys | Asn 290 | Thr | Arg | Tyr | Phe | Leu 295 | Gln | Ile | Asp | Ile | Asp 300 | Pro | Ala | Lys | Leu |
| Gly 305 | Lys | Arg | His | Lys | Thr 310 | Asp | Ile | Ala | Val | Leu 315 | Ala | Asp | Ala | Gln | Lys 320 |
| Thr | Leu | Ala | Ala | Ile 325 | Leu | Ala | Gln | Val | Ser 330 | Glu | Arg | Glu | Ser | Thr 335 | Pro |
| Trp | Trp | Gln | Ala 340 | Asn | Leu | Ala | Asn | Val 345 | Lys | Asn | Trp | Arg | Ala 350 | Tyr | Leu |
| Ala | Ser | Leu 355 | Glu | Asp | Lys | Gln | Glu 360 | Gly | Pro | Leu | Gln | Ala 365 | Tyr | Gln | Val |
| Leu | Arg 370 | Ala | Val | Asn | Lys | Ile 375 | Ala | Glu | Pro | Asp | Ala 380 | Ile | Tyr | Ser | Ile |
| Asp 385 | Val | Gly | Asp | Ile | Asn 390 | Leu | Asn | Ala | Asn | Arg 395 | His | Leu | Lys | Leu | Thr 400 |
| Pro | Ser | Asn | Arg | His 405 | Ile | Thr | Ser | Asn | Leu 410 | Phe | Ala | Thr | Met | Gly 415 | Val |
| Gly | Ile | Pro | Gly 420 | Ala | Ile | Ala | Ala | Lys 425 | Leu | Asn | Tyr | Pro | Glu 430 | Arg | Gln |
| Val | Phe | Asn 435 | Leu | Ala | Gly | Asp | Gly 440 | Gly | Ala | Ser | Met | Thr 445 | Met | Gln | Asp |
| Leu | Val 450 | Thr | Gln | Val | Gln | Tyr 455 | His | Leu | Pro | Val | Ile 460 | Asn | Val | Val | Phe |
| Thr 465 | Asn | Cys | Gln | Tyr | Gly 470 | Phe | Ile | Lys | Asp | Glu 475 | Gln | Glu | Asp | Thr | Asn 480 |
| Gln | Asn | Asp | Phe | Ile 485 | Gly | Val | Glu | Phe | Asn 490 | Asp | Ile | Asp | Phe | Ser 495 | Lys |
| Ile | Ala | Asp | Gly 500 | Val | His | Met | Gln | Ala 505 | Phe | Arg | Val | Asn | Lys 510 | Ile | Glu |
| Gln | Leu | Pro 515 | Asp | Val | Phe | Glu | Gln 520 | Ala | Lys | Ala | Ile | Gln 525 | His | Glu |
| Pro | Val 530 | Leu | Ile | Asp | Ala | Val 535 | Ile | Thr | Gly | Asp | Arg 540 | Pro | Leu | Pro | Ala |
| Glu 545 | Lys | Leu | Arg | Leu | Asp 550 | Ser | Ala | Met | Ser | Ser 555 | Ala | Ala | Asp | Ile | Glu 560 |
| Ala | Phe | Lys | Gln | Arg 565 | Tyr | Glu | Ala | Gln | Asp 570 | Leu | Gln | Pro | Leu | Ser 575 | Thr |
| Tyr | Leu | Lys | Gln 580 | Phe | Gly | Leu | Asp | Asp 585 |     |     |     |     |     |     |     |

( 2 ) INFORMATION FOR SEQ ID NO:3:

( i ) SEQUENCE CHARACTERISTICS:
        ( A ) LENGTH: 599 amino acids
        ( B ) TYPE: amino acid
        ( C ) STRANDEDNESS: single
        ( D ) TOPOLOGY: linear (ii) MOLECULE TYPE: protein (iii) HYPOTHETICAL: NO (iv) ANTI-SENSE: NO (vi) ORIGINAL SOURCE:
    (A) ORGANISM: Zea mays (xi) SEQUENCE DESCRIPTION: SEQ ID NO:3:

```
Gly Ser Ala Ala Ser Pro Ala Met Pro Met Ala Pro Pro Ala Thr Pro
 1               5                  10                  15

Leu Arg Pro Trp Gly Pro Thr Asp Pro Arg Lys Gly Ala Asp Ile Leu
                20                  25                  30

Val Glu Ser Leu Glu Arg Cys Gly Val Arg Asp Val Phe Ala Tyr Pro
            35                  40                  45

Gly Gly Ala Ser Met Glu Ile His Gln Ala Leu Thr Arg Ser Pro Val
        50                  55                  60

Ile Ala Asn His Leu Phe Arg His Glu Gln Gly Glu Ala Phe Ala Ala
65                  70                  75                  80

Ser Gly Tyr Ala Arg Ser Ser Gly Arg Val Gly Val Cys Ile Ala Thr
                85                  90                  95

Ser Gly Pro Gly Ala Thr Asn Leu Val Ser Ala Leu Ala Asp Ala Leu
            100                 105                 110

Leu Asp Ser Val Pro Met Val Ala Ile Thr Gly Gln Val Pro Arg Arg
        115                 120                 125

Met Ile Gly Thr Asp Ala Phe Gln Glu Thr Pro Ile Val Glu Val Thr
    130                 135                 140

Arg Ser Ile Thr Lys His Asn Tyr Leu Val Leu Asp Val Asp Asp Ile
145                 150                 155                 160

Pro Arg Val Val Gln Glu Ala Phe Phe Leu Ala Ser Ser Gly Arg Pro
                165                 170                 175

Gly Pro Val Leu Val Asp Ile Pro Lys Asp Ile Gln Gln Met Ala
            180                 185                 190

Val Pro Val Trp Asp Lys Pro Met Ser Leu Pro Gly Tyr Ile Ala Arg
        195                 200                 205

Leu Pro Lys Pro Pro Ala Thr Glu Leu Leu Glu Gln Val Leu Arg Leu
    210                 215                 220

Val Gly Glu Ser Arg Arg Pro Val Leu Tyr Val Gly Gly Gly Cys Ala
225                 230                 235                 240

Ala Ser Gly Glu Glu Leu Arg Arg Phe Val Glu Leu Thr Gly Ile Pro
                245                 250                 255

Val Thr Thr Thr Leu Met Gly Leu Gly Asn Phe Pro Ser Asp Asp Pro
            260                 265                 270

Leu Ser Leu Arg Met Leu Gly Met His Gly Thr Val Tyr Ala Asn Tyr
        275                 280                 285

Ala Val Asp Lys Ala Asp Leu Leu Leu Ala Leu Gly Val Arg Phe Asp
    290                 295                 300

Asp Arg Val Thr Gly Lys Ile Glu Ala Phe Ala Ser Arg Ala Lys Ile
305                 310                 315                 320

Val His Val Asp Ile Asp Pro Ala Glu Ile Gly Lys Asn Lys Gln Pro
                325                 330                 335

His Val Ser Ile Cys Ala Asp Val Lys Leu Ala Leu Gln Gly Met Asn
            340                 345                 350

Ala Leu Leu Glu Gly Ser Thr Ser Lys Lys Ser Phe Asp Phe Gly Ser
        355                 360                 365
```

-continued

```
Trp  Asn  Asp  Glu  Leu  Asp  Gln  Gln  Lys  Arg  Glu  Phe  Pro  Leu  Gly  Tyr
     370                 375                      380

Lys  Thr  Ser  Asn  Glu  Glu  Ile  Gln  Pro  Gln  Tyr  Ala  Ile  Gln  Val  Leu
385                      390                      395                      400

Asp  Glu  Leu  Thr  Lys  Gly  Glu  Ala  Ile  Ile  Gly  Thr  Gly  Val  Gly  Gln
               405                      410                           415

His  Gln  Met  Trp  Ala  Ala  Gln  Tyr  Tyr  Thr  Tyr  Lys  Arg  Pro  Arg  Gln
               420                 425                      430

Trp  Leu  Ser  Ser  Ala  Gly  Leu  Gly  Ala  Met  Gly  Phe  Gly  Leu  Pro  Ala
          435                 440                      445

Ala  Ala  Gly  Ala  Ser  Val  Ala  Asn  Pro  Gly  Val  Thr  Val  Val  Asp  Ile
     450                 455                      460

Asp  Gly  Asp  Gly  Ser  Phe  Leu  Met  Asn  Val  Gln  Glu  Leu  Ala  Met  Ile
465                      470                 475                           480

Arg  Ile  Glu  Asn  Leu  Pro  Val  Lys  Val  Phe  Val  Leu  Asn  Asn  Gln  His
               485                      490                           495

Leu  Gly  Met  Val  Val  Gln  Trp  Glu  Asp  Arg  Phe  Tyr  Lys  Ala  Asn  Arg
               500                 505                      510

Ala  His  Thr  Tyr  Leu  Gly  Asn  Pro  Glu  Asn  Glu  Ser  Glu  Ile  Tyr  Pro
          515                 520                      525

Asp  Phe  Val  Thr  Ile  Ala  Lys  Gly  Phe  Asn  Ile  Pro  Ala  Val  Arg  Val
     530                      535                      540

Thr  Lys  Lys  Asn  Glu  Val  Arg  Ala  Ala  Ile  Lys  Lys  Met  Leu  Glu  Thr
545                      550                      555                      560

Pro  Gly  Pro  Tyr  Leu  Leu  Asp  Ile  Ile  Val  Pro  His  Gln  Glu  His  Val
               565                      570                      575

Leu  Pro  Met  Ile  Pro  Ser  Gly  Gly  Ala  Phe  Lys  Asp  Met  Ile  Leu  Asp
               580                      585                      590

Gly  Asp  Gly  Arg  Thr  Val  Tyr
               595
```

(2) INFORMATION FOR SEQ ID NO:4:

(i) SEQUENCE CHARACTERISTICS:
        (A) LENGTH: 638 amino acids
        (B) TYPE: amino acid
        (C) STRANDEDNESS:
        (D) TOPOLOGY: linear (ii) MOLECULE TYPE: protein (iii) HYPOTHETICAL: NO (vi) ORIGINAL SOURCE:
        (A) ORGANISM: Zea mays (xi) SEQUENCE DESCRIPTION: SEQ ID NO:4:

```
Met  Ala  Thr  Ala  Ala  Ala  Ala  Ser  Thr  Ala  Leu  Thr  Gly  Ala  Thr  Thr
1                   5                    10                       15

Ala  Ala  Pro  Lys  Ala  Arg  Arg  Arg  Ala  His  Leu  Leu  Ala  Thr  Arg  Arg
               20                  25                       30

Ala  Leu  Ala  Pro  Ile  Arg  Cys  Ser  Ala  Ala  Ser  Pro  Ala  Met  Pro
          35                  40                  45

Met  Ala  Pro  Pro  Ala  Thr  Pro  Leu  Arg  Pro  Trp  Gly  Pro  Thr  Asp  Pro
50                       55                       60

Arg  Lys  Gly  Ala  Asp  Ile  Leu  Val  Glu  Ser  Leu  Glu  Arg  Cys  Gly  Val
65                       70                       75                       80

Arg  Asp  Val  Phe  Ala  Tyr  Pro  Gly  Gly  Ala  Ser  Met  Glu  Ile  His  Gln
               85                       90                            95
```

```
Ala  Leu  Thr  Arg  Ser  Pro  Val  Ile  Ala  Asn  His  Leu  Phe  Arg  His  Glu
               100                 105                           110

Gln  Gly  Glu  Ala  Phe  Ala  Ala  Ser  Gly  Tyr  Ala  Arg  Ser  Ser  Gly  Arg
          115                      120                      125

Val  Gly  Val  Cys  Ile  Ala  Thr  Ser  Gly  Pro  Gly  Ala  Thr  Asn  Leu  Val
     130                      135                      140

Ser  Ala  Leu  Ala  Asp  Ala  Leu  Leu  Asp  Ser  Val  Pro  Met  Val  Ala  Ile
145                           150                 155                           160

Thr  Gly  Gln  Val  Pro  Arg  Arg  Met  Ile  Gly  Thr  Asp  Ala  Phe  Gln  Glu
                    165                      170                      175

Thr  Pro  Ile  Val  Glu  Val  Thr  Arg  Ser  Ile  Thr  Lys  His  Asn  Tyr  Leu
               180                      185                      190

Val  Leu  Asp  Val  Asp  Asp  Ile  Pro  Arg  Val  Val  Gln  Glu  Ala  Phe  Phe
          195                      200                 205

Leu  Ala  Ser  Ser  Gly  Arg  Pro  Gly  Pro  Val  Leu  Val  Asp  Ile  Pro  Lys
     210                      215                      220

Asp  Ile  Gln  Gln  Gln  Met  Ala  Val  Pro  Val  Trp  Asp  Lys  Pro  Met  Ser
225                           230                      235                      240

Leu  Pro  Gly  Tyr  Ile  Ala  Arg  Leu  Pro  Lys  Pro  Pro  Ala  Thr  Glu  Leu
               245                      250                      255

Leu  Glu  Gln  Val  Leu  Arg  Leu  Val  Gly  Ser  Arg  Arg  Pro  Val  Leu
               260                      265                      270

Tyr  Val  Gly  Gly  Gly  Cys  Ala  Ala  Ser  Gly  Glu  Glu  Leu  Arg  Arg  Phe
          275                      280                      285

Val  Glu  Leu  Thr  Gly  Ile  Pro  Val  Thr  Thr  Thr  Leu  Met  Gly  Leu  Gly
     290                      295                      300

Asn  Phe  Pro  Ser  Asp  Pro  Leu  Ser  Leu  Arg  Met  Leu  Gly  Met  His
305                           310                      315                      320

Gly  Thr  Val  Tyr  Ala  Asn  Tyr  Ala  Val  Asp  Lys  Ala  Asp  Leu  Leu  Leu
                    325                      330                      335

Ala  Leu  Gly  Val  Arg  Phe  Asp  Asp  Arg  Val  Thr  Gly  Lys  Ile  Glu  Ala
               340                      345                      350

Phe  Ala  Ser  Arg  Ala  Lys  Ile  Val  His  Val  Asp  Ile  Asp  Pro  Ala  Glu
          355                      360                      365

Ile  Gly  Lys  Asn  Lys  Gln  Pro  His  Val  Ser  Ile  Cys  Ala  Asp  Val  Lys
     370                      375                      380

Leu  Ala  Leu  Gln  Gly  Met  Asn  Ala  Leu  Leu  Glu  Gly  Ser  Thr  Ser  Lys
385                           390                      395                      400

Lys  Ser  Phe  Asp  Phe  Gly  Ser  Trp  Asn  Asp  Glu  Leu  Asp  Gln  Gln  Lys
                    405                      410                      415

Arg  Glu  Phe  Pro  Leu  Gly  Tyr  Lys  Thr  Ser  Asn  Glu  Glu  Ile  Gln  Pro
               420                      425                      430

Gln  Tyr  Ala  Ile  Gln  Val  Leu  Asp  Glu  Leu  Thr  Lys  Gly  Glu  Ala  Ile
          435                      440                      445

Ile  Gly  Thr  Gly  Val  Gly  Gln  His  Gln  Met  Trp  Ala  Ala  Gln  Tyr  Tyr
     450                      455                      460

Thr  Tyr  Lys  Arg  Pro  Arg  Gln  Trp  Leu  Ser  Ser  Ala  Gly  Leu  Gly  Ala
465                           470                      475                      480

Met  Gly  Phe  Gly  Leu  Pro  Ala  Ala  Ala  Gly  Ala  Ser  Val  Ala  Asn  Pro
                    485                      490                      495

Gly  Val  Thr  Val  Val  Asp  Ile  Asp  Gly  Asp  Gly  Ser  Phe  Leu  Met  Asn
                    500                      505                      510

Val  Gln  Glu  Leu  Ala  Met  Ile  Arg  Ile  Glu  Asn  Leu  Pro  Val  Lys  Val
```

|     |     |     |     | 515 |     |     |     | 520 |     |     |     | 525 |     |     |
| --- | --- | --- | --- | --- | --- | --- | --- | --- | --- | --- | --- | --- | --- | --- |
| Phe | Val<br>530 | Leu | Asn | Asn | Gln | His<br>535 | Leu | Gly | Met | Val | Val<br>540 | Gln | Trp | Glu | Asp |
| Arg<br>545 | Phe | Tyr | Lys | Ala | Asn<br>550 | Arg | Ala | His | Thr | Tyr<br>555 | Leu | Gly | Asn | Pro | Glu<br>560 |
| Asn | Glu | Ser | Glu | Ile<br>565 | Tyr | Pro | Asp | Phe | Val<br>570 | Thr | Ile | Ala | Lys | Gly<br>575 | Phe |
| Asn | Ile | Pro | Ala<br>580 | Val | Arg | Val | Thr | Lys<br>585 | Lys | Asn | Glu | Val | Arg<br>590 | Ala | Ala |
| Ile | Lys | Lys<br>595 | Met | Leu | Glu | Thr | Pro<br>600 | Gly | Pro | Tyr | Leu | Leu<br>605 | Asp | Ile | Ile |
| Val | Pro<br>610 | His | Gln | Glu | His | Val<br>615 | Leu | Pro | Met | Ile | Pro<br>620 | Ser | Gly | Gly | Ala |
| Phe<br>625 | Lys | Asp | Met | Ile | Leu<br>630 | Asp | Gly | Asp | Gly | Arg<br>635 | Thr | Val | Tyr |     |     |

(2) INFORMATION FOR SEQ ID NO:5:

(i) SEQUENCE CHARACTERISTICS:
        (A) LENGTH: 638 amino acids
        (B) TYPE: amino acid
        (C) STRANDEDNESS:
        (D) TOPOLOGY: linear (ii) MOLECULE TYPE: protein (iii) HYPOTHETICAL: NO (vi) ORIGINAL SOURCE:
        (A) ORGANISM: Zea mays (xi) SEQUENCE DESCRIPTION: SEQ ID NO:5:

| Met<br>1 | Ala | Thr | Ala | Ala<br>5 | Thr | Ala | Ala | Ala | Ala<br>10 | Leu | Thr | Gly | Ala | Thr<br>15 | Thr |
| --- | --- | --- | --- | --- | --- | --- | --- | --- | --- | --- | --- | --- | --- | --- | --- |
| Ala | Thr | Pro | Lys<br>20 | Ser | Arg | Arg | Arg | Ala<br>25 | His | His | Leu | Ala | Thr<br>30 | Arg | Arg |
| Ala | Leu | Ala<br>35 | Ala | Pro | Ile | Arg | Cys<br>40 | Ser | Ala | Leu | Ser | Arg<br>45 | Ala | Thr | Pro |
| Thr | Ala<br>50 | Pro | Pro | Ala | Thr | Pro<br>55 | Leu | Arg | Pro | Trp | Gly<br>60 | Pro | Asn | Glu | Pro |
| Arg<br>65 | Lys | Gly | Ser | Asp | Ile<br>70 | Leu | Val | Glu | Ala | Leu<br>75 | Glu | Arg | Cys | Gly | Val<br>80 |
| Arg | Asp | Val | Phe | Ala<br>85 | Tyr | Pro | Gly | Gly | Ala<br>90 | Ser | Met | Glu | Ile | His<br>95 | Gln |
| Ala | Leu | Thr | Arg<br>100 | Ser | Pro | Val | Ile | Ala<br>105 | Asn | His | Leu | Phe | Arg<br>110 | His | Glu |
| Gln | Gly | Glu<br>115 | Ala | Phe | Ala | Ala | Ser<br>120 | Ala | Tyr | Ala | Arg | Ser<br>125 | Ser | Gly | Arg |
| Val | Gly<br>130 | Val | Cys | Ile | Ala | Thr<br>135 | Ser | Gly | Pro | Gly | Ala<br>140 | Thr | Asn | Leu | Val |
| Ser<br>145 | Ala | Leu | Ala | Asp | Ala<br>150 | Leu | Leu | Asp | Ser | Val<br>155 | Pro | Met | Val | Ala | Ile<br>160 |
| Thr | Gly | Gln | Val | Pro<br>165 | Arg | Arg | Met | Ile | Gly<br>170 | Thr | Asp | Ala | Phe | Gln<br>175 | Glu |
| Thr | Pro | Ile | Val<br>180 | Glu | Val | Thr | Arg | Ser<br>185 | Ile | Thr | Lys | His | Asn<br>190 | Tyr | Leu |
| Val | Leu | Asp<br>195 | Val | Asp | Asp | Ile | Pro<br>200 | Arg | Val | Val | Gln | Glu<br>205 | Ala | Phe | Phe |

```
Leu Ala Ser Ser Gly Arg Pro Gly Pro Val Leu Val Asp Ile Pro Lys
    210                 215                 220
Asp Ile Gln Gln Gln Met Ala Val Pro Ala Trp Asp Thr Pro Met Ser
225                 230                 235                 240
Leu Pro Gly Tyr Ile Ala Arg Leu Pro Lys Pro Pro Ala Thr Glu Phe
                245                 250                 255
Leu Glu Gln Val Leu Arg Leu Val Gly Glu Ser Arg Arg Pro Val Leu
            260                 265                 270
Tyr Val Gly Gly Gly Cys Ala Ala Ser Gly Glu Glu Leu Cys Arg Phe
        275                 280                 285
Val Glu Leu Thr Gly Ile Pro Val Thr Thr Thr Leu Met Gly Leu Gly
    290                 295                 300
Asn Phe Pro Ser Asp Asp Pro Leu Ser Leu Arg Met Leu Gly Met His
305                 310                 315                 320
Gly Thr Val Tyr Ala Asn Tyr Ala Val Asp Lys Ala Asp Leu Leu Leu
                325                 330                 335
Ala Phe Gly Val Arg Phe Asp Asp Arg Val Thr Gly Lys Ile Glu Ala
            340                 345                 350
Phe Ala Gly Arg Ala Lys Ile Val His Ile Asp Ile Asp Pro Ala Glu
        355                 360                 365
Ile Gly Lys Asn Lys Gln Pro His Val Ser Ile Cys Ala Asp Val Lys
    370                 375                 380
Leu Ala Leu Gln Gly Met Asn Thr Leu Leu Glu Gly Ser Thr Ser Lys
385                 390                 395                 400
Lys Ser Phe Asp Phe Gly Ser Trp His Asp Glu Leu Asp Gln Gln Lys
                405                 410                 415
Arg Glu Phe Pro Leu Gly Tyr Lys Ile Phe Asn Glu Glu Ile Gln Pro
            420                 425                 430
Gln Tyr Ala Ile Gln Val Leu Asp Glu Leu Thr Lys Gly Glu Ala Ile
        435                 440                 445
Ile Ala Thr Gly Val Gly Gln His Gln Met Trp Ala Ala Gln Tyr Tyr
    450                 455                 460
Thr Tyr Lys Arg Pro Arg Gln Trp Leu Ser Ser Ala Gly Leu Gly Ala
465                 470                 475                 480
Met Gly Phe Gly Leu Pro Ala Ala Ala Gly Ala Ala Val Ala Asn Pro
                485                 490                 495
Gly Val Thr Val Val Asp Ile Asp Gly Asp Gly Ser Phe Leu Met Asn
            500                 505                 510
Ile Gln Glu Leu Ala Met Ile Arg Ile Glu Asn Leu Pro Val Lys Val
        515                 520                 525
Phe Val Leu Asn Asn Gln His Leu Gly Met Val Val Gln Trp Glu Asp
    530                 535                 540
Arg Phe Tyr Lys Ala Asn Arg Ala His Thr Phe Leu Gly Asn Pro Glu
545                 550                 555                 560
Asn Glu Ser Glu Ile Tyr Pro Asp Phe Val Ala Ile Ala Lys Gly Phe
                565                 570                 575
Asn Ile Pro Ala Val Arg Val Thr Lys Lys Ser Glu Val His Ala Ala
            580                 585                 590
Ile Lys Lys Met Leu Glu Ala Pro Gly Pro Tyr Leu Leu Asp Ile Ile
        595                 600                 605
Val Pro His Gln Glu His Val Leu Pro Met Ile Pro Ser Gly Gly Ala
    610                 615                 620
Phe Lys Asp Met Ile Leu Asp Gly Asp Gly Arg Thr Val Tyr
625                 630                 635
```

( 2 ) INFORMATION FOR SEQ ID NO:6:

( i ) SEQUENCE CHARACTERISTICS:
        ( A ) LENGTH: 667 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( x i ) SEQUENCE DESCRIPTION: SEQ ID NO:6:

```
Met Ala Ala Ala Ala Pro Ser Pro Ser Ser Ala Phe Ser Lys Thr
 1               5                  10                  15

Leu Ser Pro Ser Ser Ser Thr Ser Thr Leu Leu Pro Arg Ser Thr
                20                  25                  30

Phe Pro Phe Pro His His Pro His Lys Thr Thr Pro Pro Leu His
            35                  40                  45

Leu Thr His Thr His Ile His Ile His Ser Gln Arg Arg Phe Thr
        50                  55                  60

Ile Ser Asn Val Ile Ser Thr Asn Gln Lys Val Ser Gln Thr Glu Lys
65                  70                  75                  80

Thr Glu Thr Phe Val Ser Arg Phe Ala Pro Asp Glu Pro Arg Lys Gly
                85                  90                  95

Ser Asp Val Leu Val Glu Ala Leu Glu Arg Glu Gly Val Thr Asp Val
                100                 105                 110

Phe Ala Tyr Pro Gly Gly Ala Ser Met Glu Ile His Gln Ala Leu Thr
            115                 120                 125

Arg Ser Ser Ile Ile Arg Asn Val Leu Pro Arg His Glu Gln Gly Gly
130                 135                 140

Val Phe Ala Ala Glu Gly Tyr Ala Arg Ala Thr Gly Phe Pro Gly Val
145                 150                 155                 160

Cys Ile Ala Thr Ser Gly Pro Gly Ala Thr Asn Leu Val Ser Gly Leu
                165                 170                 175

Ala Asp Ala Leu Leu Asp Ser Val Pro Ile Val Ala Ile Thr Gly Gln
                180                 185                 190

Val Pro Arg Arg Met Ile Gly Thr Asp Ala Phe Gln Glu Thr Pro Ile
            195                 200                 205

Val Glu Val Thr Arg Ser Ile Thr Lys His Asn Tyr Leu Val Met Asp
210                 215                 220

Val Glu Asp Ile Pro Arg Val Val Arg Glu Ala Phe Phe Leu Ala Arg
225                 230                 235                 240

Ser Gly Arg Pro Gly Pro Ile Leu Ile Asp Val Pro Lys Asp Ile Gln
                245                 250                 255

Gln Gln Leu Val Ile Pro Asp Trp Asp Gln Pro Met Arg Leu Pro Gly
                260                 265                 270

Tyr Met Ser Arg Leu Pro Lys Leu Pro Asn Glu Met Leu Leu Glu Gln
            275                 280                 285

Ile Val Arg Leu Ile Ser Glu Ser Lys Lys Pro Val Leu Tyr Val Gly
        290                 295                 300

Gly Gly Cys Ser Gln Ser Ser Glu Asp Leu Arg Arg Phe Val Glu Leu
305                 310                 315                 320

Thr Gly Ile Pro Val Ala Ser Thr Leu Met Gly Leu Gly Ala Phe Pro
                325                 330                 335

Thr Gly Asp Glu Leu Ser Leu Ser Met Leu Gly Met His Gly Thr Val
```

```
                        340                        345                         350
        Tyr Ala Asn Tyr Ala Val Asp Ser Ser Asp Leu Leu Leu Ala Phe Gly
                    355                 360                 365
        Val Arg Phe Asp Asp Arg Val Thr Gly Lys Leu Glu Ala Phe Ala Ser
                    370                 375                 380
        Arg Ala Lys Ile Val His Ile Asp Ile Asp Ser Ala Glu Ile Gly Lys
        385                 390                 395                 400
        Asn Lys Gln Pro His Val Ser Ile Cys Ala Asp Ile Lys Leu Ala Leu
                            405                 410                 415
        Gln Gly Leu Asn Ser Ile Leu Glu Ser Lys Glu Gly Lys Leu Lys Leu
                        420                 425                 430
        Asp Phe Ser Ala Trp Arg Gln Glu Leu Thr Glu Gln Lys Val Lys His
                    435                 440                 445
        Pro Leu Asn Phe Lys Thr Phe Gly Asp Ala Ile Pro Pro Gln Tyr Ala
                    450                 455                 460
        Ile Gln Val Leu Asp Glu Leu Thr Asn Gly Asn Ala Ile Ile Ser Thr
        465                 470                 475                 480
        Gly Val Gly Gln His Gln Met Trp Ala Ala Gln Tyr Tyr Lys Tyr Arg
                            485                 490                 495
        Lys Pro Arg Gln Trp Leu Thr Ser Gly Gly Leu Gly Ala Met Gly Phe
                        500                 505                 510
        Gly Leu Pro Ala Ala Ile Gly Ala Ala Val Gly Arg Pro Asp Glu Val
                    515                 520                 525
        Val Val Asp Ile Asp Gly Asp Gly Ser Phe Ile Met Asn Val Gln Glu
                530                 535                 540
        Leu Ala Thr Ile Lys Val Glu Asn Leu Pro Val Lys Ile Met Leu Leu
        545                 550                 555                 560
        Asn Asn Gln His Leu Gly Met Val Val Gln Trp Glu Asp Arg Phe Tyr
                            565                 570                 575
        Lys Ala Asn Arg Ala His Thr Tyr Leu Gly Asn Pro Ser Asn Glu Ala
                        580                 585                 590
        Glu Ile Phe Pro Asn Met Leu Lys Phe Ala Glu Ala Cys Gly Val Pro
                    595                 600                 605
        Ala Ala Arg Val Thr His Arg Asp Asp Leu Arg Ala Ala Ile Gln Lys
                610                 615                 620
        Met Leu Asp Thr Pro Gly Pro Tyr Leu Leu Asp Val Ile Val Pro His
        625                 630                 635                 640
        Gln Glu His Val Leu Pro Met Ile Pro Ser Gly Gly Ala Phe Lys Asp
                            645                 650                 655
        Val Ile Thr Glu Gly Asp Gly Arg Ser Ser Tyr
                    660                 665
```

( 2 ) INFORMATION FOR SEQ ID NO:7:

( i ) SEQUENCE CHARACTERISTICS:
        ( A ) LENGTH: 664 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:7:

```
        Met Ala Ala Ala Ala Ala Ala Pro Ser Pro Ser Phe Ser Lys Thr Leu
        1                   5                   10                  15
        Ser Ser Ser Ser Ser Lys Ser Ser Thr Leu Leu Pro Arg Ser Thr Phe
                        20                  25                  30
```

```
Pro Phe Pro His His Pro His Lys Thr Thr Pro Pro Pro Leu His Leu
         35                  40                  45
Thr Pro Thr His Ile His Ser Gln Arg Arg Arg Phe Thr Ile Ser Asn
     50                  55                  60
Val Ile Ser Thr Thr Gln Lys Val Ser Glu Thr Gln Lys Ala Glu Thr
 65                  70                  75                  80
Phe Val Ser Arg Phe Ala Pro Asp Glu Pro Arg Lys Gly Ser Asp Val
                 85                  90                  95
Leu Val Glu Ala Leu Glu Arg Glu Gly Val Thr Asp Val Phe Ala Tyr
            100                 105                 110
Pro Gly Gly Ala Ser Met Glu Ile His Gln Ala Leu Thr Arg Ser Ser
            115                 120                 125
Ile Ile Arg Asn Val Leu Pro Arg His Glu Gln Gly Gly Val Phe Ala
        130                 135                 140
Ala Glu Gly Tyr Ala Arg Ala Thr Gly Phe Pro Gly Val Cys Ile Ala
145                 150                 155                 160
Thr Ser Gly Pro Gly Ala Thr Asn Leu Val Ser Gly Leu Ala Asp Ala
                165                 170                 175
Leu Leu Asp Ser Val Pro Ile Val Ala Ile Thr Gly Gln Val Pro Arg
            180                 185                 190
Arg Met Ile Gly Thr Asp Ala Phe Gln Glu Thr Pro Ile Val Glu Val
            195                 200                 205
Thr Arg Ser Ile Thr Lys His Asn Tyr Leu Val Met Asp Val Glu Asp
    210                 215                 220
Ile Pro Arg Val Val Arg Glu Ala Phe Phe Leu Ala Arg Ser Gly Arg
225                 230                 235                 240
Pro Gly Pro Val Leu Ile Asp Val Pro Lys Asp Ile Gln Gln Gln Leu
                245                 250                 255
Val Ile Pro Asp Trp Asp Gln Pro Met Arg Leu Pro Gly Tyr Met Ser
            260                 265                 270
Arg Leu Pro Lys Leu Pro Asn Glu Met Leu Leu Glu Gln Ile Val Arg
            275                 280                 285
Leu Ile Ser Glu Ser Lys Lys Pro Val Leu Tyr Val Gly Gly Gly Cys
290                 295                 300
Ser Gln Ser Ser Glu Glu Leu Arg Arg Phe Val Glu Leu Thr Gly Ile
305                 310                 315                 320
Pro Val Ala Ser Thr Leu Met Gly Leu Gly Ala Phe Pro Thr Gly Asp
                325                 330                 335
Glu Leu Ser Leu Ser Met Leu Gly Met His Gly Thr Val Tyr Ala Asn
            340                 345                 350
Tyr Ala Val Asp Ser Ser Asp Leu Leu Leu Ala Phe Gly Val Arg Phe
            355                 360                 365
Asp Asp Arg Val Thr Gly Lys Leu Glu Ala Phe Ala Ser Arg Ala Lys
        370                 375                 380
Ile Val His Ile Asp Ile Asp Ser Ala Glu Ile Gly Lys Asn Lys Gln
385                 390                 395                 400
Pro His Val Ser Ile Cys Ala Asp Ile Lys Leu Ala Leu Gln Gly Leu
                405                 410                 415
Asn Ser Ile Leu Glu Ser Lys Glu Gly Lys Leu Lys Leu Asp Phe Ser
            420                 425                 430
Ala Trp Arg Gln Glu Leu Thr Val Gln Lys Val Lys Tyr Pro Leu Asn
        435                 440                 445
Phe Lys Thr Phe Gly Asp Ala Ile Pro Pro Gln Tyr Ala Ile Gln Val
```

|   |   |   |   | 450 |   |   |   |   | 455 |   |   |   |   | 460 |   |
|---|---|---|---|---|---|---|---|---|---|---|---|---|---|---|---|

Leu Asp Glu Leu Thr Asn Gly Ser Ala Ile Ile Ser Thr Gly Val Gly
465                 470                 475                 480

Gln His Gln Met Trp Ala Ala Gln Tyr Tyr Lys Tyr Arg Lys Pro Arg
                485                 490                 495

Gln Trp Leu Thr Ser Gly Gly Leu Gly Ala Met Gly Phe Gly Leu Pro
            500                 505                 510

Ala Ala Ile Gly Ala Ala Val Gly Arg Pro Asp Glu Val Val Val Asp
        515                 520                 525

Ile Asp Gly Asp Gly Ser Phe Ile Met Asn Val Gln Glu Leu Ala Thr
    530                 535                 540

Ile Lys Val Glu Asn Leu Pro Val Lys Ile Met Leu Leu Asn Asn Gln
545                 550                 555                 560

His Leu Gly Met Val Val Gln Trp Glu Asp Arg Phe Tyr Lys Ala Asn
                565                 570                 575

Arg Ala His Thr Tyr Leu Gly Asn Pro Ser Asn Glu Ala Glu Ile Phe
                580                 585                 590

Pro Asn Met Leu Lys Phe Ala Glu Ala Cys Gly Val Pro Ala Ala Arg
            595                 600                 605

Val Thr His Arg Asp Asp Leu Arg Ala Ala Ile Gln Lys Met Leu Asp
    610                 615                 620

Thr Pro Gly Pro Tyr Leu Leu Asp Val Ile Val Pro His Gln Glu His
625                 630                 635                 640

Val Leu Pro Met Ile Pro Ser Gly Gly Ala Phe Lys Asp Val Ile Thr
                645                 650                 655

Glu Gly Asp Gly Arg Ser Ser Tyr
                660

( 2 ) INFORMATION FOR SEQ ID NO:8:

( i ) SEQUENCE CHARACTERISTICS:
        ( A ) LENGTH: 671 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Arabidopsis thaliana ( x i ) SEQUENCE DESCRIPTION: SEQ ID NO:8:

Met Ala Ala Ala Thr Thr Thr Thr Thr Ser Ser Ser Ile Ser Phe
1               5                   10                  15

Ser Thr Lys Pro Ser Pro Ser Ser Lys Ser Pro Leu Pro Ile Ser
                20                  25                  30

Arg Phe Ser Leu Pro Phe Ser Leu Asn Pro Asn Lys Ser Ser Ser
            35                  40                  45

Ser Arg Arg Arg Gly Ile Lys Ser Ser Pro Ser Ser Ile Ser Ala
        50                  55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
            100                 105                 110

-continued

```
Glu  Thr  Val  Phe  Ala  Tyr  Pro  Gly  Gly  Ala  Ser  Met  Glu  Ile  His  Gln
          115                      120                      125

Ala  Leu  Thr  Arg  Ser  Ser  Ser  Ile  Arg  Asn  Val  Leu  Pro  Arg  His  Glu
     130                      135                      140

Gln  Gly  Gly  Val  Phe  Ala  Glu  Gly  Tyr  Ala  Arg  Ser  Ser  Gly  Lys
145                      150                      155                      160

Pro  Gly  Ile  Cys  Ile  Ala  Thr  Ser  Gly  Pro  Ala  Thr  Asn  Leu  Val
                    165                      170                      175

Ser  Gly  Leu  Ala  Asp  Ala  Leu  Leu  Asp  Ser  Val  Pro  Leu  Val  Ala  Ile
               180                      185                      190

Thr  Gly  Gln  Val  Pro  Arg  Arg  Met  Ile  Gly  Thr  Asp  Ala  Phe  Gln  Glu
          195                      200                      205

Thr  Pro  Ile  Val  Glu  Val  Thr  Arg  Ser  Ile  Thr  Lys  His  Asn  Tyr  Leu
     210                      215                      220

Val  Met  Asp  Val  Glu  Asp  Ile  Pro  Arg  Ile  Ile  Glu  Glu  Ala  Phe  Phe
225                      230                      235                      240

Leu  Ala  Thr  Ser  Gly  Arg  Pro  Gly  Pro  Val  Leu  Val  Asp  Val  Pro  Lys
                    245                      250                      255

Asp  Ile  Gln  Gln  Gln  Leu  Ala  Ile  Pro  Asn  Trp  Glu  Gln  Ala  Met  Arg
               260                      265                      270

Leu  Pro  Gly  Tyr  Met  Ser  Arg  Met  Pro  Lys  Pro  Pro  Glu  Asp  Ser  His
          275                      280                      285

Leu  Glu  Gln  Ile  Val  Arg  Leu  Ile  Ser  Glu  Ser  Lys  Lys  Pro  Val  Leu
     290                      295                      300

Tyr  Val  Gly  Gly  Gly  Cys  Leu  Asn  Ser  Ser  Asp  Glu  Leu  Gly  Arg  Phe
305                      310                      315                      320

Val  Glu  Leu  Thr  Gly  Ile  Pro  Val  Ala  Ser  Thr  Leu  Met  Gly  Leu  Gly
                    325                      330                      335

Ser  Tyr  Pro  Cys  Asp  Asp  Glu  Leu  Ser  Leu  His  Met  Leu  Gly  Met  His
               340                      345                      350

Gly  Thr  Val  Tyr  Ala  Asn  Tyr  Ala  Val  Glu  His  Ser  Asp  Leu  Leu  Leu
          355                      360                      365

Ala  Phe  Gly  Val  Arg  Phe  Asp  Asp  Arg  Val  Thr  Gly  Lys  Leu  Glu  Ala
     370                      375                      380

Phe  Ala  Ser  Arg  Ala  Lys  Ile  Val  His  Ile  Asp  Ile  Asp  Ser  Ala  Glu
385                      390                      395                      400

Ile  Gly  Lys  Asn  Lys  Thr  Pro  His  Val  Ser  Val  Cys  Gly  Asp  Val  Lys
                    405                      410                      415

Leu  Ala  Leu  Gln  Gly  Met  Asn  Lys  Val  Leu  Glu  Asn  Arg  Ala  Glu  Glu
               420                      425                      430

Leu  Lys  Leu  Asp  Phe  Gly  Val  Trp  Arg  Asn  Glu  Leu  Asn  Val  Gln  Lys
          435                      440                      445

Gln  Lys  Phe  Pro  Leu  Ser  Phe  Lys  Thr  Phe  Gly  Glu  Ala  Ile  Pro  Pro
450                      455                      460

Gln  Tyr  Ala  Ile  Lys  Val  Leu  Asp  Glu  Leu  Thr  Asp  Gly  Lys  Ala  Ile
465                      470                      475                      480

Ile  Ser  Thr  Gly  Val  Gly  Gln  His  Gln  Met  Trp  Ala  Ala  Gln  Phe  Tyr
                    485                      490                      495

Asn  Tyr  Lys  Lys  Pro  Arg  Arg  Gln  Trp  Leu  Ser  Ser  Gly  Gly  Leu  Gly
               500                      505                      510

Ala  Met  Gly  Phe  Gly  Leu  Pro  Ala  Ala  Ile  Gly  Ala  Ser  Val  Ala  Asn
          515                      520                      525

Pro  Asp  Ala  Ile  Val  Val  Asp  Ile  Asp  Gly  Asp  Gly  Ser  Phe  Ile  Met
     530                      535                      540
```

|     |     |     |     |     |     |     |     |     |     |     |     |     |     |     |
|-----|-----|-----|-----|-----|-----|-----|-----|-----|-----|-----|-----|-----|-----|-----|
| Asn | Val | Gln | Glu | Leu | Ala | Thr | Ile | Arg | Val | Glu | Asn | Leu | Pro | Val | Lys |
| 545 |     |     |     |     | 550 |     |     |     |     | 555 |     |     |     |     | 560 |
| Val | Leu | Leu | Leu | Asn | Asn | Gln | His | Leu | Gly | Met | Val | Met | Gln | Trp | Glu |
|     |     |     |     | 565 |     |     |     |     | 570 |     |     |     |     | 575 |     |
| Asp | Arg | Phe | Tyr | Lys | Ala | Asn | Arg | Ala | His | Thr | Phe | Leu | Gly | Asp | Pro |
|     |     |     | 580 |     |     |     |     | 585 |     |     |     |     | 590 |     |     |
| Ala | Gln | Glu | Asp | Glu | Ile | Phe | Pro | Asn | Met | Leu | Leu | Phe | Ala | Ala | Ala |
|     |     | 595 |     |     |     |     | 600 |     |     |     |     | 605 |     |     |     |
| Cys | Gly | Ile | Pro | Ala | Ala | Arg | Val | Thr | Lys | Lys | Ala | Asp | Leu | Arg | Glu |
|     | 610 |     |     |     |     | 615 |     |     |     |     | 620 |     |     |     |     |
| Ala | Ile | Gln | Thr | Met | Leu | Asp | Thr | Pro | Gly | Pro | Tyr | Leu | Leu | Asp | Val |
| 625 |     |     |     |     | 630 |     |     |     |     | 635 |     |     |     |     | 640 |
| Ile | Cys | Pro | His | Gln | Glu | His | Val | Leu | Pro | Met | Ile | Pro | Asn | Gly | Gly |
|     |     |     |     | 645 |     |     |     |     | 650 |     |     |     |     | 655 |     |
| Thr | Phe | Asn | Asp | Val | Ile | Thr | Glu | Gly | Asp | Gly | Arg | Ile | Lys | Tyr |
|     |     |     | 660 |     |     |     |     | 665 |     |     |     |     | 670 |     |

( 2 ) INFORMATION FOR SEQ ID NO:9:

( i ) SEQUENCE CHARACTERISTICS:
        ( A ) LENGTH: 652 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Brassica napus ( x i ) SEQUENCE DESCRIPTION: SEQ ID NO:9:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Ala | Ala | Ala | Thr | Ser | Ser | Ser | Pro | Ile | Ser | Leu | Thr | Ala | Lys | Pro |
| 1   |     |     |     | 5   |     |     |     |     | 10  |     |     |     |     | 15  |     |
| Ser | Ser | Lys | Ser | Pro | Leu | Pro | Ile | Ser | Arg | Phe | Ser | Leu | Pro | Phe | Ser |
|     |     |     | 20  |     |     |     |     | 25  |     |     |     |     | 30  |     |     |
| Leu | Thr | Pro | Gln | Lys | Pro | Ser | Ser | Arg | Leu | His | Arg | Pro | Leu | Ala | Ile |
|     |     | 35  |     |     |     |     | 40  |     |     |     |     | 45  |     |     |     |
| Ser | Ala | Val | Leu | Asn | Ser | Pro | Val | Asn | Val | Ala | Pro | Glu | Lys | Thr | Asp |
|     | 50  |     |     |     |     | 55  |     |     |     |     | 60  |     |     |     |     |
| Lys | Ile | Lys | Thr | Phe | Ile | Ser | Arg | Tyr | Ala | Pro | Asp | Glu | Pro | Arg | Lys |
| 65  |     |     |     |     | 70  |     |     |     |     | 75  |     |     |     |     | 80  |
| Gly | Ala | Asp | Ile | Leu | Val | Glu | Ala | Leu | Glu | Arg | Gln | Gly | Val | Glu | Thr |
|     |     |     |     | 85  |     |     |     |     | 90  |     |     |     |     | 95  |     |
| Val | Phe | Ala | Tyr | Pro | Gly | Gly | Ala | Ser | Met | Glu | Ile | His | Gln | Ala | Leu |
|     |     |     | 100 |     |     |     |     | 105 |     |     |     |     | 110 |     |     |
| Thr | Arg | Ser | Ser | Thr | Ile | Arg | Asn | Val | Leu | Pro | Arg | His | Glu | Gln | Gly |
|     |     |     | 115 |     |     |     |     | 120 |     |     |     |     | 125 |     |     |
| Gly | Val | Phe | Ala | Ala | Glu | Gly | Tyr | Ala | Arg | Ser | Ser | Gly | Lys | Pro | Gly |
|     |     | 130 |     |     |     |     | 135 |     |     |     |     | 140 |     |     |     |
| Ile | Cys | Ile | Ala | Thr | Ser | Gly | Pro | Gly | Ala | Thr | Asn | Leu | Val | Ser | Gly |
| 145 |     |     |     |     | 150 |     |     |     |     | 155 |     |     |     |     | 160 |
| Leu | Ala | Asp | Ala | Met | Leu | Asp | Ser | Val | Pro | Leu | Val | Ala | Ile | Thr | Gly |
|     |     |     |     | 165 |     |     |     |     | 170 |     |     |     |     | 175 |     |
| Gln | Val | Pro | Arg | Arg | Met | Ile | Gly | Thr | Asp | Ala | Phe | Gln | Glu | Thr | Pro |
|     |     |     | 180 |     |     |     |     | 185 |     |     |     |     | 190 |     |     |
| Ile | Val | Glu | Val | Thr | Arg | Ser | Ile | Thr | Lys | His | Asn | Tyr | Leu | Val | Met |

```
                    195                           200                           205

Asp  Val  Asp  Asp  Ile  Pro  Arg  Ile  Val  Gln  Glu  Ala  Phe  Phe  Leu  Ala
          210                      215                      220

Thr  Ser  Gly  Arg  Pro  Gly  Pro  Val  Leu  Val  Asp  Val  Pro  Lys  Asp  Ile
     225                      230                      235                      240

Gln  Gln  Gln  Leu  Ala  Ile  Pro  Asn  Trp  Asp  Gln  Pro  Met  Arg  Leu  Pro
                         245                      250                      255

Gly  Tyr  Met  Ser  Arg  Leu  Pro  Gln  Pro  Glu  Val  Ser  Gln  Leu  Gly
                    260                      265                      270

Gln  Ile  Val  Arg  Leu  Ile  Ser  Glu  Ser  Lys  Arg  Pro  Val  Leu  Tyr  Val
                    275                      280                      285

Gly  Gly  Gly  Ser  Leu  Asn  Ser  Ser  Glu  Glu  Leu  Gly  Arg  Phe  Val  Glu
          290                      295                      300

Leu  Thr  Gly  Ile  Pro  Val  Ala  Ser  Thr  Leu  Met  Gly  Leu  Gly  Ser  Tyr
     305                      310                      315                      320

Pro  Cys  Asn  Asp  Glu  Leu  Ser  Leu  Gln  Met  Leu  Gly  Met  His  Gly  Thr
                              325                      330                      335

Val  Tyr  Ala  Asn  Tyr  Ala  Val  Glu  His  Ser  Asp  Leu  Leu  Leu  Ala  Phe
                    340                      345                      350

Gly  Val  Arg  Phe  Asp  Asp  Arg  Val  Thr  Gly  Lys  Leu  Glu  Ala  Phe  Ala
               355                      360                      365

Ser  Arg  Ala  Lys  Ile  Val  His  Ile  Asp  Ile  Asp  Ser  Ala  Glu  Ile  Gly
          370                      375                      380

Lys  Asn  Lys  Thr  Pro  His  Val  Ser  Val  Cys  Gly  Asp  Val  Lys  Leu  Ala
     385                      390                      395                      400

Leu  Gln  Gly  Met  Asn  Lys  Val  Leu  Glu  Asn  Arg  Ala  Glu  Glu  Leu  Lys
                         405                      410                      415

Leu  Asp  Phe  Gly  Val  Trp  Arg  Ser  Glu  Leu  Ser  Glu  Gln  Lys  Gln  Lys
                    420                      425                      430

Phe  Pro  Leu  Ser  Phe  Lys  Thr  Phe  Gly  Glu  Ala  Ile  Pro  Pro  Gln  Tyr
                    435                      440                      445

Ala  Ile  Gln  Val  Leu  Asp  Glu  Leu  Thr  Gln  Gly  Lys  Ala  Ile  Ile  Ser
          450                      455                      460

Thr  Gly  Val  Gly  Gln  His  Gln  Met  Trp  Ala  Ala  Gln  Phe  Tyr  Lys  Tyr
     465                      470                      475                      480

Arg  Lys  Pro  Arg  Gln  Trp  Leu  Ser  Ser  Ser  Gly  Leu  Gly  Ala  Met  Gly
                         485                      490                      495

Phe  Gly  Leu  Pro  Ala  Ala  Ile  Gly  Ala  Ser  Val  Ala  Asn  Pro  Asp  Ala
                    500                      505                      510

Ile  Val  Val  Asp  Ile  Asp  Gly  Asp  Gly  Ser  Phe  Ile  Met  Asn  Val  Gln
                    515                      520                      525

Glu  Leu  Ala  Thr  Ile  Arg  Val  Glu  Asn  Leu  Pro  Val  Lys  Ile  Leu  Leu
          530                      535                      540

Leu  Asn  Asn  Gln  His  Leu  Gly  Met  Val  Met  Gln  Trp  Glu  Asp  Arg  Phe
     545                      550                      555                      560

Tyr  Lys  Ala  Asn  Arg  Ala  His  Thr  Tyr  Leu  Gly  Asp  Pro  Ala  Arg  Glu
                         565                      570                      575

Asn  Glu  Ile  Phe  Pro  Asn  Met  Leu  Gln  Phe  Ala  Gly  Ala  Cys  Gly  Ile
                    580                      585                      590

Pro  Ala  Ala  Arg  Val  Thr  Lys  Lys  Glu  Glu  Leu  Arg  Glu  Ala  Ile  Gln
               595                      600                      605

Thr  Met  Leu  Asp  Thr  Pro  Gly  Pro  Tyr  Leu  Leu  Asp  Val  Ile  Cys  Pro
     610                      615                      620
```

|  |  |  |  |  |  |  |  |  |  |  |  |  |  |  |
|---|---|---|---|---|---|---|---|---|---|---|---|---|---|---|
| His 625 | Gln | Glu | His | Val | Leu 630 | Pro | Met | Ile | Pro 635 | Ser | Gly | Gly | Thr | Phe | Lys 640 |
| Asp | Val | Ile | Thr | Glu 645 | Gly | Asp | Gly | Arg | Thr 650 | Lys | Tyr |

(2) INFORMATION FOR SEQ ID NO:10:

(i) SEQUENCE CHARACTERISTICS:
        (A) LENGTH: 637 amino acids
        (B) TYPE: amino acid
        (C) STRANDEDNESS:
        (D) TOPOLOGY: linear (ii) MOLECULE TYPE: protein (iii) HYPOTHETICAL: NO (vi) ORIGINAL SOURCE:
        (A) ORGANISM: Brassica napus (xi) SEQUENCE DESCRIPTION: SEQ ID NO:10:

| Met 1 | Ala | Ser | Phe | Ser 5 | Phe | Phe | Gly | Thr | Ile 10 | Pro | Ser | Ser | Pro | Thr 15 | Lys |
|---|---|---|---|---|---|---|---|---|---|---|---|---|---|---|---|
| Ala | Ser | Val | Phe 20 | Ser | Leu | Pro | Val 25 | Ser | Val | Thr | Thr | Leu 30 | Pro | Ser | Phe |
| Pro | Arg | Arg 35 | Arg | Ala | Thr | Arg | Val 40 | Ser | Val | Ser | Ala | Asn 45 | Ser | Lys | Lys |
| Asp | Gln 50 | Asp | Arg | Thr | Ala | Ser 55 | Arg | Arg | Glu | Asn | Pro 60 | Ser | Thr | Phe | Ser |
| Ser 65 | Lys | Tyr | Ala | Pro | Asn 70 | Val | Pro | Arg | Ser | Gly 75 | Ala | Asp | Ile | Leu | Val 80 |
| Glu | Ala | Leu | Glu | Arg 85 | Gln | Gly | Val | Asp | Val 90 | Val | Phe | Ala | Tyr | Pro 95 | Gly |
| Gly | Ala | Ser | Met | Glu 100 | Ile | His | Gln | Ala | Leu 105 | Thr | Arg | Ser | Asn | Thr 110 | Ile |
| Arg | Asn | Val | Leu 115 | Pro | Arg | His | Glu | Gln 120 | Gly | Gly | Ile | Phe | Ala 125 | Ala | Glu |
| Gly | Tyr 130 | Ala | Arg | Ser | Ser | Gly 135 | Lys | Pro | Gly | Ile | Cys 140 | Ile | Ala | Thr | Ser |
| Gly 145 | Pro | Gly | Ala | Met | Asn 150 | Leu | Val | Ser | Gly | Leu 155 | Ala | Asp | Ala | Leu | Phe 160 |
| Asp | Ser | Val | Pro | Leu 165 | Ile | Ala | Ile | Thr | Gly 170 | Gln | Val | Pro | Arg | Arg 175 | Met |
| Ile | Gly | Thr | Met 180 | Ala | Phe | Gln | Glu | Thr 185 | Pro | Val | Val | Glu | Val 190 | Thr | Arg |
| Thr | Ile | Thr 195 | Lys | His | Asn | Tyr | Leu 200 | Val | Met | Glu | Val | Asp 205 | Asp | Ile | Pro |
| Arg | Ile 210 | Val | Arg | Glu | Ala | Phe 215 | Phe | Leu | Ala | Thr | Ser 220 | Val | Arg | Pro | Gly |
| Pro 225 | Val | Leu | Ile | Asp | Val 230 | Pro | Lys | Asp | Val | Gln 235 | Gln | Gln | Phe | Ala | Ile 240 |
| Pro | Asn | Trp | Glu | Gln 245 | Pro | Met | Arg | Leu | Pro 250 | Leu | Tyr | Met | Ser | Thr 255 | Met |
| Pro | Lys | Pro | Pro 260 | Lys | Val | Ser | His | Leu 265 | Glu | Gln | Ile | Leu | Arg 270 | Leu | Val |
| Ser | Glu | Ser 275 | Lys | Arg | Pro | Val | Leu 280 | Tyr | Val | Gly | Gly | Gly 285 | Cys | Leu | Asn |
| Ser | Ser 290 | Glu | Glu | Leu | Arg | Arg 295 | Phe | Val | Glu | Leu | Thr 300 | Gly | Ile | Pro | Val |

```
Ala  Ser  Thr  Phe  Met  Gly  Leu  Gly  Ser  Tyr  Pro  Cys  Asp  Asp  Glu  Glu
305            310                      315                           320

Phe  Ser  Leu  Gln  Met  Leu  Gly  Met  His  Gly  Thr  Val  Tyr  Ala  Asn  Tyr
               325                      330                      335

Ala  Val  Glu  Tyr  Ser  Asp  Leu  Leu  Leu  Ala  Phe  Gly  Val  Arg  Phe  Asp
               340                 345                      350

Asp  Arg  Val  Thr  Gly  Lys  Leu  Glu  Ala  Phe  Ala  Ser  Arg  Ala  Lys  Ile
          355                      360                 365

Val  His  Ile  Asp  Ile  Asp  Ser  Thr  Glu  Ile  Gly  Lys  Asn  Lys  Thr  Pro
     370                      375                 380

His  Val  Ser  Val  Cys  Cys  Asp  Val  Gln  Leu  Ala  Leu  Gln  Gly  Met  Asn
385                      390                 395                           400

Glu  Val  Leu  Glu  Asn  Arg  Arg  Asp  Val  Leu  Asp  Phe  Gly  Glu  Trp  Arg
               405                      410                      415

Cys  Glu  Leu  Asn  Glu  Gln  Arg  Leu  Lys  Phe  Pro  Leu  Arg  Tyr  Lys  Thr
               420                 425                      430

Phe  Gly  Glu  Glu  Ile  Pro  Pro  Gln  Tyr  Ala  Ile  Gln  Leu  Leu  Asp  Glu
          435                 440                      445

Leu  Thr  Asp  Gly  Lys  Ala  Ile  Ile  Thr  Thr  Gly  Val  Gly  Gln  His  Gln
     450                      455                 460

Met  Trp  Ala  Ala  Gln  Phe  Tyr  Arg  Phe  Lys  Lys  Pro  Arg  Gln  Trp  Leu
465                      470                 475                           480

Ser  Ser  Gly  Gly  Leu  Gly  Ala  Met  Gly  Phe  Gly  Leu  Pro  Ala  Ala  Met
               485                      490                      495

Gly  Ala  Ala  Ile  Ala  Asn  Pro  Gly  Ala  Val  Val  Val  Asp  Ile  Asp  Gly
               500                      505                      510

Asp  Gly  Ser  Phe  Ile  Met  Asn  Ile  Gln  Glu  Leu  Ala  Thr  Ile  Arg  Val
          515                      520                      525

Glu  Asn  Leu  Pro  Val  Lys  Val  Leu  Leu  Ile  Asn  Asn  Gln  His  Leu  Gly
     530                      535                      540

Met  Val  Leu  Gln  Trp  Glu  Asp  His  Phe  Tyr  Ala  Ala  Asn  Arg  Ala  Asp
545                      550                      555                      560

Ser  Phe  Leu  Gly  Asp  Pro  Ala  Asn  Pro  Glu  Ala  Val  Phe  Pro  Asp  Met
               565                      570                      575

Leu  Leu  Phe  Ala  Ala  Ser  Cys  Gly  Ile  Pro  Ala  Ala  Arg  Val  Thr  Arg
               580                      585                      590

Arg  Glu  Asp  Leu  Arg  Glu  Ala  Ile  Gln  Thr  Met  Leu  Asp  Thr  Pro  Gly
          595                      600                      605

Pro  Phe  Leu  Leu  Asp  Val  Val  Cys  Pro  His  Gln  Asp  His  Val  Leu  Pro
     610                      615                      620

Leu  Ile  Pro  Ser  Gly  Gly  Thr  Phe  Lys  Asp  Ile  Ile  Val
625                      630                      635
```